US011501857B2

(12) United States Patent
Prybolsky et al.

(10) Patent No.: US 11,501,857 B2
(45) Date of Patent: Nov. 15, 2022

(54) METHODS FOR LOWERING BLOOD SUGAR WITH A METFORMIN PHARMACEUTICAL COMPOSITION

(71) Applicant: AstraZeneca UK Limited, Cambridge (GB)

(72) Inventors: Robert Peter Prybolsky, West Chester, PA (US); Judy Firor, Landenberg, PA (US)

(73) Assignee: ASTRAZENECA UK LIMITED, Cambridge (GB)

( * ) Notice: Subject to any disclaimer, the term of this patent is extended or adjusted under 35 U.S.C. 154(b) by 119 days.

(21) Appl. No.: 16/440,787

(22) Filed: Jun. 13, 2019

(65) Prior Publication Data
US 2019/0385712 A1    Dec. 19, 2019

Related U.S. Application Data

(60) Provisional application No. 62/685,211, filed on Jun. 14, 2018.

(51) Int. Cl.
*G16H 10/40* (2018.01)
*G16H 50/30* (2018.01)
*G16H 20/10* (2018.01)

(52) U.S. Cl.
CPC ............. *G16H 10/40* (2018.01); *G16H 20/10* (2018.01); *G16H 50/30* (2018.01)

(58) Field of Classification Search
CPC .......... A61P 3/00; G16H 20/10; G16H 15/00; G16H 20/60; G16H 20/13; G16H 50/30
See application file for complete search history.

(56) References Cited

U.S. PATENT DOCUMENTS

| 7,493,264 B1 | 2/2009 | Kelly et al. |
| 2005/0108053 A1 | 5/2005 | Jones |
| 2009/0125324 A1 | 5/2009 | Keravich et al. |
| 2011/0166876 A1 | 7/2011 | Chapman |
| 2011/0178812 A1 | 7/2011 | Lindsay |

(Continued)

FOREIGN PATENT DOCUMENTS

| WO | WO 2010/041052 A1 | 4/2010 | |
| WO | WO-2010041052 A1 * | 4/2010 | ......... G06F 19/3456 |

OTHER PUBLICATIONS

FDA, Highlights of Prescribing Information—Glumetza, Apr. 2011, FDA, pp. 1-25 (Year: 2011).*

(Continued)

*Primary Examiner* — Linh Giang Le
*Assistant Examiner* — Constantine Siozopoulos
(74) *Attorney, Agent, or Firm* — Brett A. Lovejoy; Andrew J. Antczak; Morgan, Lewis & Bockius LLP

(57) ABSTRACT

A method is provided for lowering blood sugar in a subject in need thereof by administering a biguanide anti-hyperglycemic pharmaceutical composition to a subject qualified for over-the-counter access to the biguanide anti-hyperglycemic pharmaceutical composition. In some embodiments, the biguanide anti-hyperglycemic pharmaceutical composition includes N,N-dimethylimidodicarbonimidic diamide, or a pharmaceutically acceptable salt thereof. In some embodiments, the biguanide anti-hyperglycemic pharmaceutical composition includes metformin hydrochloride.

19 Claims, 23 Drawing Sheets

(56) References Cited

U.S. PATENT DOCUMENTS

| | | | | |
|---|---|---|---|---|
| 2012/0150562 A1* | 6/2012 | Lerner | ............... | G16H 10/60 |
| | | | | 705/3 |
| 2013/0218586 A1* | 8/2013 | Huser | ............... | G06Q 20/20 |
| | | | | 705/2 |
| 2018/0165739 A1* | 6/2018 | Lawless | ............. | G16H 10/60 |

OTHER PUBLICATIONS

International Search Report and Written Opinion for International Patent Application No. PCT/US2019/037060, dated Nov. 27, 2019, 28 pages.
Setter et al., "Metformin Hydrochloride in the Treatment of Type 2 Diabetes Mellitus: A Clinical Review with a Focus on Dual Therapy", Clinical Therapeutics, Excerpta Medica, Princeton, NJ, vol. 25, No. 12, Dec. 1, 2003, vol. 1, No. 1, Nov. 24, 2017.
Ramkumar, S. et al., Acta Cardiol. Sin., 32(6):631-39 (2016).
Barias S. FDA Considers a New Paradigm for Over-the-Counter Medications: More Power-but More Burdens—for Pharmacists and Pharmacies. P T. May 2012;37(5):300-5. PubMed PMID: 22876088; PubMed Central PMCID: PMC3411219.
Crestor, Full Prescribing Information, 2012, AstraZeneca Pharmaceuticals LP.
Dyer O., "FDA Rejects sale of over the counter Statins", BMJ, Jan. 22, 2005; 330(7484):164.
May 9, 2013, power point presentations from the Engelberg Center for Health Care Reform.
Pfizer Wants Atorvastatin Available Over the Counter—Medscape—Aug. 4, 2011, downloaded from the Internet Nov. 30, 2018.
PR Newswire Association, "Americans Should Pay More Attention to Over-the-Counter (OTC) medicine Labels According to New Survey", Oct. 15, 2015 (citing McNeil Consumer Healthcare research).
Glumetza (metformin hydrochloride extended-release tablets) Prescribing Information, (Depomed, Inc.) Apr. 2011, [online], [retrieved on Feb. 28, 2021], Retrieved from the Internet: <URL: https://www.accessdata.fda.gov/drugsatfda_docs/label/2009/022350lbl.pdf>.
EMA Glubrava Label: GlubravaTablets—Summary of Product Characteristics; European Medicines Agency (EMA) https://www.ema.europa.eu/en/documents/product-information/glubrava-epar-product-information_en (35 pgs) (Mar. 25, 2021).
Riotmet ((metformin hydrochloride) Drug Facts Label: https://www.accessdata.fda.gov/drugsatfda_docs/label/2019/212595s000lbl (25 pgs) (Aug. 2019).
Both et al., Analysis of licensed over-the-counter (OTC) antibiotics in the European Union and Norway. Euro Surveill (2015).
Chang et al., Prescription to over-the-counter switches in the United States. Journal of Research in Pharmacy Practice. (2016).
Ferris et al., Over-the-Counter Antifungal Drug Misuse Associated With Patient-Diagnosed Vulvovaginal Candidiasis. Antifungal Drug Misuse. Obstetrics & Gynecology. vol. 99, No. 3, (2002) The American College of Obstetricians and Gynecologists.
Stomberg et al., Utilization effects of Rx-OTC switches and implications for future switches. Health. vol. 5, No. 10, 1667-1680 (2013).
Yuen and Chong, Rx-to-OTC Switch—An Overview and its Implications to Public Health. Pharmacy Education & Practice. vol. 25, No. 4 (2018).

\* cited by examiner

400

(402) A computer system for qualifying a human subject for over-the-counter delivery of a metformin pharmaceutical composition for lowering blood sugar. The computer system includes one or more processors and a memory. The memory includes non-transitory instructions which, when executed by the one or more processor, perform a method.

(404) The metformin pharmaceutical composition includes metformin hydrochloride.

(406) The lowering blood sugar is to treat or prevent diabetes.

(408) Conduct a first survey of the subject thereby obtaining a first plurality of survey results.

(410) The first plurality of survey results include whether the subject is any one of pregnant, breastfeeding, or planning to become pregnant, whether the subject has a kidney problem, a ketoacidosis status of the subject, an alcohol consumption status of the subject, an age of the subject, a Type 1 diabetes status of the subject, a lactic acidosis status of the subject, a blood sugar level of the subject, whether the subject has a liver problem, whether the subject has ever had a heart attack, severe infection, or stroke, a surgery status of the subject, whether the subject has a history of dehydration, and whether the subject is taking a diabetes medication.

Fig. 4A

(412) Run all or a portion of the first plurality of survey results against a first plurality of filters of a first category class. When a respective filter in the first plurality of filters is fired, the subject is deemed not qualified for delivery of the metformin pharmaceutical composition and the method is terminated without delivery of the metformin pharmaceutical composition to the subject.

(414) The first plurality of filters includes a first pregnancy filter that is fired at least when the first plurality of survey results indicates that the subject is pregnant or the subject is breastfeeding.

(416) The first pregnancy filter is also fired when the first plurality of survey results indicates that the subject is planning to become pregnant.

(418) The first plurality of filters includes a kidney function filter that is fired at least when the first plurality of survey results indicates that the subject has a kidney problem.

(420) The first plurality of filters includes a ketoacidosis filter that is fired at least when the first plurality of survey results indicates that the subject has ketoacidosis.

(422) The first plurality of filters includes a first alcohol consumption filter.

(424) The first alcohol consumption filter is fired when the first plurality of survey results indicates that the subject, on average, consumes at least a predetermined number of alcoholic drinks over a predetermined period of time.

(426) The first plurality of filters includes an age filter.

(428) The age filter is fired when the first plurality of survey results indicates that the subject is less than eighteen years old.

(430) The first plurality of filters includes a Type 1 diabetes filter that is fired at least when the first plurality of survey results indicates that the subject has Type 1 diabetes.

(432) The first plurality of filters includes a lactic acidosis filter that is fired at least when the first plurality of survey results indicates that the subject has lactic acidosis.

(434) The first plurality of filters includes a first blood sugar level filter that is fired at least when the first plurality of survey results indicates that the subject has a blood sugar level that is either below a first baseline blood sugar level, or above a ceiling blood sugar level.

(436) The first baseline blood sugar level used in the first blood sugar level filter is 6.5% glycated hemoglobin.

(438) The ceiling blood sugar level used in the first blood sugar level filter is 7.5% glycated hemoglobin.

(440) The first plurality of survey results further includes whether the subject is allergic to the metformin pharmaceutical composition, and the first plurality of filters includes an adverse reaction filter that is fired when the first plurality of survey results indicates that the subject is allergic to the metformin pharmaceutical composition.

(442) Run all or a portion of the first plurality of survey results against a second plurality of filters of a second category class. When a respective filter in the second plurality of filters is fired, the subject is provided with a warning corresponding to the respective filter.

(444) The second plurality of filters includes a first liver disease filter that is fired at least when the first plurality of survey results indicates that the subject has a liver problem.

(446) The second plurality of filters includes a first medical issue filter that is fired at least when the first plurality of survey results indicates that the subject has had a heart attack, the subject has had a severe infection, or the subject has had a stroke.

(448) The second plurality of filters includes a first surgery filter that is fired at least when the first plurality of survey results indicates that the subject has recently undergone surgery, the subject is planning on undergoing surgery, or the subject is planning on having an x-ray procedure that includes injection of a contrast agent.

(450) The second plurality of filters includes a first dehydration filter that is fired at least when the first plurality of survey results indicates that the subject has experienced a symptom of dehydration.

(452) The second plurality of filters includes a first diabetes medication filter that is fired at least when the first plurality of survey results indicates that the subject is taking a diabetes medication.

(454) The warning corresponding to a respective filter in the second plurality of filters includes a prompt for the subject to indicate whether they have discussed the risk factor underlying the respective filter in the second plurality of filters that was fired with a health care provider. Acknowledgement is obtained from the subject when the subject indicates that they have discussed the risk factor underlying the respective filter in the second plurality of filters that was fired with a health care provider.

(456) Obtain acknowledgment from the subject for the warning issued to the subject by any filter in the second plurality of filters.

Fig. 4C

(458) Proceed with a fulfillment process when no filter in the first plurality of filters has been fired and the subject has acknowledged each warning associated with each filter in the second plurality of filters that was fired.

(460) The fulfillment process includes storing an indication in a subject profile of an initial order for the metformin pharmaceutical composition, communicating an over the counter drug facts label for the metformin pharmaceutical composition to the subject, and authorizing, upon confirmation from the subject that the over the counter drug facts label has been received and read, provision of the metformin pharmaceutical composition to the subject.

(462) Upon confirmation from the subject that the over the counter drug facts label has been received and read, the subject is authorized for provision of a dosage of from 500 mg to 1000 mg per day of the metformin pharmaceutical composition.

(464) Upon confirmation from the subject that the over the counter drug facts label has been received and read, the subject is authorized for provision of a dosage of 500 mg per day of the metformin pharmaceutical composition.

(466) The fulfillment process further includes storing a destination associated with the subject in the subject profile.

(468) The fulfillment process further includes coordinating shipping of the metformin pharmaceutical composition to a physical address associated with the subject.

Fig. 4D

(470) Responsive to receiving a re-order request from the subject for the metformin pharmaceutical composition, performing a re-fulfillment procedure.

(472) Conduct a second survey of the subject thereby obtaining a second plurality of survey results.

(474) The second plurality of survey results includes whether the subject is one of pregnant, breastfeeding, or planning to become pregnant, whether the subject has experienced a kidney problem since receiving their last provision of the metformin pharmaceutical composition, an alcohol consumption status of the subject, whether the subject has experienced a symptom of ketoacidosis since receiving their last provision of the metformin pharmaceutical composition, whether the subject has experienced a symptom of lactic acidosis since receiving their last provision of the metformin pharmaceutical composition, whether the subject has experienced an illness causing vomiting, diarrhea, or fever since receiving their last provision of the metformin pharmaceutical composition, whether the subject has experienced a symptom of a liver problem since receiving their last provision of the metformin pharmaceutical composition, whether the subject has experienced a heart attack, severe infection, or stroke since receiving their last provision of the metformin pharmaceutical composition, a surgery status of the subject, whether the subject has experienced a symptom of dehydration since receiving their last provision of the metformin pharmaceutical composition, whether the subject is taking a diabetes medication, if the subject has been taking the metformin pharmaceutical composition for at least a predetermined period of time, and a blood sugar level of the subject.

Fig. 4E

(476) Run all or a portion of the second plurality of survey results against a third plurality of filters of the first category class. When a respective filter in the third plurality of filters is fired, the subject is deemed not qualified for the metformin pharmaceutical composition and the re-fulfillment process is terminated without delivery of the metformin pharmaceutical composition to the subject.

(478) The third plurality of filters includes a second pregnancy filter that is fired at least when the second plurality of survey results indicates that the subject is pregnant or the subject is breastfeeding.

(480) The second pregnancy filter is also fired when the second plurality of survey results indicates that the subject plans to become pregnant within a predetermined period of time.

(482) The third plurality of filters includes a kidney disease filter that is fired at least when the second plurality of survey results indicates that the subject has experienced a kidney problem since receiving their last provision of the metformin pharmaceutical composition.

(484) The third plurality of filters includes a second alcohol consumption filter.

(486) The second alcohol consumption filter is fired when the first plurality of survey results indicates that the subject, on average, consumes at least a predetermined number of alcoholic drinks over a predetermined period of time.

(488) The third plurality of filters includes a ketoacidosis symptom filter that is fired at least when the second plurality of survey results indicates that the subject has experienced a symptom of ketoacidosis since receiving their last provision of the metformin pharmaceutical composition.

(490) A symptom of ketoacidosis, which is capable of firing the ketoacidosis filter, is selected from the group consisting of an increase of ketones in the blood of the subject, an increase of ketones in the urine of the subject, nausea, tiredness, vomiting, trouble breather, and abdominal pain.

*(492)* The third plurality of filters includes a lactic acidosis symptom filter that is fired at least when the second plurality of survey results indicates that the subject has experienced a symptom of lactic acidosis since receiving their last provision of the metformin pharmaceutical composition.

*(494)* A symptom of lactic acidosis, which is capable of firing the lactic acidosis symptom filter, is selected from the group consisting of cold feelings in the subject's hands or feet, dizziness, lightheadedness, slow or irregular heartbeat, feeling very weak or tired, unusual muscle pain, difficulty breathing, stomach pains, nausea, and vomiting.

*(496)* The third plurality of filters includes an illness filter that is fired at least when the second plurality of survey results indicates that the user has experienced an illness causing vomiting, diarrhea, or fever since receiving their last provision of the metformin pharmaceutical composition.

*(498)* The third plurality of filters includes a second blood sugar filter that is fired at least when the subject has been taking the metformin pharmaceutical composition for a predetermined period of time, and the second plurality of survey results indicates that the subject has a blood sugar level of at least a second baseline blood sugar level.

*(500)* The second baseline blood sugar level used in the second blood sugar filter is 7% glycated hemoglobin.

Fig. 4G

(502) Run all or a portion of the second plurality of survey results against a fourth plurality of filters of the second category class. When a respective filter in the fourth plurality of filters is fired, the subject is provided with a warning corresponding to the respective filter.

(504) The fourth plurality of filters include a second liver disease filter that is fired at least when the second plurality of survey results indicates that the subject has experienced a liver problem since receiving their last provision of the metformin pharmaceutical composition, a second medical issue filter that is fired at least when the second plurality of survey results indicates that the subject has had a heart attack, the subject has had a severe infection, or the subject has had a stroke since receiving their last provision of the metformin pharmaceutical composition, a second surgery filter that is fired at least when the second plurality of survey results indicates that the subject has undergone surgery since receiving their last provision of the metformin pharmaceutical composition, the subject is planning on undergoing surgery, or the subject is planning on having an x-ray procedure that includes injection of a contrast agent since, a second dehydration filter that is fired at least when the second plurality of survey results indicates that the subject has experienced, since receiving their last provision of the metformin pharmaceutical composition, a symptom of dehydration, and a second diabetes medication filter that is fired at least when the second plurality of survey results indicates that the subject is taking a diabetes medication.

(506) The second plurality of survey results further includes whether the subject has experienced a side effect from the metformin pharmaceutical composition. The fourth plurality of filters further includes a side effect filter that is fired at least when the second plurality of survey results indicates that the subject has experienced, since receiving their last provision of the metformin pharmaceutical composition, a side effect selected from the group consisting of a metallic taste, diarrhea, nausea, and an upset stomach.

(508) When a respective filter in the third plurality of filters or fourth plurality of filters is fired, store a record associated with the firing of the respective filter in an adverse event profile comprising records of filter firing events associated with a plurality of subjects.

Fig. 4H

Are you or do you plan to become pregnant? Are you breastfeeding or planning to breastfeed? ⟵ 550
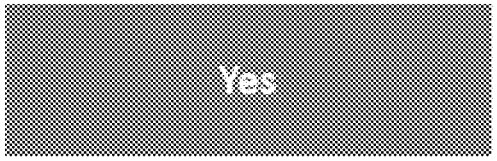 
Fig. 5A
Metformin OTC should be used in pregnancy only if the potential benefits justifies the potential risk to the baby. Only a doctor can decide that. Do not breast-feed while taking Metformin OTC. ⟵ 552
Thank you for visiting the site.
Fig. 5B Do you plan to have surgery or an x-ray procedure with injection of dye (contrast agent)? — 554

Do you drink a lot of alcoholic drinks, including binge drinking for short periods and drinking a lot of alcohol on a regular basis? — 556

Metformin OTC may not be right for you. Based on your answers, it is important to talk to your doctor about potential risks of taking Metformin OTC. It may be helpful to have your summary of answers when talking to your doctor.

Has your doctor said it is OK for you to take Metformin OTC?

METHODS FOR LOWERING BLOOD SUGAR WITH A METFORMIN PHARMACEUTICAL COMPOSITION

CROSS REFERENCE TO RELATED APPLICATIONS

This application claims priority to U.S. Provisional Patent Application Ser. No. 62/685,211, filed Jun. 14, 2018, which is hereby incorporated by reference in its entirety.

TECHNICAL FIELD

The present disclosure relates generally to methods for lowering blood sugar, e.g., thereby, treating Type 2 diabetes and/or maintaining sub-diabetic blood sugar levels, by administering an over-the-counter metformin extended release pharmaceutical composition to a subject in need thereof, who has been qualified for over-the-counter access to the composition.

BACKGROUND

Diabetes is a leading cause of death and increasing health care costs worldwide. NCD Risk Factor Collaboration, The Lancet, 387: 1513-1530 (2016). Since 1980, the number of people living with diabetes worldwide has nearly quadrupled. Id. As of 2015, according to the CDC, about 12% of all adults in the United States had diabetes and nearly 35% of all adults in the U.S. had prediabetes. Centers for Disease Control and Prevention, 'National Diabetes Statistics Report 2017' (2017). Further, nearly half of diabetes patients do not have their blood sugar under control. Polonsky et al., Patient Prefer. Adherence, 10:1299-1307. Moreover, diabetes poses a significant economical challenge. The American Diabetes Association estimated that in 2012, $245 billion was spent in direct and indirect medical expenses relating to diagnosed diabetes in the U.S. American Diabetes Association, Diabetes Care, 36(4):1033-46 (2013).

Fortunately, diabetes can be managed by, for example, using metformin composition, which are well established prescription pharmaceuticals used to lower blood sugar levels, thereby treating diabetes. For instance, the efficacy of metformin compositions, which was first approved in the U.S. for the treatment of diabetes in 1994, to lower blood sugar levels has been demonstrated in multiple double-blind, placebo-controlled, randomized studies. Garber et al., Efficacy of Metformin in Type II Diabetes: Results of a Double-Blind, Placebo-Controlled, Dose-Response Trial, Am J Med., 103(6), (1997). However, access to metformin compositions are restricted by the requirement for a prescription. Unfortunately, long-term trends demonstrate many people avoid prescription medications, including metformin compositions.

One approach to making metformin compositions more accessible is to make then available without a prescription, e.g., over the counter ("OTC"). There are a variety of health benefits derived from switching a drug from prescription to OTC including, but not limited to, generating wider availably to therapies, providing a greater number of therapeutic approaches, providing direct and rapid access to treatments, providing patients with an active role in their own health care, and allowing patients to become self-reliant in preventing and relieving minor symptoms or conditions World Health Organization, "Guidelines for the Regulatory Assessment of Medicinal Products for use in Self-Medication," 2000. Given the large number of individuals with uncontrolled high blood sugar, providing access to OTC metformin composition could provide significant societal health benefits.

However, switching distribution of a pharmaceutical from prescription-only to OTC creates a significant risk that the patient population will be unable to appropriately self-select themselves for safe use of the pharmaceutical and then self-medicate using the drug in a responsible manner. The manifestations embodied within these concerns include incorrect self-diagnosis, incorrect drug-qualification, unrecognized drug-drug interactions (DDI), unanticipated adverse drug reactions and/or side-effects, improper dosing and/or administration, masking of a disease, addiction, inappropriate drug dependency, substance abuse, and patient delay in seeking necessary medical attention. Ruiz et al., Current Drug Safety, 5(4):315 (2010).

Because metformin compositions cause adverse effects in certain patients, the population receiving the drug should be carefully selected and monitored. In order to ensure the safety of OTC distribution of metformin compositions, prospective patients must effectively self-select themselves for the drug. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey," Oct. 15, 2015 (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Currently, there are two regulatory pathways for legal marketing of an OTC drug in the United States. In the first pathway, marketing occurs in compliance with an OTC drug monograph, that sets regulatory standards for non-prescription drugs that are not covered by human drug applications, e.g., a New Drug Application (NDA) or Abbreviated New Drug Application (ANDA). An OTC monograph is created as a result of a three phase OTC drug review by the FDA. In phase I of the review, an advisory review panel determines whether ingredients in the proposed OTC composition could be generally recognized as safe and effective for use in self-treatment. In the second pathway, marketing occurs under the authority of an approved product-specific new drug application (NDA), or an abbreviated new drug application (ANDA). In order to support an over-the-counter label for a drug for which regulatory approval is being sought through an NDA, a consumer research study is required to assess the consumer's ability to select and deselect themselves as appropriate users of the drug, based on the proposed labeling for the drug. Oliver, A., Regulatory Rapporteur, 10(3):4-9 (2013), which is incorporated by reference herein.

However, attempts at switching distribution of drugs having potentially far-reaching benefits for societal health, from prescription-only to an OTC model, have repeatedly failed, in large part due to concerns over inappropriate patient selection and medication. Possibly the best documented cases relate to statins used to treat high cholesterol.

For instance, Merck has had at least three applications for sale of over the counter lovastatin rejected by the FDA, in 2000, 2005, and 2007. In 2005, their proposal to permit over the counter sales of lovastatin was rejected by an expert advisory panel at the FDA in 2005. The panel was concerned by a marketing study performed to support the proposal in which approximately one third of 3316 customers who were offered the drug over the counter decided they would purchase the drug. After reviewing the data, the panel concluded that 45% of the purchases would have been inappropriate for a variety of reasons, including the age of the subject, the subject's lack of knowledge about their condition, and contraindications associated with their condition. Dyer et al., BMJ, 330(7484):164 (2005). In 2007, the board again concluded that the ability of consumers to appropriately self-select and to adequately comply with chronic MEVACOR® therapy without the intervention of a physician had not been demonstrated. Division of Metabolic and Endocrine Drug Products, 2005, "NDA 21-213 Non-prescription MEVACOR® 20 mg Joint Advisory Committee Meeting."

Similarly, Pfizer announced in 2011 its intention to switch LIPITOR® from prescription-only to OTC status. Sett OTC bulletin, 16 Nov. 2011, page 7. However, they abandoned their attempt in 2014 when a phase 3 "actual use" trial, intended to simulate the OTC use of LIPITOR® (atorvastatin calcium) 10 mg, failed to meet its primary objectives on the basis that patient compliance with the direction to check their low-density lipoprotein cholesterol (LDL-C) level and, after checking their LDL-C level, take appropriate action based on their test results was unsatisfactory. Pfizer Inc., "Pfizer Reports Second-Quarter 2015 Results," (2015).

In fact, in the nearly two decades since Bristol-Myers Squibb and Merck & Co first failed in their attempts to switch PRAVACHOL® and lovastatin, respectively, to OTC, a statin has never been granted OTC status in the United States. This is despite that nearly ⅙th of the adult population in the U.S. is eligible for cholesterol-lowering medications, under the current guidelines, but are not taking anything.

The information disclosed in this Background section is only for enhancement of understanding of the general background of the invention and should not be taken as an acknowledgment or any form of suggestion that this information forms the prior art already known to a person skilled in the art.

SUMMARY

Given the above background, what is needed in the art are systems and methods for qualifying a human subject for delivery of a metformin pharmaceutical composition over-the-counter to lower blood sugar levels, e.g., thereby, treating Type 2 diabetes and/or maintaining sub-diabetic blood sugar levels.

The present disclosure addresses the need in the art for systems and methods configured for qualifying a human subject for over-the-counter delivery of a metformin pharmaceutical composition (e.g., metformin hydrochloride, extended release) for lowering blood sugar level, e.g., thereby, treating Type 2 diabetes and/or maintaining sub-diabetic blood sugar levels. In the present disclosure, systems and methods are provided for over-the-counter delivery of a metformin pharmaceutical composition to a subject. Survey results from the subject are run against a first plurality of filters. When a filter in the first plurality is fired, the subject is deemed not qualified for delivery of the metformin pharmaceutical composition. The survey results are also run against a second plurality of filters. When a respective filter in the second plurality is fired, the subject is provided with a corresponding warning. The method proceeds to a fulfillment process when no filter in the first plurality is fired and the subject has acknowledged each warning associated with each fired filter in the second plurality of filters. The fulfillment process stores the composition order, communicates a drug facts label for the metformin pharmaceutical composition to the subject, and authorizes, upon subject confirmation that the label has been read, provision of the metformin pharmaceutical composition to the subject.

Accordingly, one aspect of the present disclosure provides a method for qualifying a subject for over-the-counter delivery of a metformin pharmaceutical composition for lowering the blood sugar level of the subject, e.g., thereby, treating Type 2 diabetes and/or maintaining sub-diabetic blood sugar levels. The method includes conducting a first survey of the subject in order to obtain a variety of survey results. In some embodiments, the survey results indicate one or more of: whether the subject is any one of pregnant, breastfeeding, or planning to become pregnant, whether the subject has a kidney problem, a ketoacidosis status of the subject, an alcohol consumption status of the subject, an age of the subject, a Type 1 diabetes status of the subject, a lactic acidosis status of the subject, a blood sugar level of the subject, whether the subject has a liver problem, whether the subject has ever had a heart attack, severe infection, or stroke, a surgery status of the subject, whether the subject has a history of dehydration, and whether the subject is taking a diabetes medication.

The method also includes running all or a portion of the survey results against a first plurality of filters of a first category class, corresponding to contraindications associated with the metformin pharmaceutical composition. When a respective filter in the first plurality of filters is fired, the subject is deemed not qualified for delivery of the metformin pharmaceutical composition, and the method is then terminated accordingly without delivery of the metformin pharmaceutical composition to the subject. In some embodiments, the first plurality of filters includes one or more of a pregnancy filter, a kidney function filter, a ketoacidosis filter, an alcohol consumption filter, an age filter, a Type 1 diabetes filter, a lactic acidosis filter, and a blood sugar level filter.

The method also includes running all or a portion of the survey results against a second plurality of filters of a second category class, corresponding to risk factors associated with the metformin pharmaceutical composition. When a respective filter in the second plurality of filters is fired, the subject is provided with a warning corresponding to the respective filter. In some embodiments, the second plurality of filters includes one or more of a liver disease filter, a medical issue filter, a surgery filter, a dehydration filter, and a diabetes medication filter. However, unlike filters in the first plurality of filters, filters in the second plurality of filters do not automatically terminate the process without delivery of the metformin pharmaceutical composition to the subject.

The method continues by obtaining acknowledgment from the subject for the warning issued to the subject by any filter in the second plurality of filters.

The method continues by proceeding with a fulfillment process when no filter in the first plurality of filters has been fired and the subject has acknowledged each warning associated with each filter in the second plurality of filters that was fired.

In some embodiments, the fulfillment process includes storing an indication in a subject profile of an initial order for the metformin pharmaceutical composition, communicating an over-the-counter drug label for the metformin pharmaceutical composition, and authorizing, upon confirmation from the subject that the over-the-counter drug label has been received and read, provision of the metformin pharmaceutical composition to the subject.

In some embodiments, the metformin pharmaceutical composition is an extended release formulation of metformin hydrochloride or another pharmaceutically acceptable salt thereof (e.g., fumarate, succinate, etc.).

In one aspect, the present disclosure provides a method for qualifying a subject (e.g., a subject who was previously qualified to receive a provision of the metformin pharmaceutical composition) for a re-order of the metformin pharmaceutical composition (e.g., which is optionally performed in conjunction with a method for qualifying the subject for a first order of the metformin pharmaceutical composition). The method includes a re-fulfillment procedure that includes conducting a second survey of the subject in order to obtain a second plurality of survey results. In some embodiments, the second plurality of survey results indicate one or more of: whether the subject is one of (i) pregnant, (ii) breastfeeding, or (iii) planning to become pregnant, whether the subject has developed a kidney problem since receiving their last provision of the metformin pharmaceutical composition, an alcohol consumption status of the subject, whether the subject has developed ketoacidosis since receiving their last provision of the metformin pharmaceutical composition, whether the subject has developed lactic acidosis since receiving their last provision of the metformin pharmaceutical composition, whether the subject has experienced an illness causing vomiting, diarrhea, or fever since receiving their last provision of the metformin pharmaceutical composition, whether the subject has developed a liver problem since receiving their last provision of the metformin pharmaceutical composition, whether the subject has experienced a heart attack, severe infection, or stroke since receiving their last provision of the metformin pharmaceutical composition, a surgery status of the subject, whether the subject has experienced symptoms of dehydration since receiving their last provision of the metformin pharmaceutical composition, whether the subject is taking a diabetes medication, and a blood sugar level of the subject, if the subject has been taking the metformin pharmaceutical composition for at least a predetermined period of time.

The method also includes running all or a portion of the second plurality of survey results against a third plurality of filters of the first category class, corresponding to contraindications associated with the metformin pharmaceutical composition. When a respective filter in the third plurality of filters is fired, the subject is deemed not qualified for the metformin pharmaceutical composition, and the re-fulfillment process is terminated without delivery of the metformin pharmaceutical composition to the subject. In some embodiments, the third plurality of filters includes a pregnancy filter, a kidney disease filter, an alcohol consumption filter, a ketoacidosis symptom filter, a lactic acidosis symptom filter, an illness filter, and a blood sugar filter.

The method also includes running all or a portion of the second plurality of survey results against a fourth plurality of filters of the second category class, corresponding to risk factors associated with the metformin pharmaceutical composition. When a respective filter in the fourth plurality of filters is fired the subject is provided with a warning corresponding to the respective filter. In some embodiments, the fourth plurality of filters includes one or more of: a liver disease filter, a medical issue filter, a surgery filter, a dehydration filter, and a Type 1 diabetes filter.

The method continues by obtaining acknowledgment from the subject for the warning issued to the subject by any filter in the fourth plurality of filters. When the re-fulfillment process is not already terminated by the firing of a filter in the third plurality of filters, and the subject has acknowledged each warning associated with each filter in the fourth plurality of filters that was fired, the method continues with a re-fulfillment procedure.

In some embodiments, the method includes storing an indication in the subject profile of a re-order for the metformin pharmaceutical composition, communicating an over-the-counter drug facts label for the metformin pharmaceutical composition to the subject, and authorizing, upon confirmation from the subject that the over-the-counter drug facts label has been received and read, a re-order provision of the metformin pharmaceutical composition to the subject.

In some embodiments, the metformin pharmaceutical composition includes metformin hydrochloride, extended release.

BRIEF DESCRIPTION OF THE DRAWINGS

FIGS. 4A, 4B, 4C, 4D, 4E, 4F, 4G, 4H, and 4I collectively provide a flow chart of processes for qualifying a human subject for over-the-counter delivery of a metformin pharmaceutical composition to lower blood sugar levels, where elements in dashed boxes are optional, in accordance with various embodiments of the present disclosure.

FIGS. 5A, 5B, 5C, and 5D illustrate example survey questions for obtaining survey results, in accordance with an embodiment of the present disclosure.

Figure 1:
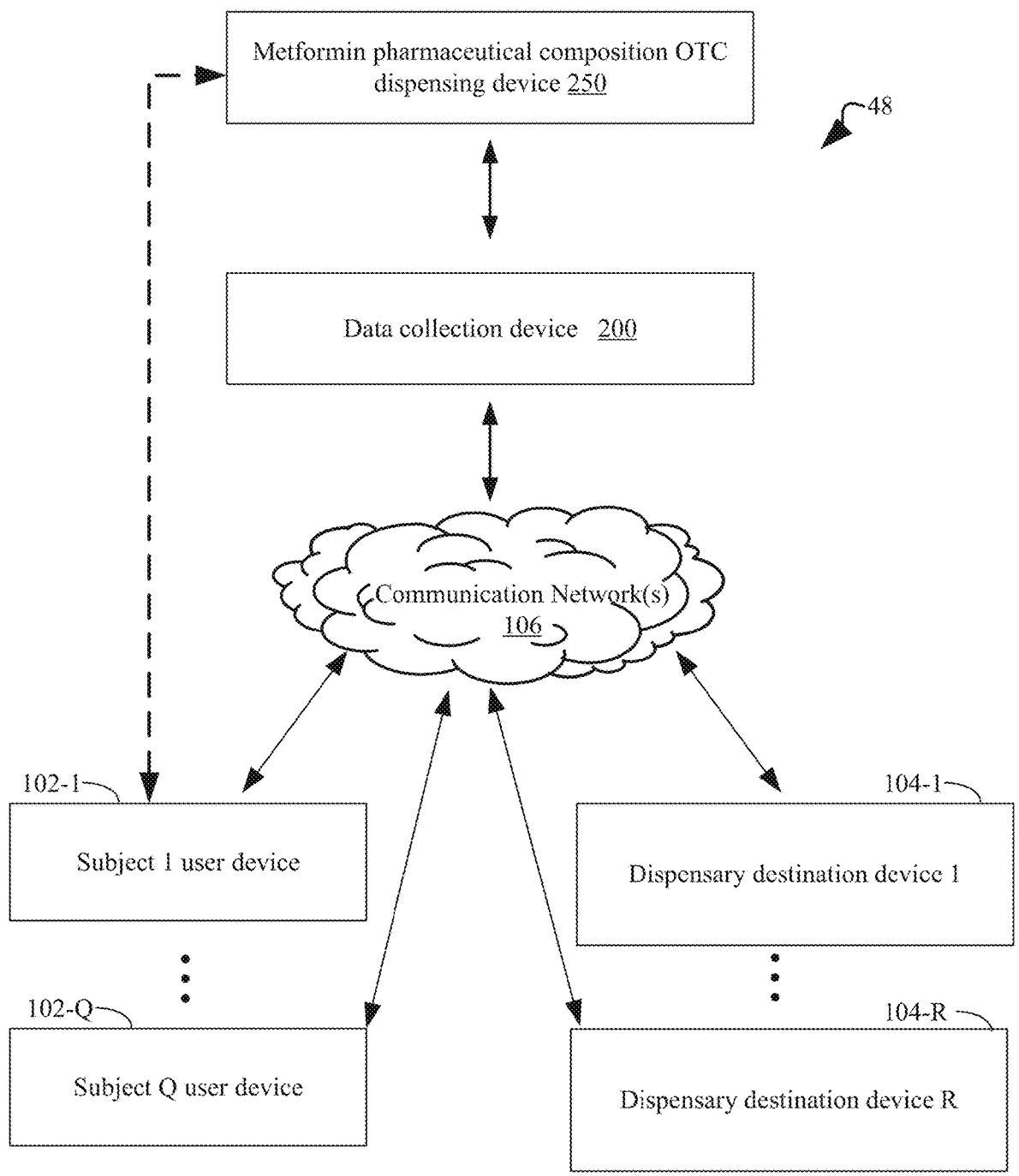
FIG. 1 illustrates an exemplary system topology that includes a metformin pharmaceutical composition over-the-counter (OTC) dispensing device for qualifying a human subject for over-the-counter delivery of a metformin pharmaceutical composition to lower blood sugar levels, a data collection device for collecting subject data, one or more user devices associated with human subjects, and one or more dispensary destinations for distributing the metformin pharmaceutical composition over-the-counter, where the above-identified components are interconnected, optionally through a communications network, in accordance with an embodiment of the present disclosure.

In the figures, reference numbers refer to the same or equivalent parts of the present invention throughout the several figures of the drawing.

DETAILED DESCRIPTION

Diabetes is a growing health problem, in the United States and worldwide. Although diabetes can be effectively treated using established pharmaceutical compositions, access to these drugs is hindered by to the requirement for a prescription, as many individuals do not have adequate access and/or avoid the healthcare system for a variety of reasons. Accordingly, many people are not managing their diabetes conditions appropriately. While over-the-counter alternatives to these prescription pharmaceuticals would increase access to these compositions, thereby improving population management of diabetes around the world, patients often have difficulty self-selecting themselves for an appropriate over-the-counter medication. Because inappropriate use of these drugs can result in ineffective treatment and/or serious side-effects, better methods for selecting for, and treating patients with, other-the-counter diabetes medications are needed. The present disclosure provides, among other aspects, methods, systems, and computer readable media that solve these problems.

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over-the-counter" means to provide by retail purchase, subject to the constraints disclosed herein, but without a prescription or license from a physician or medical practitioner.

As used herein, the term "pharmaceutical compound" refers to any physical state of a material. Pharmaceutical compounds include but are not limited to capsules, tablets, liquids, topical formulations, and inhaled formulations.

As used herein, the term "contraindication" refers to a condition that makes a treatment, e.g., over-the-counter use of a metformin pharmaceutical composition, inadvisable. Contraindications include physical characteristics of a subject, e.g., pregnancy or liver disease, and contemporaneous drug use, e.g., metformin pharmaceutical composition use. In the present context, identification of a contraindication fires a filter of a first category class, which prevents authorizing provision of a metformin pharmaceutical composition, in accordance with some implementations of the methods, systems, and software disclosed herein.

As used herein, the term "risk factor" refers to a condition that makes a treatment, e.g., over-the-counter use of a metformin pharmaceutical composition, possibly inadvisable. Risk factors include physical characteristics of a subject, e.g., a blood sugar level reading, and contemporaneous drug use, e.g., use of a diabetes medication. In the present context, identification of a risk factor fires a filter of a second category class, which prevents authorizing provision of a metformin pharmaceutical composition without confirmation that the subject has discussed the risk factor with a medical professional, in accordance with some implementations of the methods, systems, and software disclosed herein.

As used herein, "drug interactions," e.g., with a metformin, include pharmacokinetic drug interactions and pharmacodynamics drug interactions. Generally, a pharmacokinetic drug interaction is an interaction between two drugs (e.g., a metformin composition and a second drug) that result in alterations in the absorption, transport, distribution, metabolism, and/or excretion of either drug. Generally, a pharmacokinetic drug interaction is an interaction between two drugs (e.g., a metformin composition and a second drug) that result in a direct change in the effect or either drug. For a more comprehensive summary of pharmacokinetic drug interactions and pharmacodynamics drug interactions, see, Cascorbi, I, Dtsch Arztebl Int., 109(33-34):546-55 (2012), the content of which is hereby incorporated by reference.

In the context of the present disclosure, classification of a condition as either a contraindication or a risk factor is specific to a particular identity and dose of a metformin pharmaceutical composition being authorized for over-the-counter use. Classification of a particular condition, e.g., contemporaneous metformin pharmaceutical composition use, may vary between different metformin pharmaceutical compositions (e.g., it may be classified as a contraindication for a first metformin composition, a risk factor for a second metformin composition, and/or neither for a third metformin composition). Likewise, a particular condition may be classified as a contraindication for use of a particular metformin composition at a first over-the-counter dosage, classified as a risk factor for the same particular metformin composition at a second (e.g., lower) over-the-counter dosage, and/or classified as neither for the same particular metformin composition at a third (e.g., lowest) over-the-counter dosage.

As used herein, whether a subject "has developed" a condition since receiving their last provision of a metformin composition refers to both conditions that are new to the subject, i.e., a condition that the subject did not have at the time they received their last provision of the metformin composition, and conditions that have been newly diagnosed, regardless of whether the condition existed when the subject received their last provision of the metformin composition, i.e., a condition that the subject was not aware of when they received their last provision of the metformin composition.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

In one aspect of the present disclosure a survey of a subject is conducted to obtain survey results in order to determine if the subject qualifies for an over-the-counter (OTC) metformin pharmaceutical composition for lowering blood sugar, e.g., thereby, treating Type 2 diabetes and/or maintaining sub-diabetic blood sugar levels. The survey results are used as the basis for running filters of a first category class. If the triggering conditions of any of the filters in the first category class are fired, the subject does not qualify for the OTC metformin pharmaceutical composition. The survey results are also used as the basis for running filters of a second category class. If the triggering conditions of any of the filters in the second category class are fired, the subject is provided with warning messages associated with the respective filters of the second category class that have been fired. If none of the filters in the first category class are fired and the subject successfully addresses the warning messages associated with the respective filters of the second category class that have been fired a fulfillment process is initiated for OTC delivery of the metformin pharmaceutical composition.

FIG. 1 illustrates an example of an integrated system 48 for conducting one or more surveys of subjects in order to qualifying the subjects for OTC delivery of a metformin pharmaceutical composition. The integrated system 48 includes one or more connected user devices 102. The user devices 102 are configured for entering survey data and making requests for the metformin pharmaceutical composition. The system 48 also includes one or more dispensary destination devices 104 that are configured to receive instructions in order to provide the metformin pharmaceutical composition to qualifying subjects. Furthermore, the system 48 includes a metformin pharmaceutical composition over-the-counter (OTC) dispensing device 250 and one or more data collection devices 200 that are configured for collecting subject data.

Throughout the present disclosure, the data collection device 200 and the metformin pharmaceutical composition OTC dispensing device 250 will be referenced as separate devices solely for purposes of clarity. That is, the disclosed functionality of the data collection device 200 and the disclosed functionality of the metformin pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the metformin pharmaceutical composition OTC dispensing device 250 are contained in a single device.

With the integrated system 48, survey results from the subjects are run against a first plurality of filters (e.g., filter 216-1, filter 216-2, filter 216-4, etc.) When a filter in the first plurality of filters (e.g., filter 216) is fired for a respective subject, the respective subject is deemed not qualified for the metformin pharmaceutical composition. The survey results are also run against a second plurality of filters (e.g., filter 222-1, filter 222-2, filter 222-6, etc.) When a respective filter in the second plurality is fired for a respective subject, the respective subject is provided with a warning (e.g., filter warning 226) associated with the respective filter. In some embodiments the survey results are run against the first plurality of filters and the second plurality of filters concurrently. In some embodiments the survey results are run against the first plurality of filters and then against the second plurality of filters. The method enabled by the integrated system 48 proceeds to a fulfillment process when no filter in the first plurality fires and the subject has acknowledged, or otherwise successfully addressed, each warning associated with each filter in the second plurality of filters that fired. As part of the fulfillment process, the composition order is stored (e.g., in a user profile 234 associated with the subject to receive the drug), a drug facts label (e.g., drug facts label 230) for the metformin composition is communicated to the qualifying subject. Upon subject confirmation that the label has been read, authorization is granted to dispense the metformin composition.

Referring to FIG. 1, the metformin pharmaceutical composition OTC dispensing device 250 qualifies a subject for over-the-counter delivery of metformin pharmaceutical composition to lower blood sugar levels. To accomplish this, the data collection device 200, which is in electrical communication with the metformin pharmaceutical composition OTC dispensing device 250, receives survey results originating from one or more user devices 102 associated with corresponding subjects. In some embodiments, the data collection device 200 receives such survey results directly from the user devices 102. For instance, in some embodiments the data collection device 200 receives this data wirelessly through radio-frequency signals. In some embodiments, such signals are in accordance with an 802.11 (Wi-Fi), Bluetooth, or ZigBee standard. In some embodiments, the data collection device 200 receives such data directly, analyzes the data, and passes the analyzed data to the metformin pharmaceutical composition OTC dispensing device 250.

In some embodiments, the data collection device 200 and/or metformin pharmaceutical composition OTC dispensing device 250 is not proximate to the subject and/or does not have wireless capabilities or such wireless capabilities are not used for the purpose of acquiring survey results. In some embodiments, a communication network 106 may be used to survey questions (e.g., survey questions 208, 212) from the metformin pharmaceutical composition OTC dispensing device 250 to user devices 102 and the answers to such survey questions from the user devices 102 to the data collection device 200 and/or the metformin pharmaceutical composition OTC dispensing device 250. Further, in some embodiments the communication network 106 is used to communicate authorization to dispense the metformin composition survey questions from the metformin pharmaceutical composition OTC dispensing device 250 to dispensary destination devices 104.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the metformin pharmaceutical composition OTC dispensing device 250. Further, the data collection device 200 and/or the metformin pharmaceutical composition OTC dispensing device 250 may constitute a portable electronic device, a server computer, or in fact constitute several computers that are linked together in a network, be a virtual machine in a cloud computing context, be a container in a cloud computer context, or a combination thereof. As such, the exemplary topology shown in FIG. 1 merely serves to describe the features of an embodiment of the present disclosure in a manner that will be readily understood to one of skill in the art.

Figure 2:
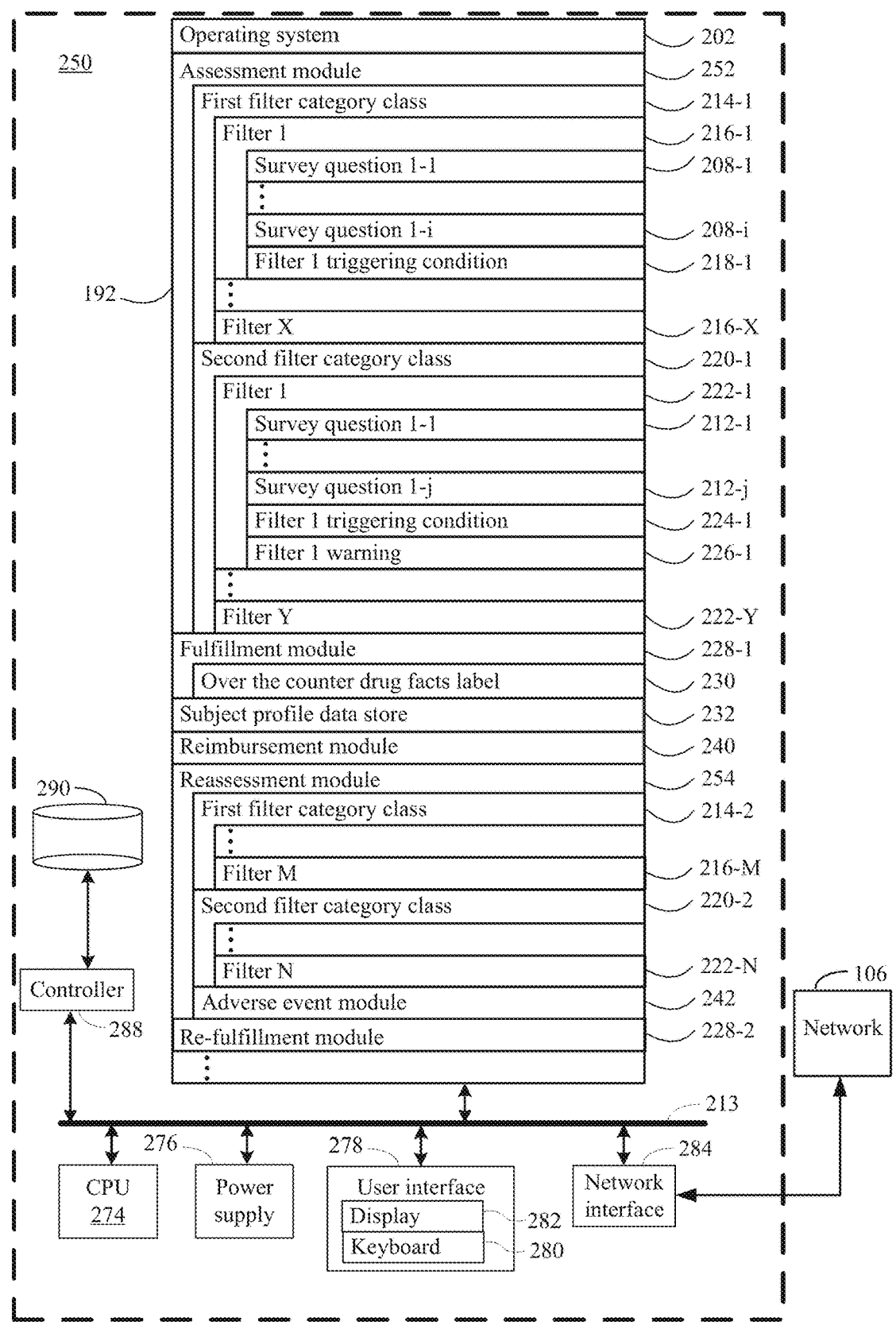
FIG. 2 illustrates an example device for qualifying a human subject for delivery of a metformin pharmaceutical composition over-the-counter to lower blood sugar levels, in accordance with various embodiments of the present disclosure.

Turning to FIG. 2 with the foregoing in mind, an exemplary metformin pharmaceutical composition OTC dispensing device 250 configured for determining whether a subject is qualified for OTC delivery of a metformin composition is depicted. Referring to FIG. 2, in typical embodiments, the metformin pharmaceutical composition OTC dispensing device 250 comprises one or more computers. For purposes of illustration in FIG. 2, the metformin pharmaceutical composition OTC dispensing device 250 is represented as a single computer that includes all of the functionality for qualifying a human subject for over-the-counter delivery of a metformin pharmaceutical composition to lower blood sugar levels. However, the present disclosure is not limited thereto. In some embodiments, the functionality for qualifying a human subject for over-the-counter delivery of a metformin pharmaceutical composition to lower blood sugar levels is spread across any number of networked computers and/or resides on each of several networked computers, is hosted on one or more virtual machines at a remote location accessible across the communications network 106, and/or is hosted on one or more containers at a remote location accessible across the communications network 106. One of skill in the art will appreciate that any of a wide array of different computer topologies are used for the application and all such topologies are within the scope of the present disclosure.

The metformin pharmaceutical composition OTC dispensing device 250 of FIG. 2 is configured to conduct a first survey (e.g., using assessment module 252 to perform an initial qualification of the subject for provision of a metformin pharmaceutical composition) and/or a second survey (e.g., using reassessment module 254 to perform a re-qualification of the subject for provision of a metformin pharmaceutical composition). The first survey (e.g., the assessment) comprises a variety of questions 208, 212 associated with filters 216, 222 within a plurality of filters of the first filter category class 214-1 and a plurality of filters in the second filter category class 220-1, respectively. Answers to the questions in the first survey received by the device are run against filters of a first category class 214 and filters of a second category class 220 within the first and second pluralities of filters 214-1, 216-1, respectively. Similarly, the second survey (e.g., the re-assessment) also comprises a variety of questions associated with filters 216, 222 within a plurality of filters of a first category class 214-2 and a plurality of filters of a second category class 220-2, respectively. Answers to the questions in the second survey received by the device are run against filters of a first category class 216-2 and filters of a second category class 220-2, e.g., within the first and second pluralities of filters, respectively. Filters 216 of the first filter category class 214 are configured to terminate the qualification process when fired. Filters 222 of the second filter category class 220 are configured to provide the subject with a warning associated with a corresponding survey question. In other words, the device of FIG. 2 is configured to accumulate results from a survey (e.g., survey questions 208 and survey questions 212) and run the results against corresponding filters (e.g., filters 216 and filters 222, respectively) in order to determine if a subject is qualified for OTC delivery of a metformin pharmaceutical composition.

In the present disclosure, a plurality of filters refers to a series, or set, or filters in either the first filter category class or the second category class. For instance, in some embodiments, a plurality of filters of the first filter category class 214 can comprise any subset of filters 216 of the first filter category class. As an example, in some embodiments a plurality of filters of the first category class comprises filters 216-1, 216-2, 216-3, . . . , 216-i, or any combination thereof. Similarly, a plurality of filters of the second filter category class 220 can comprise any set of filters 222 of the second filter category class. Moreover, in some embodiments a plurality of filters of the second category class comprises filters 222-1, 222-2, 222-3, . . . , 222-i, or any combination thereof.

Continuing to refer to FIG. 2, in some embodiments, the dispensing device 250 comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the metformin pharmaceutical composition OTC dispensing device 250 but that can be electronically accessed by the metformin pharmaceutical composition OTC dispensing device 250 over an Internet, intranet, or other form of network or electronic cable (illustrated as element 106 in FIG. 2) using network interface 284.

In some embodiments, the memory 192 of the metformin pharmaceutical composition OTC dispensing device 250 stores one or more of:

- an operating system 202 that includes procedures for handling various basic system services;
- an assessment module 252 for qualifying a subject for an initial over-the-counter delivery of a metformin pharmaceutical composition to lower blood sugar levels, e.g., thereby, treating Type 2 diabetes and/or maintaining sub-diabetic blood sugar levels, by communicating survey questions, obtaining results therefrom, and applying the results to qualifying filters, the assessment module including:
  - a first filter category class 214-1, including filters 216 (e.g., a first plurality of filters), each respective filter 216 in the first filter category class 214-1 associated with one or more survey questions 208 and one or more triggering conditions 218;
  - a second filter category class 220-1, including filters 222 (e.g., a second plurality of filters), each respective filter 222 in the second filter category class 220-1 associated with one or more survey questions 208, triggering conditions 224, and warnings 226;
- a fulfillment module 228-1 for executing a fulfillment process when no filter 216 in the first filter category class 214-1 has been fired for a subject and the subject has acknowledged each warning 226 associated with each filter 222 in the second filter category class 220-1 that was fired as a result of answers by the subject to the survey questions 208, where the fulfillment process includes communicating an over-the-counter drug facts label 230 for the metformin pharmaceutical composition to the subject and receiving confirmation from the subject that the over-the-counter drug facts label has been received and read;
- a reassessment module 254 for qualifying a subject for a subsequent over-the-counter delivery of a metformin pharmaceutical composition to lower blood sugar levels, e.g., thereby, treating Type 2 diabetes and/or maintaining sub-diabetic blood sugar levels, by communicating survey questions, obtaining results therefrom, and applying the results to qualifying filters, the assessment module including:
  - a first filter category class 214-2, including filters 216 (e.g., a third plurality of filters), each respective filter 216 in the first filter category class 214-2 associated with one or more survey questions 208 and one or more triggering conditions 218;
  - a second filter category class 220-2, including filters 222 (e.g., a second plurality of filters), each respective filter 222 in the second filter category class 220-2 associated with one or more survey questions 208, triggering conditions 224, and warnings 226;
- a re-fulfillment module 228-2 for executing a re-fulfillment process when no filter 216 in the first filter category class 214-2 has been fired for a subject and the subject has acknowledged each warning 226 associated with each filter 222-2 in the second filter category class 220 that was fired as a result of answers by the subject to the survey questions 212, where the re-fulfillment process includes communicating an over-the-counter drug facts label 230 for the metformin pharmaceutical composition to the subject and receiving confirmation from the subject that the over-the-counter drug facts label has been received and read;
- a subject profile data store 232 comprising a user profile 234 for each of a plurality of subjects, each respective user profile 234 including information (e.g., shipping information, billing information, biometric information, etc.) about a corresponding subject in the plurality of subjects, an initial order date and destination 236, and any re-order date and the destination 238 for the metformin pharmaceutical composition made by the corresponding subject using the metformin pharmaceutical composition OTC dispensing device 250;
- an adverse event module 242 for identifying and aggregating records of adverse events associated with a plurality of subjects, e.g., corresponding to the firing of a filter 216 in the first filter category class 214-2 during a re-fulfillment process;
- a reimbursement module 240 for determining eligibility and/or communicating an insurance claim associated with delivery of the metformin composition, e.g., based on insurance information stored in a respective user profile 234.

In some embodiments, the assessment module 252, reassessment module 254, and/or fulfillment module 228 are accessible within any browser (e.g., phone, tablet, laptop/desktop, or smartwatch). In some embodiments the assessment module 252, reassessment module 254, and/or fulfillment module 228 run on native device frameworks, and is available for download onto a user device 102 running an operating system 202 such as Android, iOS, or WINDOWS.

In some implementations, one or more of the above identified data elements or modules (e.g., assessment module 252, fulfillment module 228-1, etc.) of the metformin pharmaceutical composition OTC dispensing device 250 for qualifying a human subject for over-the-counter delivery of a metformin pharmaceutical composition to lower blood sugar levels are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a metformin pharmaceutical composition OTC dispensing device 250 for qualifying a human subject for over-the-counter delivery of a metformin pharmaceutical composition to lower blood sugar levels is a smart phone (e.g., an iPhone, Blackberry, etc.), a laptop, a tablet computer, a desktop computer, a smart watch, or another form of electronic device (e.g., a gaming console). In some embodiments, the metformin pharmaceutical composition OTC dispensing device 250 is not mobile. In some embodiments, the metformin pharmaceutical composition OTC dispensing device 250 is mobile.

In some embodiments, the metformin pharmaceutical composition OTC dispensing device 250 is not a smart phone but rather is a tablet computer, desktop computer, emergency vehicle computer, or other form or wired or wireless networked device. In the interest of brevity and clarity, only a few of the possible components of the metformin pharmaceutical composition OTC dispensing device 250 are shown in FIG. 2 in order to better emphasize the additional software modules that are installed on the metformin composition OTC dispensing device 250.

Figure 3A:
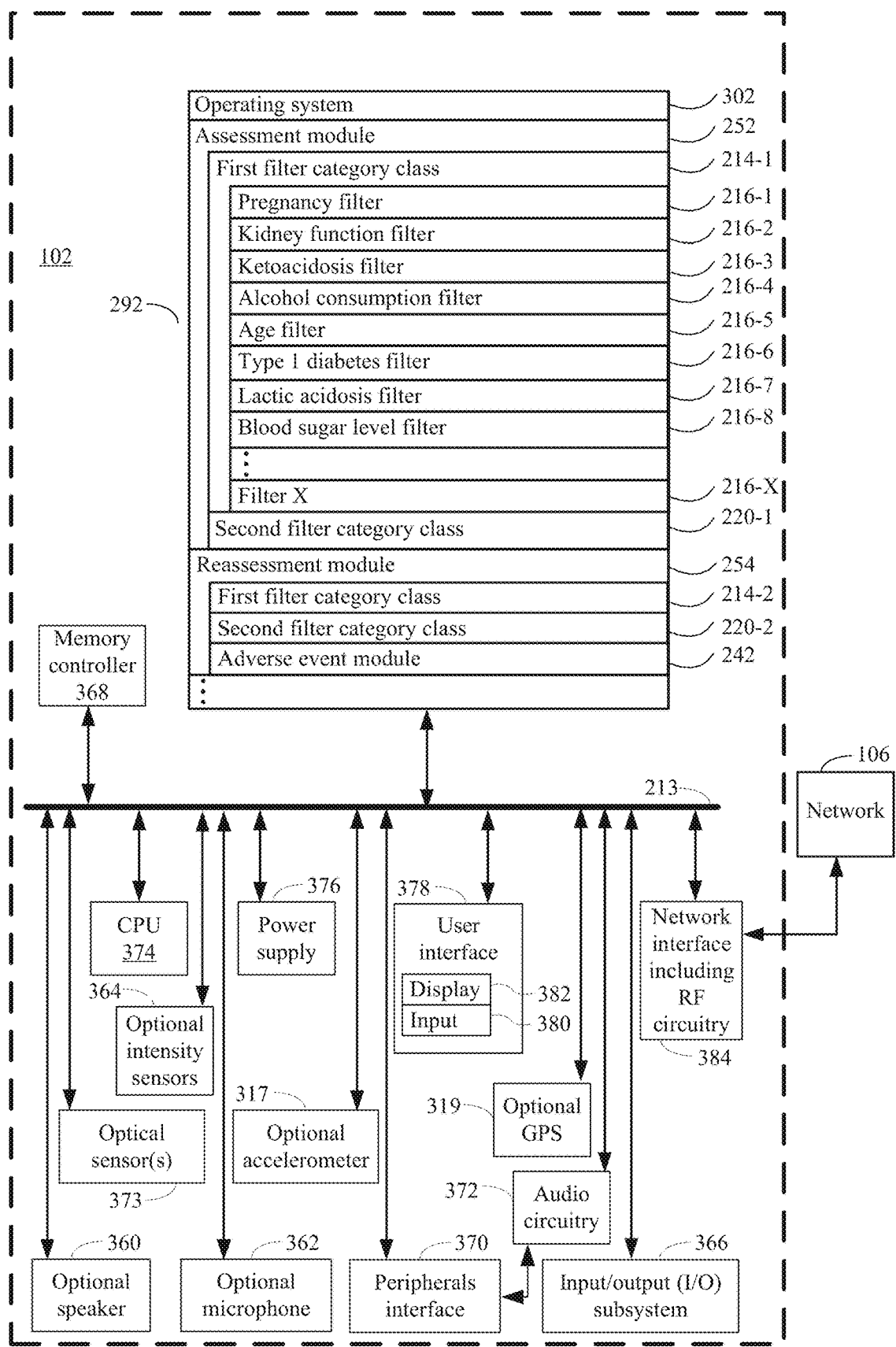
FIGS. 3A, 3B, and 3C collectively illustrate an example device associated with a human subject for qualifying the human subject for over-the-counter delivery of a metformin pharmaceutical composition to treat or prevent symptoms of asthma, in accordance with an embodiment of the present disclosure, where it will be appreciated that the example device of FIGS. 3A, 3B, and 3C works in conjunction with the device of FIG. 2 to perform the methods illustrated in FIGS. 4 through 8 in some embodiments by, for instance providing the device of FIG. 2 with survey results and/or the results of firing filters of the present disclosure against such survey results but that, in alternative embodiments, the device of FIG. 2 performs all the methods of the present disclosure and the device of FIGS. 3A, 3B, and 3C is not used. In still further alternative embodiments, the device of FIGS. 3A, 3B, and 3C performs the methods of the present disclosure and the device of FIG. 2 is not used.
Figure 3B:
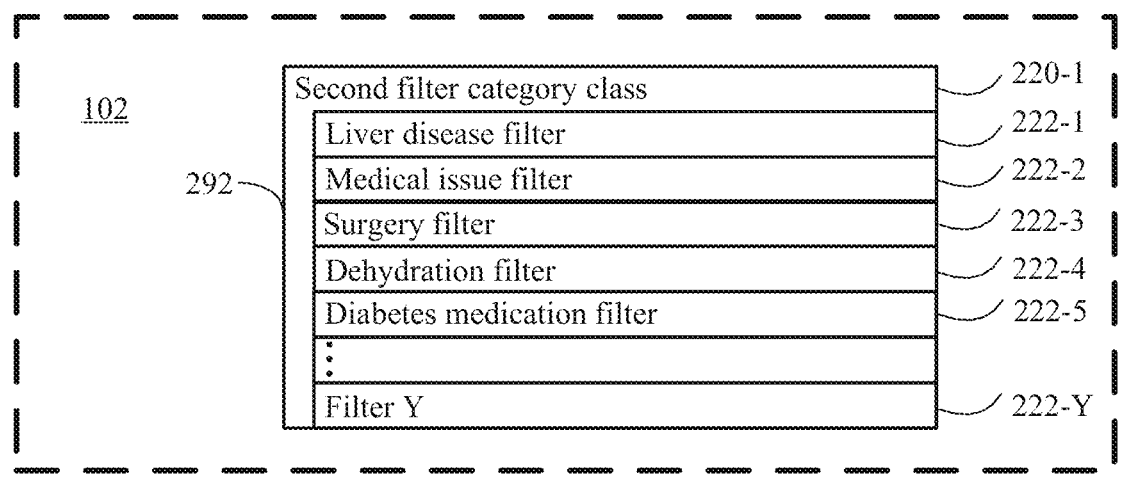
Figure 3C:
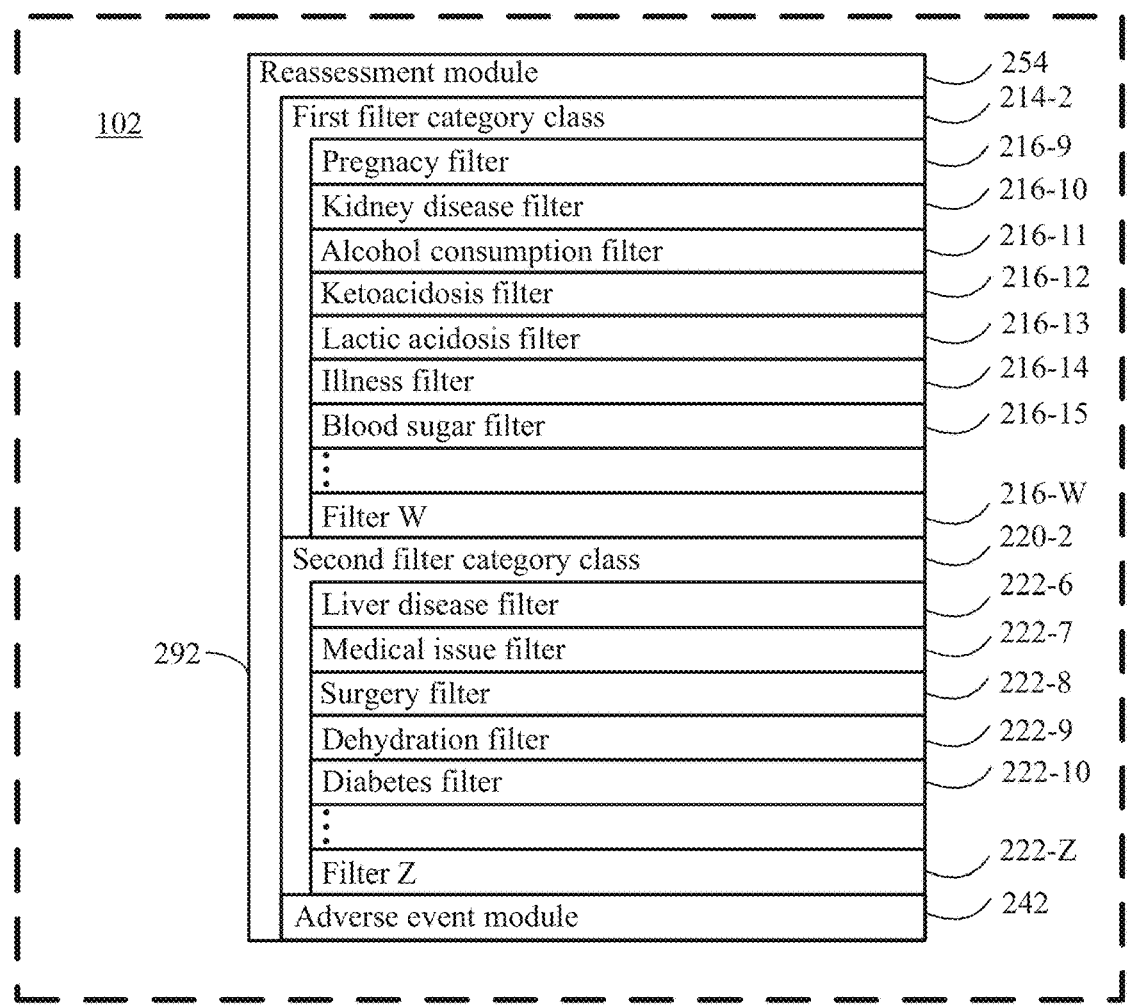

FIG. 3 provides a description of a user device 102 that can be used with the present disclosure. The user device 102 illustrated in FIG. 3 has one or more processing units (CPU's) 374, peripherals interface 370, memory controller 368, a network or other communications interface 384, a memory 392 (e.g., random access memory), a user interface 378, the user interface 378 including a display 382 and input 380 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 382 of the user device 102), an optional input/output (I/O) subsystem 366, one or more optional optical sensors 373, one or more communication busses 313 for interconnecting the aforementioned components, and a power supply 376 for powering the aforementioned components.

In some embodiments, the input 380 is a touch-sensitive display, such as a touch-sensitive surface. In some embodiments, the user interface 378 includes one or more soft keyboard embodiments. The soft keyboard embodiments may include standard (e.g., QWERTY) and/or non-standard configurations of symbols on the displayed icons.

The user device 102 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the user device 102 and/or for determining an amount of physical exertion by the subject.

It should be appreciated that the user device 102 illustrated in FIG. 3 is only one example of a multifunction device that may be used for performing a survey (e.g., first survey 206) in order to qualify for over-the-counter delivery of a metformin pharmaceutical composition to lower blood sugar levels, and that the user device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 392 of the user device 102 illustrated in FIG. 3 optionally includes high-speed random access memory and optionally also includes non-volatile memory, such as one or more magnetic disk storage devices, flash memory devices, or other non-volatile solid-state memory devices. Access to memory 392 by other components of the metformin pharmaceutical composition OTC dispensing device 250, such as CPU(s) 374 is, optionally, controlled by the memory controller 368. In some embodiments, the memory 392 of the user device 102 illustrated in FIG. 3 optionally includes:

- an operating system 302 that includes procedures for handling various basic system services;
- the assessment module 252 described above in conjunction with the metformin pharmaceutical composition OTC dispensing device 250;
- the first category class 214 described above in conjunction with the metformin pharmaceutical composition OTC dispensing device 250 further comprising a pregnancy filter 216-1, a kidney function filter 216-2, a ketoacidosis filter 216-3, an alcohol consumption filter 216-4, an age filter 216-5, a Type 1 diabetes filter 216-6, a lactic acidosis filter 216-7, and a blood sugar level filter 216-8; and
- the second category class 220 described above in conjunction with the metformin pharmaceutical composition OTC dispensing device 250 comprising a liver disease filter 222-1, medical issue filter 222-2, a surgery 222-3, a dehydration filter 222-4, and a diabetes medication filter 222-5;

In some embodiments, the optional accelerometer 317, optional GPS 319, and/or magnetometer (not shown) of the user device 102 or such components are used to recommend to qualifying subjects one or more suitable destinations for delivery of the metformin pharmaceutical composition over-the-counter. In some embodiments, the GPS 319 is used to determine if a subject is geographically restricted for OTC delivery of the metformin pharmaceutical composition. Geographical restrictions include but are not limited to a subject residing outside of delivery or shipping regions, marketing restrictions, and/or government regulations.

The peripherals interface 370 can be used to couple input and output peripherals of the device to CPU(s) 374 and memory 392. The one or more processors 374 run or execute various software programs and/or sets of instructions stored in memory 392, such as the survey module 204, to perform various functions for the user device 102 and to process data.

In some embodiments, the peripherals interface 370, CPU(s) 374, and memory controller 368 are, optionally, implemented on a single chip. In some other embodiments, they are implemented on separate chips.

RF (radio frequency) circuitry of network interface 384 receives and sends RF signals, also called electromagnetic signals. In some embodiments, the survey module 204, survey questions 208/212, answers to survey questions 208/212, and/or the over-the-counter drug facts label 230 are communicated to the subject device 102 using this RF circuitry. In some embodiments, the RF circuitry 384 converts electrical signals to/from electromagnetic signals and communicates with communications networks and other communications devices and/or the data collection device 200 and/or the metformin pharmaceutical composition OTC dispensing device 250 via the electromagnetic signals. The RF circuitry 384 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 384 optionally communicates with the communication network 106. In some embodiments, the circuitry 384 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. In some embodiments, the speaker 260 converts the electrical signals to human-inaudible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 392 and/or the RF circuitry 384 by the peripherals interface 370.

In some embodiments, the power supply 376 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 382 on the front of the user device 102, so that the input 380 is enabled for use as a viewfinder for still and/or video image acquisition. In some embodiments, another optical sensor 373 is located on the front of the user device 102 so that the subject's image is obtained (e.g., to verify the health, condition, or identity of the subject as part of qualifying the subject for over-the-counter delivery of a metformin pharmaceutical composition to lower blood sugar levels), to help diagnose a subject's condition remotely, or to acquire visual physiological measurements of the subject, etc.).

As illustrated in FIG. 3, the user device 102 preferably comprises an operating system 302 that includes procedures for handling various basic system services. The operating system 302 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the user device 102 is a smart phone or a smart watch. In other embodiments, the user device 102 is not a smart phone or a smart watch but rather is a tablet computer, a desktop computer, an emergency vehicle computer, or other form or wired or wireless networked device. In the interest of brevity and clarity, only a few of the possible components of the user device 102 are shown in FIG. 3 in order to better emphasize the additional software modules that are installed on the user device 102.

While the system 48 disclosed in FIG. 1 can work standalone, in some embodiments it can also be linked with electronic medical record systems to exchange information in any way.

Now that details of a system 48 for qualifying a human subject for over-the-counter delivery of a metformin composition to lower blood sugar levels have been disclosed, details regarding method (400), including processes and features to be performed by the system, in accordance with an embodiment of the present disclosure, are disclosed with reference to FIGS. 4A through 4I. In some embodiments, such processes and features of the system are carried out by the assessment module 252, reassessment module 254, fulfillment module 228-1, and/or re-fulfillment module 228-2 illustrated in FIGS. 2 and 3. In some embodiments, the assessment module 252, reassessment module 254, fulfillment module 228-1, and/or re-fulfillment module 228-1 are a single software module. In the flow chart, elements in dashed boxes are considered to be optional.

Blocks 402-406.

Referring to block 402 of FIG. 4A, a goal of the present disclosure is to qualify subjects for over-the-counter delivery of a metformin pharmaceutical composition to lower blood sugar levels, e.g., thereby, treating Type 2 diabetes and/or maintaining sub-diabetic blood sugar levels using a computer system such as a metformin pharmaceutical composition OTC dispensing device 250. The metformin pharmaceutical composition OTC dispensing device (e.g., device 250) comprises one or more processors (e.g., processor 274) and a memory (e.g., memory 192 and/or 290). The memory stores non-transitory instructions that, when executed by the one or more processors, perform a method.

Referring to block 404, in some embodiments the metformin pharmaceutical composition is (e.g., an extended release formulation) metformin hydrochloride.

In some embodiments, the metformin pharmaceutical composition includes any compound disclosed in U.S. Pat. No. 6,031,004, entitled "Salts of Metformin and Method," which is hereby incorporated by reference. In some embodiments, the metformin pharmaceutical composition comprises any compound disclosed in U.S. Pat. No. 5,952,356, entitled "Pharmaceutical Composition," which is hereby incorporated by reference. In some embodiments, the metformin pharmaceutical composition comprises any compound disclosed in U.S. Pat. No. 6,866,866, entitled "Controlled Release Metformin Compositions," which is hereby incorporated by reference.

Referring to block 406, in some embodiments, the lowering of blood sugar levels is to treat Type 2 diabetes. Typically, this is accomplished by a suppression of liver glucose production.

In some embodiments, in response to receiving a first request from a user to be qualified for provision of a metformin pharmaceutical composition, the system creates a corresponding subject profile, e.g., containing biographic information about the subject, e.g., one or more of a subject name, date of birth, residence, delivery address, social security number, medical record number, insurance information, user name, identification password, etc. In some embodiments, the system registers a subject that has not previously received an over-the-counter provision of a metformin pharmaceutical composition as a new user of the metformin pharmaceutical composition, and the device will perform an initial assessment method for qualifying the subject for a provision of the metformin pharmaceutical composition, e.g., regardless of whether the subject previously received a provision of a metformin pharmaceutical composition via prescription.

In some embodiments, the system registers a subject that has previously received a provision of a metformin pharmaceutical composition via prescription as a previous user of the metformin pharmaceutical composition, and the device will perform a reassessment method for re-qualifying the subject for a provision of the metformin pharmaceutical composition.

In some embodiments, where the subject previously received a provision of a different metformin pharmaceutical composition via prescription, the system will perform a modified method for qualifying the subject for provision of the metformin pharmaceutical composition that accounts for differences in the contraindications and risk factors of the two metformin pharmaceutical compositions.

In some embodiments, in response to receiving a second or subsequent request from a user to be qualified for provision of a metformin pharmaceutical composition, the system registers the subject as a returning customer, e.g., when the subject has previously received an over-the-counter provision of the metformin and a corresponding subject profile 232 already exists for the subject.

Figure 7A:
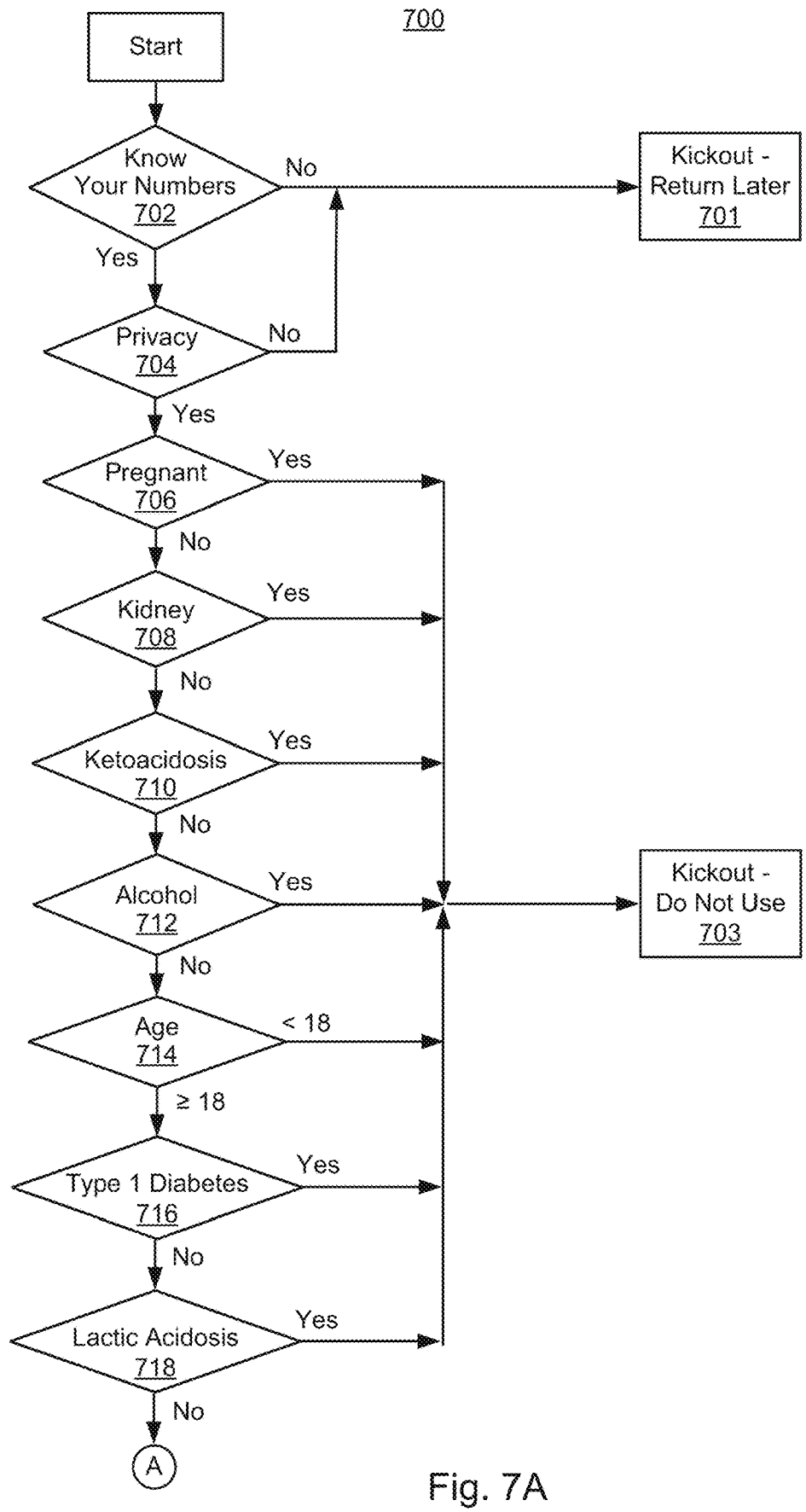
FIGS. 7A, 7B, and 7C collectively illustrate an example method for qualifying a subject for an over-the-counter provision of a metformin pharmaceutical composition, in accordance with an embodiment of the present disclosure.

In some embodiments, prior to proceeding with the qualification or re-qualification method, the device prompts (702, 704) the user to confirm that they have adequate privacy to provide sensitive medical information (e.g., prompt 704 in FIG. 7A) and/or that they are in possession of medical information required to complete the qualification process (e.g., prompt (704) to confirm that they have knowledge of their blood sugar levels, in FIG. 7A).

Blocks 408.

Referring to block 408 of FIG. 4A, the method includes conducting a first survey of the subject thereby obtaining a first plurality of survey results (e.g., in response to survey questions 208, 212 (e.g., one or more of the survey questions set forth in Table 1). In some embodiments, the device transmits one or more survey questions to the user, prompting a response, and then receives a response to the one or more survey questions back from the subject. In some embodiments, the first survey results include, or at least indicate, some or all of the subject characteristics listed in Table 1. For example, in some embodiments, the first plurality of survey results includes, or at least indicates, 2, 3, 4, 5, 6, 7, 8, 9, 10, 11, 12, 13, or all 14 of the characteristics listed in Table 1. In one embodiment, the first survey questions 208, 212 and results include at least characteristics 1-13 as provided in Table 1.

Figure 5C:
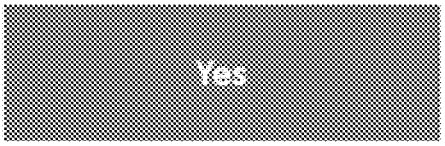
Figure 5C:
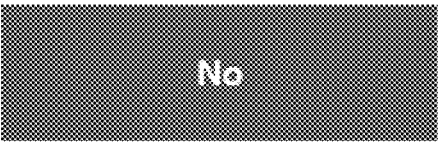
Figure 5D:
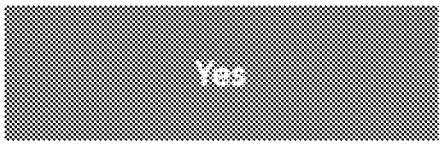
Figure 5D:
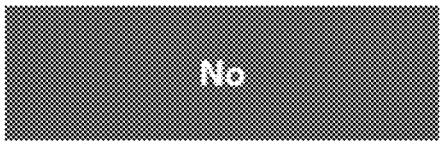

Referring to block 410, e.g., as illustrated in FIG. 7, in some embodiments the first survey results indicate whether the subject is one of pregnant, breastfeeding, or planning to become pregnant (e.g., responsive to a survey question 208, such as question 550 such as the one illustrated in FIG. 5A, e.g., that is associated with and/or applied to (706) a pregnancy filter 216-1 of a first category class), whether the subject has a kidney problem (e.g., responsive to a survey question 208 that is associated with and/or applied to (708) a kidney function filter 216-2 of a first category class), a ketoacidosis status of the subject (e.g., responsive to a survey question 208 that is associated with and/or applied to (710) a ketoacidosis filter 216-3 of a first category class), an alcohol consumption status of the subject (e.g., responsive to a survey question 208 that is associated with and/or applied to (712) an alcohol filter 216-4 of a first category class), an age of the subject (e.g., responsive to a survey question 208 that is associated with and/or applied to (714) an age filter 216-5 of a first category class), a Type 1 diabetes status of the subject (e.g., responsive to a survey question 208 that is associated with and/or applied to (716) a Type 1 diabetes filter 216-6 of a first category class), a lactic acidosis status of the subject (e.g., responsive to a survey question 208 that is associated with and/or applied to (718) a lactic acidosis filter 216-7 of a first filter class category), a blood sugar level of the subject (e.g., responsive to a survey question 208 that is associated with and/or applied to (720) a blood sugar level filter 216-8 of a first category class), whether the subject has a liver problem (e.g., responsive to a survey question 212 that is associated with and/or applied to (722) a liver disease filter 222-1 of a second category class), whether the subject has ever had a heart attack, severe infection, or stroke (e.g., responsive to a survey question 212 that is associated with and/or applied to (724) a medical issue filter 222-2 of a second category class), a surgery status of the subject (e.g., responsive to a survey question 212 that is associated with and/or applied to (726) a surgery filter 222-3 of a second category class), whether the subject has a history of dehydration (e.g., responsive to a survey question 212 that is associated with and/or applied to (728) a dehydration filter 222-4 of a second category class), and whether the subject is already taking a diabetes medication, (e.g., responsive to a survey question 212 that is associated with and/or applied to (730) a diabetes medication filter 222-5 of a second category class).

In some embodiments, the first survey includes questions that elicit responses providing or indicating some or all of the characteristics listed in Table 1. In some embodiments, the survey includes questions corresponding to each of the survey results required for the methods described herein. In other embodiments, the survey includes questions corresponding to only a subset of the survey results required for the methods described herein. In some embodiments, other survey results required for the methods described herein are acquired through other means (e.g., upon registration/subscription for a service associated with qualifying the subject for over-the-counter medication, from a healthcare provider, from a prior survey, from a database associated with a pharmacy, from an electronic health record associated with the subject, from the subject profile data store 232, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a last blood sugar level measurement determined for the subject).

TABLE 1

Example subject characteristics for qualifying a subject for an over-the-counter provision of a metformin pharmaceutical composition

| Result | Example Characteristics |
|---|---|
| 1 | whether the subject is one of pregnant, breastfeeding, or planning to become pregnant |
| 2 | whether the subject has a kidney problem |
| 3 | a ketoacidosis status of the subject |
| 4 | an alcohol consumption status of the subject |
| 5 | an age of the subject |

TABLE 1-continued

Example subject characteristics for qualifying a subject for an over-the-counter provision of a metformin pharmaceutical composition

| Result | Example Characteristics |
|---|---|
| 6 | a Type 1 diabetes status of the subject |
| 7 | a lactic acidosis status of the subject |
| 8 | a blood sugar level of the subject |
| 9 | whether the subject has a liver problem |
| 10 | whether the subject has ever had a heart attack, severe infection, or stroke |
| 11 | a surgery status of the subject |
| 12 | whether the subject has a history of dehydration |
| 13 | whether the subject is taking a diabetes medication |
| 14 | whether the subject is allergic to the metformin pharmaceutical composition |

It is contemplated that, in some embodiments, any one or more of the survey questions 208, 212 provided in Table 1 will not be included in the first survey (e.g., will not be used for the assessment). For example, in some embodiments, a characteristic associated with a particular survey questions will be informative when qualifying a subject for one particular metformin composition but not for another metformin composition.

Accordingly, it is contemplated that the first survey questions 208 include any subset of survey results provided in Table 1. For brevity, all possible combinations of survey questions 208, 212 eliciting the characteristics provided in Table 1 are not specifically delineated here. However, the skilled artisan will easily be able to envision any particular subset of the survey questions 208, 212 that elicit the characteristics provided in Table 1. Likewise, the skilled artisan may know of other survey questions, eliciting informative subject characteristics not provided in Table 1, that may be combined with any subset of survey questions that elicit subject characteristics provided in Table 1 to form the first survey questions used in the methods described herein.

In some embodiments, the first and/or second survey is conducted by transmitting a plurality of questions to the subject, e.g., some or all of the survey questions, and receiving answers to the plurality of survey questions before applying any of the answers to respective filters. For example, with reference to the workflow in FIG. 7, the device transmits questions relating to all of the filters of the first category class, all of the filters of the second category class, or all of the filters in the workflow (e.g., as a virtual survey where all of the questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the metformin pharmaceutical composition. In alternative embodiments, the device transmits questions relating to just those filters of the first category class for which it could not obtain answers to the questions from an electronic database associated with the subject, such as electronic health record of the subject, and just those filters of the second category class it could not obtain answers to the questions from an electronic database associated with the subject (e.g., as a virtual survey where such unanswered questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the metformin pharmaceutical composition.

Figure 7B:
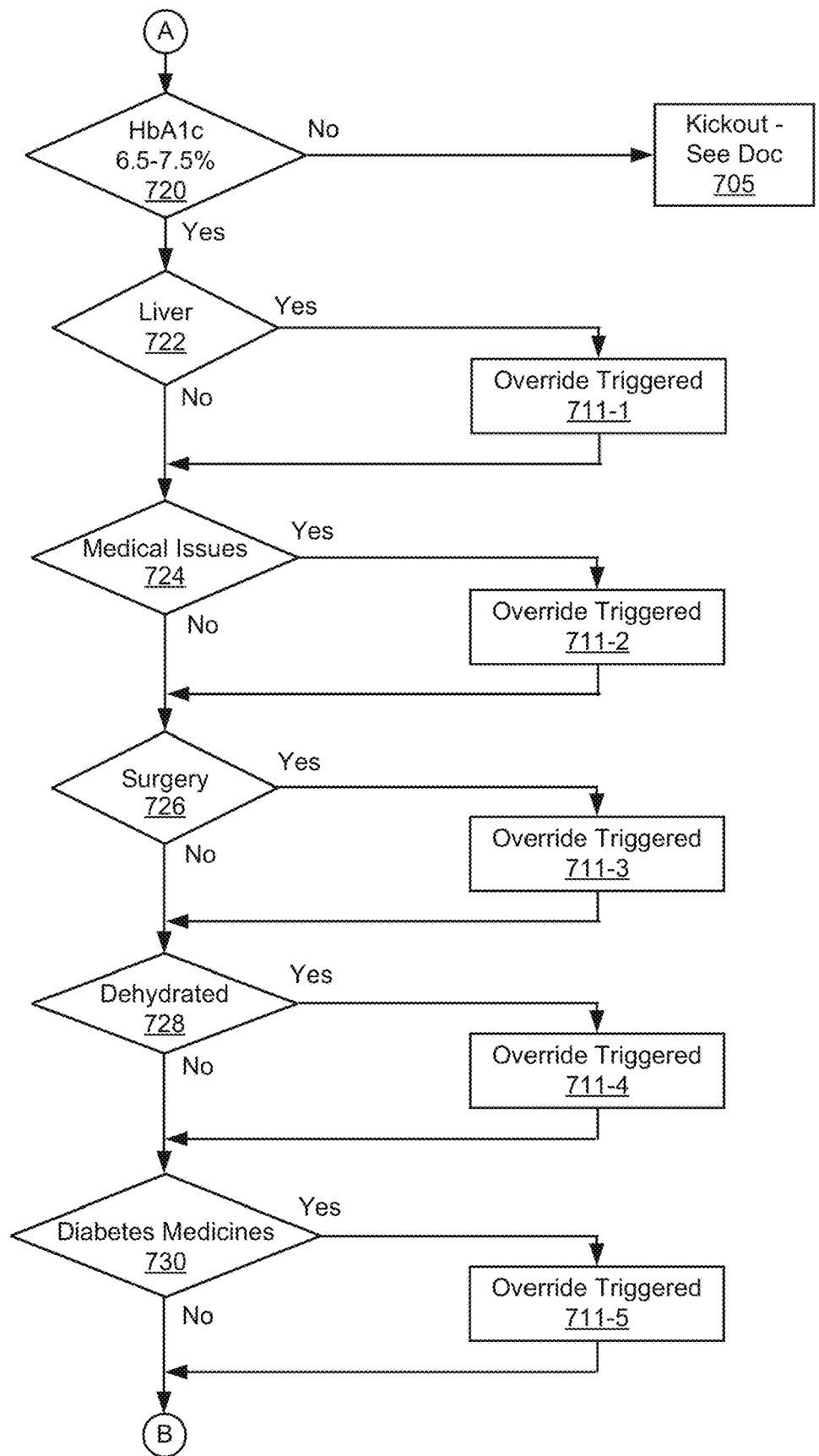

In some embodiments, the first and/or second survey is conducted in a serial fashion, e.g., by transmitting a first question or a first group of survey questions (e.g., associated with a single filter) to the subject, receiving an answer to the single survey question or small group of survey questions, and applying the answer or answers to a filter, prior to transmitting a second question or second group of questions to the subject. For example, with reference to the workflow in FIG. 7, in some embodiments the device transmits a first question to the subject, relating to the pregnancy and/or breastfeeding status of the subject (e.g., question 502 'Are you or do you plan to become pregnant? Are you breastfeeding or planning to breastfeed?' in FIG. 5A). After receiving the answer to the survey question (e.g., 'yes or no'), the device applies the answer to a first pregnancy filter (706). If the first pregnancy filter is fired (e.g., in response to a "yes" answer), the device terminates (701) the process, and optionally provides the user with a message relating to why they are being denied a provision of the metformin pharmaceutical composition (e.g., as illustrated in FIG. 5B, message 552, advising the subject that taking the metformin pharmaceutical composition creates a risk for the fetus/baby), a suggestion for following-up with a medical professional (e.g., as illustrated in FIG. 7B, when the survey answers indicate that the subject is in diabetic crisis (720), the device terminates the process (705) and advises that the subject seek immediate medical attention or visit a medical professional), and/or a suggestion to make a lifestyle change, to treat or manage their blood sugar levels.

Blocks 412-440.

Referring to block 412 of FIG. 4B, all or a portion of the first survey results are run against a first plurality of filters of a first category class 214. As previously described, the first plurality of filters includes a subset of filters 216 of the first filter category class 214. When a respective filter in the first plurality of filters is fired (e.g., when a survey result indicates that a triggering condition 218 has been met), the subject is deemed not qualified for delivery of the metformin pharmaceutical composition and the method is terminated without delivery of the metformin pharmaceutical composition.

In some embodiments, e.g., when the method is terminated without delivery of the metformin pharmaceutical composition, the subject is prevented from attempting to requalify for the metformin composition for a predetermined period of time (e.g., the subject is locked out). In some embodiments, the subject is prevented from attempting to requalify for the metformin composition after a predetermined number of qualification attempts. In some embodiments, the subject is prevented from attempting to requalify for the metformin composition after a failing to verify a communication (e.g., failing to verify a text message sent to the subject). This prevents the subject from abusing the systems and methods of the present disclosure.

Referring to blocks 414-440, specific filters 216 in the first plurality of filters and their exemplary triggering conditions 218 that cause the corresponding filter to fire are detailed.

In some embodiments, the first plurality of filters of the first category class 214 includes some or all of the filters 216 listed in Table 2. For example, in some embodiments, the first plurality of filters results includes 2, 3, 4, or all 5 of the filters listed in Table 2.

TABLE 2

Example filters for contraindications associated with qualifying a subject for an over-the-counter provision of a metformin pharmaceutical composition

| Filter | Example Criteria |
|---|---|
| 1a | a pregnancy filter |
| 2a | a kidney function filter |
| 3a | a ketoacidosis filter |
| 4a | an alcohol consumption filter |
| 5a | an age filter |
| 6a | a Type 1 diabetes filter |
| 7a | a lactic acidosis filter |
| 8a | a blood sugar level filter |

It is contemplated that, in some embodiments, any one or more of the filters 216 provided in Table 2 will not be included in the first plurality of filters. For example, in some embodiments, a characteristic associated with a particular survey result will be informative when qualifying a subject for one particular metformin composition but not for another metformin composition.

Accordingly, it is contemplated that the first plurality of filters includes any sub-set of filters 216 provided in Table 2. Likewise, the skilled artisan may know of other filters 216, not provided in Table 2, which may be combined with any subset of the filters 216 provided in Table 2 to form the first plurality of filters results used in the methods described herein. For brevity, all possible combinations of the filters 216 provided in Table 2 are not specifically delineated here.

Referring to blocks 414-416, in some embodiments the first plurality of filters includes a pregnancy filter (e.g., pregnancy filter 216-1 in FIG. 3 and/or filter 1a in Table 2). In some embodiments, the pregnancy filter is configured to be fired at least when the first plurality of survey results indicates that the subject is pregnant or the subject is breastfeeding. In some embodiments, the pregnancy filter is also configured to be fired when the subject is planning on becoming pregnant. When the pregnancy filter is fired, the subject is not permitted to obtain the metformin pharmaceutical composition over-the-counter (e.g., the method is terminated without authorizing provision of the metformin pharmaceutical composition to the subject). For example, the device transmits prompt 502, as illustrated in FIG. 5A, to the subject and the device applies the subject's answer to the pregnancy filter. If the subject's answer indicates that they are pregnant, they are planning on being pregnant, they are breastfeeding, or they are planning to breastfeeding, the pregnancy filter is fired, and the method is terminated without authorizing provision of the metformin pharmaceutical composition to the subject. In some embodiments, the device transmits a message explaining why authorization was denied, e.g., message 552 illustrated in FIG. 5B.

Referring to block 418, in some embodiments the first plurality of filters includes a kidney function filter (e.g., kidney function filter 216-2 in FIG. 3 and/or filter 2a in Table 2). The kidney function filter is configured to be fired at least when the first plurality of survey results indicates that the subject has a kidney problem. In some embodiments, symptoms of kidney problems which are capable of firing the kidney function filter include nausea, loss of appetite, and/or fatigue. In some embodiments, the kidney function filter is configured to be fired at least when the first plurality of survey results indicates that the subject has a kidney function below a floor kidney function level. In some embodiments, the floor kidney level function is 30 mL/min/1.73 m$^2$. In some embodiments, the floor kidney level function is 45 mL/min/1.73 m$^2$. If the kidney function filter is fired, the subject is not permitted to obtain the metformin pharmaceutical composition pharmaceutical composition over-the-counter (e.g., the method is terminated without authorizing provision of the metformin pharmaceutical composition to the subject).

Referring to block 420, in some embodiments the first plurality of filters includes a ketoacidosis filter (e.g., ketoacidosis filter 216-3 in FIG. 3 and/or filter 3a in Table 2). The ketoacidosis filter is configured to be fired at least when the first plurality of survey results indicates that the subject has ketoacidosis. If the ketoacidosis filter is fired, the subject is not permitted to obtain the metformin pharmaceutical composition over-the-counter (e.g., the method is terminated without authorizing provision of the metformin pharmaceutical composition to the subject).

Referring to blocks 422-424, in some embodiments the first plurality of filters includes an alcohol consumption filter (e.g., first alcohol consumption filter 216-4 in FIG. 3 and/or filter 4a in Table 2). In some embodiments, the alcohol consumption filter is configured to be fired when the first plurality of survey results indicates that the subject drinks alcohol very often, e.g., on average consumes at least a predetermined number of alcoholic drinks over a predetermined period of time. In some embodiments, the predetermined number of alcoholic drinks over a predetermined period of time is at least one alcoholic drink per day, at least two alcoholic drinks per day, at least three alcoholic drinks per day, or four or more alcoholic drinks per day. In some embodiments, the predetermined number of alcoholic drinks over a predetermined period of time is at least four, five, six, seven, eight, nine, ten, or more drinks per week. In some embodiments, the alcohol consumption filter is configured to be fired when the first plurality of survey results indicates that the subject has a history of binge drinking, e.g., drinking a lot of alcohol in a short time. If the alcohol consumption filter is fired, the subject is not permitted to obtain the metformin pharmaceutical composition over-the-counter (e.g., the method is terminated without authorizing provision of the metformin pharmaceutical composition to the subject).

Referring to blocks 426-428, in some embodiments the first plurality of filters includes an age filter (e.g., age filter 216-4 in FIG. 3 and/or filter 4a in Table 2). In some embodiments, the age filter is fired when the first plurality of survey results indicates that the subject has not yet reached an age of majority, e.g., is less than eighteen years old. If the age filter is fired, the subject is not permitted to obtain the metformin pharmaceutical composition pharmaceutical composition over-the-counter (e.g., the method is terminated without authorizing provision of the metformin pharmaceutical composition to the subject).

Referring to block 430, in some embodiments the first plurality of filters includes a Type 1 diabetes filter (e.g., Type 1 diabetes filter 216-5 in FIG. 3 and/or filter 5a in Table 2). The Type 1 diabetes filter is configured to be fired at least when the first plurality of survey results indicates that the subject has Type 1 diabetes. If the Type 1 diabetes filter is fired, the subject is not permitted to obtain the metformin pharmaceutical composition over-the-counter (e.g., the method is terminated without authorizing provision of the metformin pharmaceutical composition to the subject).

Referring to block 432, in some embodiments the first plurality of filters includes a lactic acidosis filter (e.g., lactic acidosis filter 216-6 in FIG. 3 and/or filter 6a in Table 2). The lactic acidosis filter is configured to be fired at least when the first plurality of survey results indicates that the subject has lactic acidosis. If the lactic acidosis filter is fired, the subject is not permitted to obtain the metformin pharmaceutical composition over-the-counter (e.g., the method is terminated without authorizing provision of the metformin pharmaceutical composition to the subject).

Referring to blocks 434-426, in some embodiments the first plurality of filters includes a blood sugar level filter (e.g., blood sugar level filter 216-7 in FIG. 3 and/or filter 7a in Table 2). The blood sugar level filter is configured to be fired at least when the first plurality of survey results indicates that the subject does not have a moderately elevated blood sugar level, e.g., a blood sugar level that is either below a first floor blood sugar level (e.g., in a normal range that does not warrant treatment with a metformin containing composition), or above a ceiling blood sugar level (e.g., in a highly elevated range that warrants treatment with a stronger, prescription medication). In some embodiments, the first floor blood sugar level used in the first blood sugar level filter is 6.5% glycated hemoglobin. In some embodiments, the ceiling blood sugar level used in the first blood sugar level filter is 7.5% glycated hemoglobin. In some embodiments, other blood sugar measurements, such as fasting plasma glucose, can be used to evaluate whether the subject should be qualified for a provision of the metformin pharmaceutical composition. Correlations between glycated hemoglobin and fasting plasma glucose levels have been described in the art, for example, in Nathan D M, et al., Diabetes Care, 31(8):1473-8 (2008), which is incorporated by reference herein. If the blood sugar level filter is fired, the subject is not permitted to obtain the metformin pharmaceutical composition over-the-counter (e.g., the method is terminated without authorizing provision of the metformin pharmaceutical composition to the subject).

In some embodiments, the blood sugar level cutoffs (e.g., floor and ceiling) defining when the blood sugar level filter is fired and when the blood sugar level filter is not fired are set according to a set of healthcare guidelines, which may change over time, and/or vary on a jurisdiction-by-jurisdiction basis. For example, in the United States, the American Diabetes Association provided guidance on management of high blood sugar. Riddle, M., et al., Journal of Clinical and Applied Research and Education., 41(1), (2018), the contents of which are hereby expressly incorporated by reference. These guidelines change over time as medical research and advances in treatment better inform management of high blood sugar.

Referring to block 440 of FIG. 4C, in some embodiments the first plurality of survey results further includes or indicates whether the subject is allergic to the metformin pharmaceutical composition, and the first plurality of filters includes an adverse reaction filter. The adverse reaction filter is fired when the first survey results indicate that the subject is allergic to the metformin pharmaceutical composition. In some embodiments, the adverse reaction filter is fired when the first survey results indicate that the subject has developed an adverse reaction to a medication containing metformin in the past.

Figure 7C:
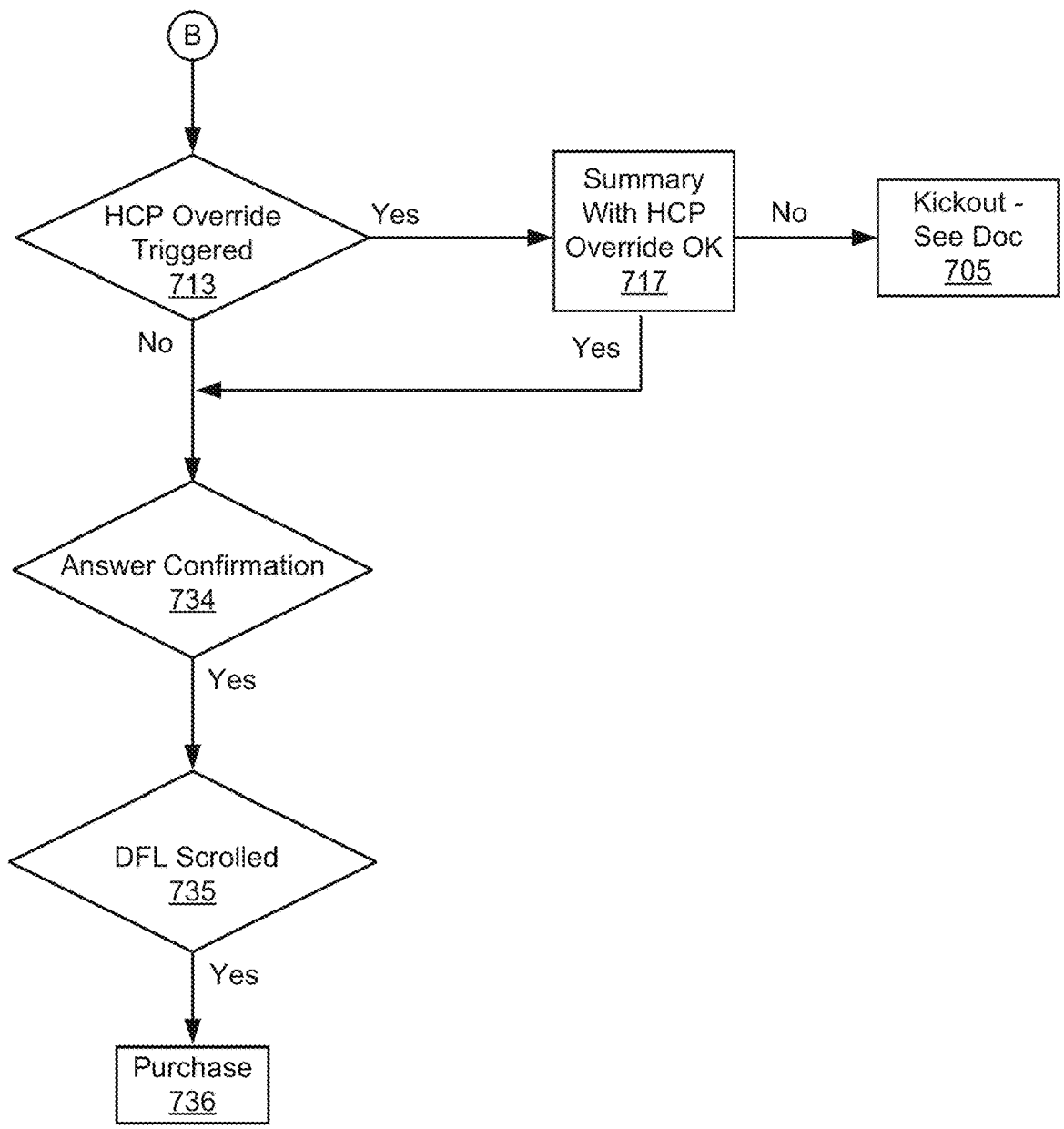

Referring to block 442, the method also includes running all or a portion of the first survey results against a second plurality of filters of a second category class 220. When a respective filter in the second plurality of filters is fired, the subject is provided with a warning 226 corresponding to the respective filter (e.g., filter warning 226-4 corresponds to filter 222-4). In some embodiments, the warning 226 is provided as a next step, e.g., prior to applying survey results to any subsequent filters, after the corresponding filter is fired. For example, with respect to FIG. 7B, in some embodiments, e.g., when the dehydration filter is triggered at 728, the device would provide the subject with a warning prior to proceeding to the diabetes medication filter at 730, e.g., requiring the subject confirm they have discussed their history of dehydration with a health care provider, e.g., and the healthcare provider still recommends taking a metformin pharmaceutical composition in order to proceed with the qualification. In some embodiments the warning 226 is provided after applying survey results to all subsequent filters. For example, as illustrated in FIGS. 7B and 7C, in some embodiments, e.g., when the dehydrated filter is triggered at 728, the device would proceed to the diabetes medication filter at 730 prior to transmitting a warning to the subject, and then transmit all warnings corresponding to filters of the second category class, at 734, after survey results have been applied to all subsequent filters.

In some embodiments, the second plurality of filters 222 of the second category class 220 includes some of all of the filters listed in Table 3. For example, in some embodiments, the first plurality of filters results includes 2, 3, 4, or all 5 of the filters listed in Table 3. In one embodiment, the first plurality of filters includes all of filters 1-5 as provided in Table 3.

TABLE 3

Example filters for risk factors associated with qualifying a subject for an over-the-counter provision of a metformin pharmaceutical composition

| Filter | Example Criteria |
| --- | --- |
| 1a | a liver disease filter |
| 2a | a medical issue filter |
| 3a | a surgery filter |
| 4a | a dehydration filter |
| 5a | a diabetes medication filter |

Referring to block 444, in some embodiments, the second plurality of filters includes a liver disease filter (e.g., liver disease filter 222-1 in FIG. 3 and/or filter 1a in Table 3). The liver disease filter is configured to be fired at least when the first plurality of survey results indicate that the subject has a liver problem. In some embodiments, liver problems that are capable of triggering the first liver disease filter include impaired hepatic function, acute liver failure, and cholestasis. When the liver disease filter is fired, the device transmits a warning corresponding to the liver disease filter, and requires the user to acknowledge the warning before authorizing a provision of the metformin pharmaceutical composition.

Referring to block 446, in some embodiments, the second plurality of filters includes a medical issue filter (e.g., medical issue filter 222-2 in FIG. 3 and/or filter 2a in Table 3). The medical issue filter is configured to be fired at least when the first plurality of survey results indicates that the subject has had a heart attack, the subject has had a severe infection, or the subject has had a stroke. When the medical issue filter is fired, the device transmits a warning corresponding to the medical issue filter, and requires the user to acknowledge the warning before authorizing a provision of the metformin pharmaceutical composition.

Referring to block 448, in some embodiments, the second plurality of filters includes a surgery filter (e.g., surgery filter 222-3 in FIG. 3 and/or filter 3a in Table 3). The surgery filter is configured to be fired at least when the first plurality of survey results indicates that the subject has recently undergone surgery, the subject is planning on undergoing surgery, or the subject is planning on having an x-ray procedure that includes injection of a contrast agent. When the surgery filter is fired, the device transmits a warning corresponding to the medical issue filter, and requires the user to acknowledge the warning before authorizing a provision of the metformin pharmaceutical composition.

Referring to block 450, in some embodiments, the second plurality of filters includes a dehydration filter (e.g., dehydration filter 222-4 in FIG. 3 and/or filter 4a in Table 3). The dehydration filter is configured to be fired at least when the first plurality of survey results indicates that the subject has developed symptoms of dehydration. In some embodiments, the dehydration filter is configured to be fired at least when the first plurality of survey results indicates that the subject has a history of dehydration. In some embodiments, the dehydration filter is configured to be fired at least when the first plurality of survey results indicates that the subject has experienced symptoms of dehydration including dizziness, faintness, light-headedness, and weakness, especially when standing up. When the dehydration filter is fired, the device transmits a warning corresponding to the dehydration filter, and requires the user to acknowledge the warning before authorizing a provision of the metformin pharmaceutical composition.

Referring to block 452, in some embodiments, the second plurality of filters includes a diabetes medication filter (e.g., diabetes medication filter 222-5 in FIG. 3 and/or filter 5a in Table 3). The diabetes medication filter is configured to be fired at least when the first plurality of survey results indicates that the subject is already taking a diabetes medication (e.g., a diabetes medication other than metformin, such as a sulfonylurea). In some embodiments, the diabetes medication which is capable of firing the diabetes mediation filter is a medication that has a same mechanism of action as the metformin composition. When the diabetes medication filter is fired, the device transmits a warning corresponding to the diabetes medications filter, and requires the user to acknowledge the warning before authorizing a provision of the metformin pharmaceutical composition.

It is contemplated that, in some embodiments, any one or more of the filters provided in Table 3 will not be included in the second plurality of filters. For example, in some embodiments, a characteristic associated with a particular survey result will be informative when qualifying a subject for one particular metformin pharmaceutical composition but not for another metformin pharmaceutical composition. Accordingly, it is contemplated that the second plurality of filters includes any sub-set of filters provided in Table 3. Likewise, the skilled artisan may know of other filters, not provided in Table 3, that may be combined with any subset of the filters provided in Table 3 to form the second plurality of filters results used in the methods described herein.

Contraindications and risk factors described in the present disclosure are non-exhaustive. The skilled artisan may know of other contraindications for a particular the metformin pharmaceutical composition and/or treat risk factors as contraindications dependent upon the intended use of the metformin pharmaceutical composition. In some embodiments, contraindications for use of a prescription-strength pharmaceutical agent are treated only as risk factors, or not at all, when qualifying a subject for a lower-dose OTC use of a metformin pharmaceutical composition.

Accordingly, it will be appreciated that the survey questions 208, 212, and filters 216, 222 applied to the survey answers thereof, may vary depending upon the metformin pharmaceutical composition being distributed. This is due to differences in the contraindication profiles of the various metformin pharmaceutical compositions, e.g., due to different drug-drug interactions, routes of drug clearance, etc. of the different the metformin pharmaceutical compositions.

Referring to block 456, the method includes obtaining acknowledgment from the subject for any warning 226 issued to the subject by any filter 222 in the second plurality of filters. In some embodiments, acknowledgment from the subject is a written acknowledgement, a verbal acknowledgment, or an electronic acknowledgment such as an electronic signature. If a filter 216 in the first plurality of filters fires, the subject is denied access to the over-the-counter metformin pharmaceutical composition.

Figure 6:
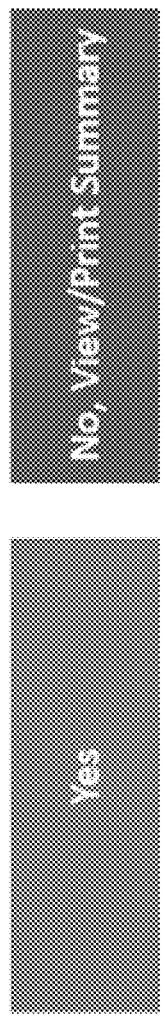
FIG. 6 illustrates feedback from a first survey in accordance with an embodiment of the present disclosure.

Referring to block 454, in some embodiments the warning 226 corresponding to a respective filter 222 in the second plurality of filters includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a metformin pharmaceutical composition in view of the underlying risk factor. Accordingly, acknowledgement is obtained from the subject when the subject indicates that they have discussed the risk factor underlying the respective filter in the second plurality of filters that was fired with a health care provider. For example, message 602 in FIG. 6 illustrates an example warning that is generic to any fired filters. In some embodiments, the warning is specific to a particular filter (e.g., filter warning 226 in FIG. 2), e.g., communicating to the user why the filter was fired.

In some embodiments, an acknowledgment from the user is verified by the health care practitioner (e.g., the method requires verification in order for authorization of the provision of the metformin pharmaceutical composition), e.g., in order to verify an accuracy of the survey results of the subject. In some embodiments, e.g., when the acknowledgment is verified by the heath care practitioner, the subject is deemed a trusted subject, such that verification of future results is not required.

Blocks 466-476.

Referring to block 458 of FIG. 4D, the process control proceeds to the fulfillment process when no filter 216 in the first plurality of filters has been fired and the subject has acknowledged each warning 226 associated with each filter 222 in the second plurality of filters that was fired. In some embodiments, the fulfillment process includes storing an indication in a user profile 234 of an initial order date and/or destination for the metformin pharmaceutical composition. The initial order date is utilized, for example, to verify at least a refill status of a provision of the metformin composition. The initial order date is also utilized, for example, to verify at least an elapsed period of time between an initial order and a future re-order. Such verification is required in order to ensure that certain tests (e.g., blood sugar level tests) are taken regularly.

The fulfillment process further includes communicating an over-the-counter drug facts label 230 for the metformin pharmaceutical composition to the subject. In some embodiments, the drug facts label is communicated to the subject in real-time, e.g., within the same user interface as used for the qualification process. In some embodiments, the over-the-counter drug facts label 230 specifies what the metformin composition is for (e.g., to lower blood sugar levels, to treat diabetes, etc.), what dosage the subject is being authorized to take, and/or any risks associated with taking the metformin pharmaceutical composition (e.g., drug-drug interactions, pharmacokinetic interactions, adverse reactions, etc.).

Referring to block 460, in some embodiments the fulfillment process further includes authorizing provision of the metformin pharmaceutical composition to the subject. The authorization occurs upon confirmation from the subject that the over-the-counter drug facts label 230 has been received and read by the subject. In some embodiments, this authorization includes a destination associated with the subject (block 466). In some embodiments, the destination associated with the subject is stored in the user profile 234. In some embodiments, the destination associated with the subject is a physical address including a street address, a Post Office box, a pharmacy associated with the subject, a health care provider associated with the subject, and/or one or more coordinates (e.g., longitude, latitude, elevation). In some embodiments, the provision of the metformin pharmaceutical composition to the subject comprises shipping the metformin pharmaceutical composition to the physical address associated with the subject (block 468). In some embodiments, the provision of the metformin pharmaceutical composition to the subject comprises shipping the metformin pharmaceutical composition to a pharmacy associated and/or a location associated with a health care provider of the subject and/or an office of a medical practitioner associated with the subject.

Blocks 470-514.

Referring to blocks 470-514 of FIGS. 4E-4I, a re-fulfillment process will be described infra. In some embodiments, the present disclosure provides a method for qualifying a subject for a refill of metformin pharmaceutical composition. In some embodiments, the qualification for a refill of the metformin pharmaceutical composition follows an initial qualification of the subject, as described herein. In some embodiments, the qualification for a refill of the metformin pharmaceutical composition follows issuance of a prescription to the subject for the metformin pharmaceutical composition. For example, in some embodiments, a subject who is new to the qualification process is asked whether they previously received a prescription for the metformin pharmaceutical composition and, if the subject indicates that they have not previously received a prescription, the subject is directed to an initial qualification method and, if the subject indicates that they have previously received a prescription, the subject is directed to the refill qualification method, e.g., as described below.

Referring to block 470 of FIG. 4E, in some embodiments a re-fulfillment procedure is performed. The re-fulfillment procedure is responsive to receiving a re-order request from the subject for the metformin pharmaceutical composition. In some embodiments, a prompt to initiate the re-fulfillment procedure is sent to user device 102 associated with the subject after a predetermined amount of time associated with a duration of dosages previously delivered to the subject (e.g., the user is reminded to fulfill their order of the metformin pharmaceutical composition just before, or just after, the user is scheduled to run out of a previously delivered provision.

Referring to blocks 472-474, in some embodiments the re-fulfillment procedure includes conducting a second survey of the subject. The second survey is configured to obtain a second plurality of survey results. These results are derived from corresponding survey questions (e.g., the device transmits one or more survey questions to the user, prompting a response, and then receives a response to the one or more survey questions back from the subject). In some embodiments, the second plurality of survey results include, or at least indicate, some or all of the subject characteristics listed in Table 4. For example, in some embodiments, the second plurality of survey results includes, or at least indicates, 1, 2, 3, 4, 5, 6, 7, 8, 9, 10, 11, or all 12 of the characteristic listed in Table 4. In one embodiment, the second survey questions and results include at least characteristics 1-11 as provided in Table 4.

In some embodiments, the second survey results indicate whether the subject is one of pregnant, breastfeeding, or planning to become pregnant (e.g., responsive to a survey question that is associated with and/or applied to (808) a pregnancy filter 216-9 of a first category class 214-2), whether the subject has developed a kidney problem since receiving their last provision of the metformin pharmaceutical composition (e.g., responsive to a survey question that is associated with and/or applied to (810) kidney disease filter 216-10 of a first category class), an alcohol consumption status of the subject (e.g., responsive to a survey question that is associated with and/or applied to (812) an alcohol consumption filter 216-11 of a first category class), whether the subject has developed ketoacidosis since receiving their last provision of the metformin pharmaceutical composition (e.g., responsive to a survey question that is associated with and/or applied to (814) a ketoacidosis symptom filter 216-12 of a first category class), whether the subject has developed lactic acidosis since receiving their last provision of the metformin pharmaceutical composition (e.g., responsive to a survey question that is associated with and/or applied to (816) a lactic acidosis symptom filter 216-13 of a first category class), whether the subject has experienced an illness causing vomiting, diarrhea, or fever since receiving their last provision of the metformin pharmaceutical composition (e.g., responsive to a survey question that is associated with and/or applied to (818) an illness filter 216-14 of a first category class), whether the subject has developed a liver problem since receiving their last provision of the metformin pharmaceutical composition (e.g., responsive to a survey question that is associated with and/or applied to (820) a liver disease filter 222-6 of a second category class 220-2), whether the subject has experienced a heart attack, severe infection, or stroke since receiving their last provision of the metformin pharmaceutical composition (e.g., responsive to a survey question that is associated with and/or applied to (822) a medical issue filter 222-7 of a second category class), a surgery status of the subject (e.g., responsive to a survey question that is associated with and/or applied to (824) a surgery filter 222-8 of a second category class), whether the subject has experienced dehydration since receiving their last provision of the metformin pharmaceutical composition (e.g., responsive to a survey question that is associated with and/or applied to (826) a dehydration filter 222-9 of a second category class), whether the subject has started taking a new diabetes medication since receiving their last provision of the metformin pharmaceutical composition (e.g., responsive to a survey question that is associated with and/or applied to (828) a diabetes medication 222-110 filter of a second category class), and, if the subject has been taking the metformin pharmaceutical composition for at least a predetermined period of time, a blood sugar level of the subject (e.g., responsive to a survey question, or questions, that is/are associated with and/or applied to (830,832) an blood sugar level filter 216-15 of a first category class).

In some embodiments, the second survey includes questions that elicit responses providing some or all of the characteristics listed in Table 4. In some embodiments, the second survey includes questions corresponding to each of the survey results required for the methods described herein. In other embodiments, the second survey includes questions corresponding to only a subset of the survey results required for the methods described herein. In some embodiments, other survey results required for the methods described herein are acquired through other means (e.g., upon registration/subscription for a service associated with qualifying the subject for over-the-counter medication, from a healthcare provider, from a prior survey, from a database associated with a pharmacy, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a last blood sugary level measurement determined for the subject).

TABLE 4

Example characteristics for re-qualifying a subject for an over-the-counter provision of a metformin pharmaceutical composition

| Result | Example Characteristics |
|---|---|
| 1 | whether the subject is one of (i) pregnant, (ii) breastfeeding, or (iii) planning to become pregnant |
| 2 | whether the subject has developed a kidney problem |
| 3 | an alcohol consumption status of the subject |
| 4 | whether the subject has developed ketoacidosis |
| 5 | whether the subject has developed lactic acidosis |
| 6 | whether the subject has experienced an illness causing vomiting, diarrhea, or fever |
| 7 | whether the subject has developed a liver problem |
| 8 | whether the subject has experienced a heart attack, severe infection, or stroke |
| 9 | a surgery status of the subject |
| 10 | whether the subject has experienced dehydration |
| 11 | whether the subject is taking another diabetes medication |
| 12 | a blood sugar level of the subject |

It is contemplated that, in some embodiments, any one or more of the survey questions provided in Table 4 will not be included in the second survey (e.g., will not be used for the reassessment). For example, in some embodiments, a characteristic associated with a particular survey questions will be informative when qualifying a subject for one particular metformin composition but not for another metformin composition. The skilled artisan will recognize that different metformin compositions carry different risk and drug interaction profiles. Accordingly, survey information required for qualifying a subject for access to one metformin composition with a known adverse drug interaction may not be necessary for qualifying the same subject for access to a second metformin composition.

Accordingly, it is contemplated that the second survey questions elicit responses to any sub-set of survey results provided in Table 4. For brevity, all possible combinations of the characteristics provided in Table 4 are not specifically delineated here. However, the skilled artisan will easily be able to envision any particular subset of survey questions designed to elicit responses to any subset of characteristics provided in Table 4. Likewise, the skilled artisan may know of other survey questions, not provided in Table 4, that may be combined with any subset of the survey questions provided in Table 4 to form the second survey questions used in the methods described herein.

Referring to block 476 of FIG. 4F, all or a portion the results are run against a third plurality of filters of the first category class. When a respective filter in the third plurality of filters is fired (e.g., when a survey result indicates that a triggering condition 218 has been met), the subject is deemed not qualified for the metformin pharmaceutical composition and the method is terminated without delivery of the metformin pharmaceutical composition.

Referring to blocks 478-490, specific filters in the third plurality of filters and their exemplary triggering conditions that cause the corresponding filter to fire are detailed.

In some embodiments, the third plurality of filters of the first category class includes some or all of the filters 216 listed in Table 5. For example, in some embodiments, the third plurality of filters results includes 1, 2, 3, 4, 5, or all 6 of the filters listed in Table 5. In one embodiment, the third plurality of filters includes all of filters 1-6 listed in Table 5.

TABLE 5

Example filters for contraindications associated with re-qualification of a subject for an over-the-counter provision of a metformin pharmaceutical composition

| Filter | Example Criteria |
|---|---|
| 1a | a pregnancy filter |
| 2a | a kidney disease filter |
| 3a | An alcohol consumption filter |
| 4a | a ketoacidosis filter |
| 5a | a lactic acidosis filter |
| 6a | an illness filter |
| 7a | a blood sugar maintenance filter |

It is contemplated that, in some embodiments, any one or more of the filters provided in Table 5 will not be included in the third plurality of filters. For example, in some embodiments, a characteristic associated with a particular survey result will be informative when qualifying a subject for one particular metformin composition but not for another metformin composition. Likewise, the skilled artisan may know of other filters, not provided in Table 5, which may be combined with any subset of the filters provided in Table 5 to form the third plurality of filters results used in the methods described herein. For brevity, all possible combinations of the filters provided in Table 5 are not specifically delineated here.

Referring to blocks 478-480, in some embodiments the third plurality of filters includes a pregnancy filter, e.g., as described above in relation to the first survey. In some embodiments, the pregnancy filter is configured to be fired at least when the second plurality of survey results indicates that the subject is pregnant or the subject is breastfeeding. In some embodiments, the pregnancy filter is also configured to be fired when the subject is planning on becoming pregnant. When the pregnancy filter is fired, the subject is not permitted to obtain the metformin pharmaceutical composition over-the-counter (e.g., the method is terminated without authorizing re-provision of the metformin pharmaceutical composition to the subject).

Referring to block 482, in some embodiments the third plurality of filters includes a kidney disease filter. In some embodiments, the kidney disease filter is configured to be fired at least when the second plurality of survey results indicates that the subject has developed a kidney problem since receiving their last provision of the metformin pharmaceutical composition. When the kidney disease filter is fired, the subject is not permitted to obtain the metformin pharmaceutical composition over-the-counter (e.g., the method is terminated without authorizing re-provision of the metformin pharmaceutical composition to the subject). In some embodiments, the second plurality of survey results indicates that the subject has developed a kidney problem when the second plurality of survey results include that the subject has been diagnosed with a kidney disorder since receiving their last provision of the metformin composition. In some embodiments, the second plurality of survey results indicates that the subject has developed a kidney problem when the second plurality of survey results include that the subject has experienced a symptom (e.g., a new and/or worsening symptom) of a kidney problem since receiving their last provision of the metformin composition, e.g., nausea, fatigue, loss of appetite, and/or high blood pressure. In some embodiments, the kidney disease filter is configured to be fired at least when the first plurality of survey results indicates that the subject has compromised kidney function, e.g., below a floor kidney function level (e.g., GFR) such as 30 mL/min/1.73 m$^2$ or 45 mL/min/1.73 m$^2$. In some embodiments, the kidney disease filter is configured to be fired at least when the first plurality of survey results indicates that the subject has compromised kidney function as determined according to a set of healthcare guidelines, which may change over time, and/or vary on a jurisdiction-by-jurisdiction basis. For example, the National Kidney Foundation provided guidance for chronic kidney disease and corresponding GFR levels. Levey, et al., Clinical Practice Guidelines for Chronic Kidney Disease: Evaluation, Classification and Stratification, National Kidney Foundation, (2002).

Referring to block 484-486, in some embodiments the third plurality of filters includes an alcohol consumption filter, e.g., as described above in relation to the first survey. In some embodiments, the alcohol consumption filter is configured to be fired when the first plurality of survey results indicates that the subject has begun abusing alcohol. In some embodiments, the alcohol consumption filter is configured to be fired when the first plurality of survey results indicates that the subject drinks alcohol very often, e.g., at least one alcoholic drink per day, at least two alcoholic drinks per day, at least three alcoholic drinks per day, or four or more alcoholic drinks per day, or at least four, five, six, seven, eight, nine, ten, or more drinks per week. In some embodiments, the alcohol consumption filter is configured to be fired when the second plurality of survey results indicate the subject is binge drinking. When the alcohol consumption filter is fired, the subject is not permitted to obtain the metformin pharmaceutical composition over-the-counter (e.g., the method is terminated without authorizing re-provision of the metformin pharmaceutical composition to the subject).

Referring to block 488-490, in some embodiments the third plurality of filters includes a ketoacidosis filter. In some embodiments, the ketoacidosis filter is configured to be fired at least when the second plurality of survey results indicates that the subject has developed ketoacidosis since receiving their last provision of the metformin pharmaceutical composition. In some embodiments, the second plurality of survey results indicates that the subject has developed ketoacidosis when the second plurality of survey results include that the subject has been diagnosed with ketoacidosis since receiving their last provision of the metformin composition. In some embodiments, the second plurality of survey results indicates that the subject has developed ketoacidosis when the second plurality of survey results include that the subject has experienced a symptom (e.g., a new and/or worsening symptom) of ketoacidosis since receiving their last provision of the metformin composition, e.g., an increase of ketones in the blood of the subject, an increase of ketones in the urine of the subject, nausea, tiredness, vomiting, trouble breather, and/or abdominal pain. When the ketoacidosis symptom filter is fired, the subject is not permitted to obtain the metformin pharmaceutical composition over-the-counter (e.g., the method is terminated without authorizing re-provision of the metformin pharmaceutical composition to the subject).

Referring to block 492-494 of FIG. 4G, in some embodiments the third plurality of filters comprises a lactic acidosis filter. In some embodiments, the lactic acidosis filter is configured to be fired at least when the second plurality of survey results indicates that the subject has developed lactic acidosis since receiving their last provision of the metformin pharmaceutical composition. In some embodiments, the second plurality of survey results indicates that the subject has developed lactic acidosis when the second plurality of survey results include that the subject has been diagnosed with lactic acidosis since receiving their last provision of the metformin composition. In some embodiments, the second plurality of survey results indicates that the subject has developed lactic acidosis when the second plurality of survey results include that the subject has experienced a symptom (e.g., a new and/or worsening symptom) of lactic acidosis since receiving their last provision of the metformin composition, e.g., cold feelings in the subject's hands or feet, dizziness, lightheadedness, slow or irregular heartbeat, feeling very weak or tired, unusual muscle pain, difficulty breathing, stomach pains, nausea, and/or vomiting. When the lactic acidosis filter is fired, the subject is not permitted to obtain the metformin pharmaceutical composition over-the-counter (e.g., the method is terminated without authorizing re-provision of the metformin pharmaceutical composition to the subject).

Referring to block 496, in some embodiments the third plurality of filters includes an illness filter. In some embodiments, the illness filter is configured to be fired at least when the second plurality of survey results indicates that the user has experienced an illness (e.g., a serious illness) since receiving their last provision of the metformin pharmaceutical composition. In some embodiments, a serious illness capable of firing the illness filter is an illness associated with vomiting, diarrhea, and/or fever. When the illness filter is fired, the subject is not permitted to obtain the metformin pharmaceutical composition over-the-counter (e.g., the method is terminated without authorizing re-provision of the metformin pharmaceutical composition to the subject).

Referring to blocks 498-500, in some embodiments the third plurality of filters includes a blood sugar maintenance filter. In some embodiments, the blood sugar maintenance filter is configured to be fired at least when the subject's blood sugar is not being maintained at an acceptable level, while taking the metformin pharmaceutical composition. In some embodiments, the blood sugar maintenance filter is fired when the second plurality of survey results indicate that the subject's blood sugar levels are at or above a second floor blood sugar level. In some embodiments, the second floor blood sugar level used in the second blood sugar filter is 7% glycated hemoglobin. In some embodiments, the blood sugar maintenance filter is only fired if a threshold amount of time has passed since the subject started taking the metformin pharmaceutical composition, e.g., to allow time for the blood sugar-lowering effects of the composition to occur before determining whether the composition is working effectively, or a threshold amount of time has passed since the subject last reported a status of their blood sugar level (e.g., in connection with a qualification or re-qualification for a provision of the metformin pharmaceutical composition), e.g., to avoid stopping the subject's use of the drug due to short-term fluctuations in the subject's blood sugar level. In some embodiments, the device does not run the blood sugar maintenance filter (e.g., apply one or more survey results), or query the user to provide an indication of their blood sugar level, when a predetermined period of time has not passed. For example, in some embodiments, the device determines whether the user received their first provision of the metformin pharmaceutical composition within a first threshold amount of time (e.g., in the past 2, 3, 4, 5, or 6 months) and/or whether the user reported an indication of their blood sugar level within a second threshold period of time (e.g., where their last provision of the metformin pharmaceutical composition was not their first provision of the composition). In some embodiments, the first threshold amount of time, e.g., since the user received their first provision of the metformin pharmaceutical composition, is three months. In some embodiments, the second threshold period of time, e.g., since the user last reported a provision of the metformin pharmaceutical composition, is six months. In some embodiments, the first and/or second threshold amount of time are independently one of one, two, three, four, five, six, seven, eight, nine, ten, eleven, twelve months, or more. In some embodiments, the second floor blood sugar level used in the second blood sugar filter is 7% glycated hemoglobin. When the blood sugar filter is fired, the subject is not permitted to obtain the metformin pharmaceutical composition over-the-counter (e.g., the method is terminated without authorizing re-provision of the metformin pharmaceutical composition to the subject). In some embodiments, the blood sugar cutoffs defining when the blood sugar filter is fired and when the blood sugar filter is not fired are set according to a set of healthcare guidelines, which may change over time, and/or vary on a jurisdiction-by-jurisdiction basis. For example, in the United States, the American Diabetes Association provided guidance on management of diabetes and blood sugar. Riddle, et al. American Diabetes Association Standards of Medical Care in Diabetes—2018, Diabetes Cares 41(1), (2018), the contents of which are hereby expressly incorporated by reference. These guidelines change over time as medical research and advances in treatment better inform management of diabetes.

In some embodiments, the device accounts for gaps in the subject's use of the metformin pharmaceutical composition when determining whether the subject's blood sugar is being effectively managed by administration of the composition (e.g., in some embodiments, where the device determines that the user has been without a provision of the metformin pharmaceutical composition for a threshold period of time, the device bypasses the blood sugar maintenance filter, or relaxes the requirements of the filter, for example, to a blood sugar level below that of the first ceiling blood sugar level).

Figure 8A:
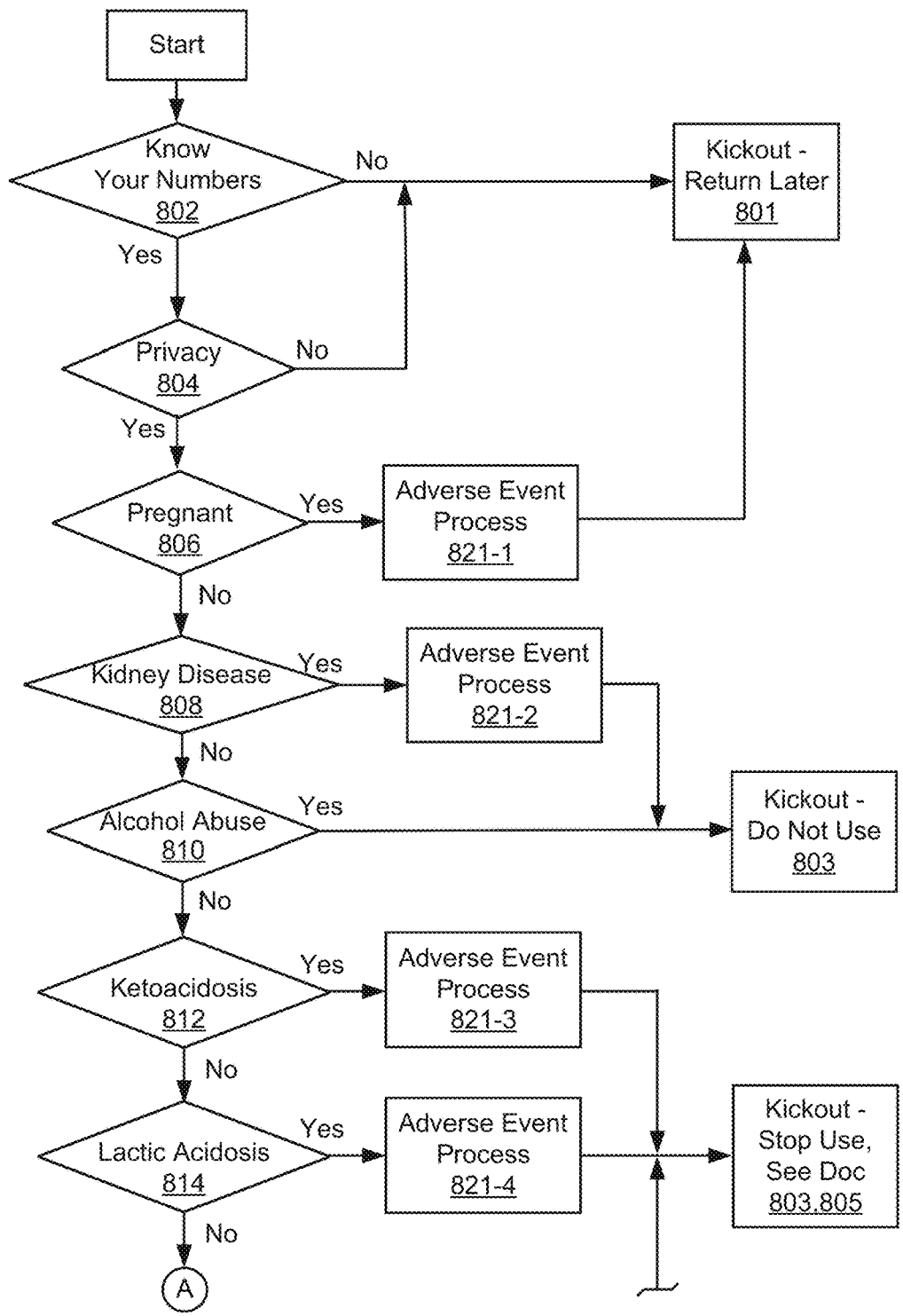
FIGS. 8A, 8B, and 8C collectively illustrate an example method for qualifying a subject for a refill of an over-the-counter provision of a metformin pharmaceutical composition, in accordance with an embodiment of the present disclosure.
Figure 8B:
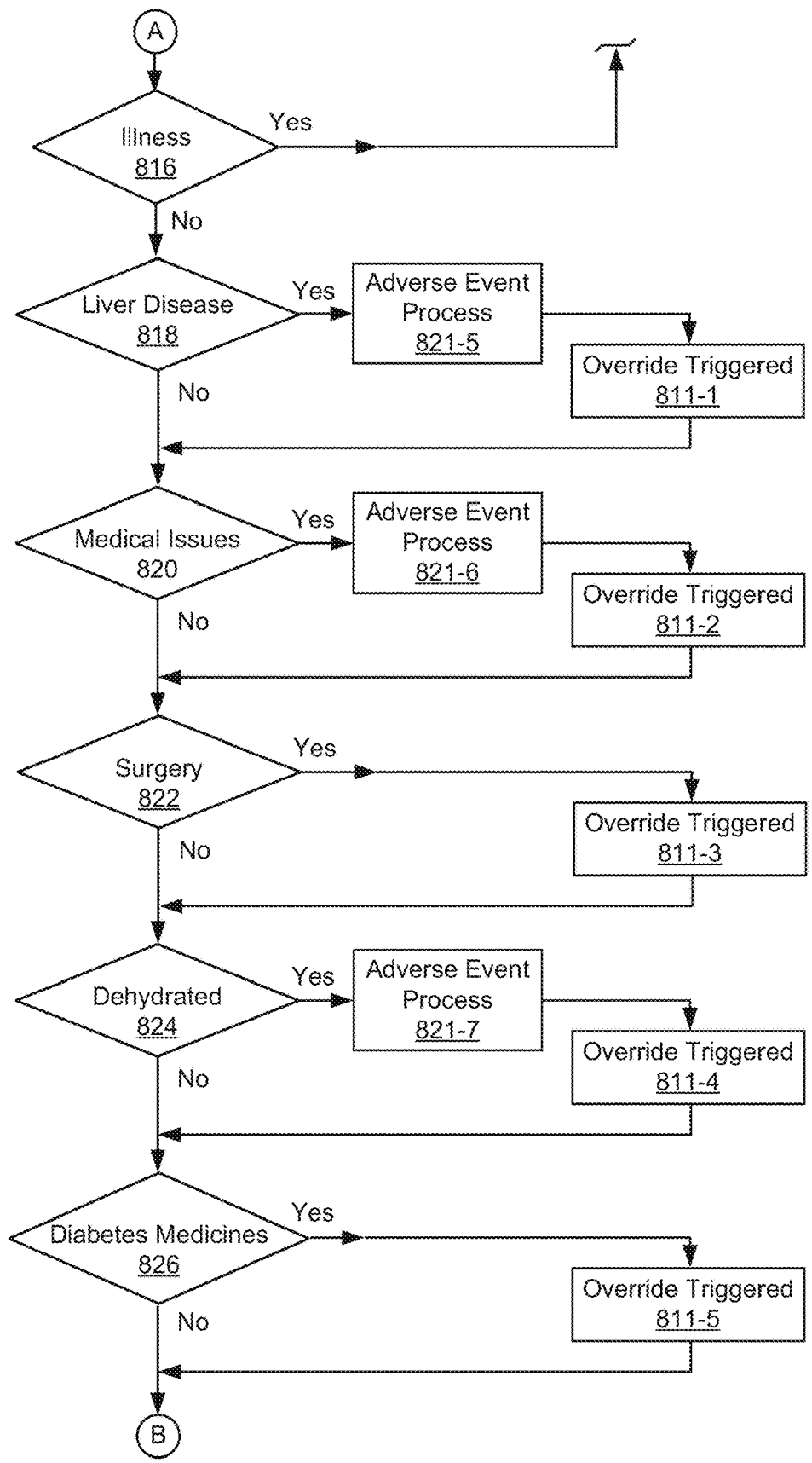
Figure 8C:
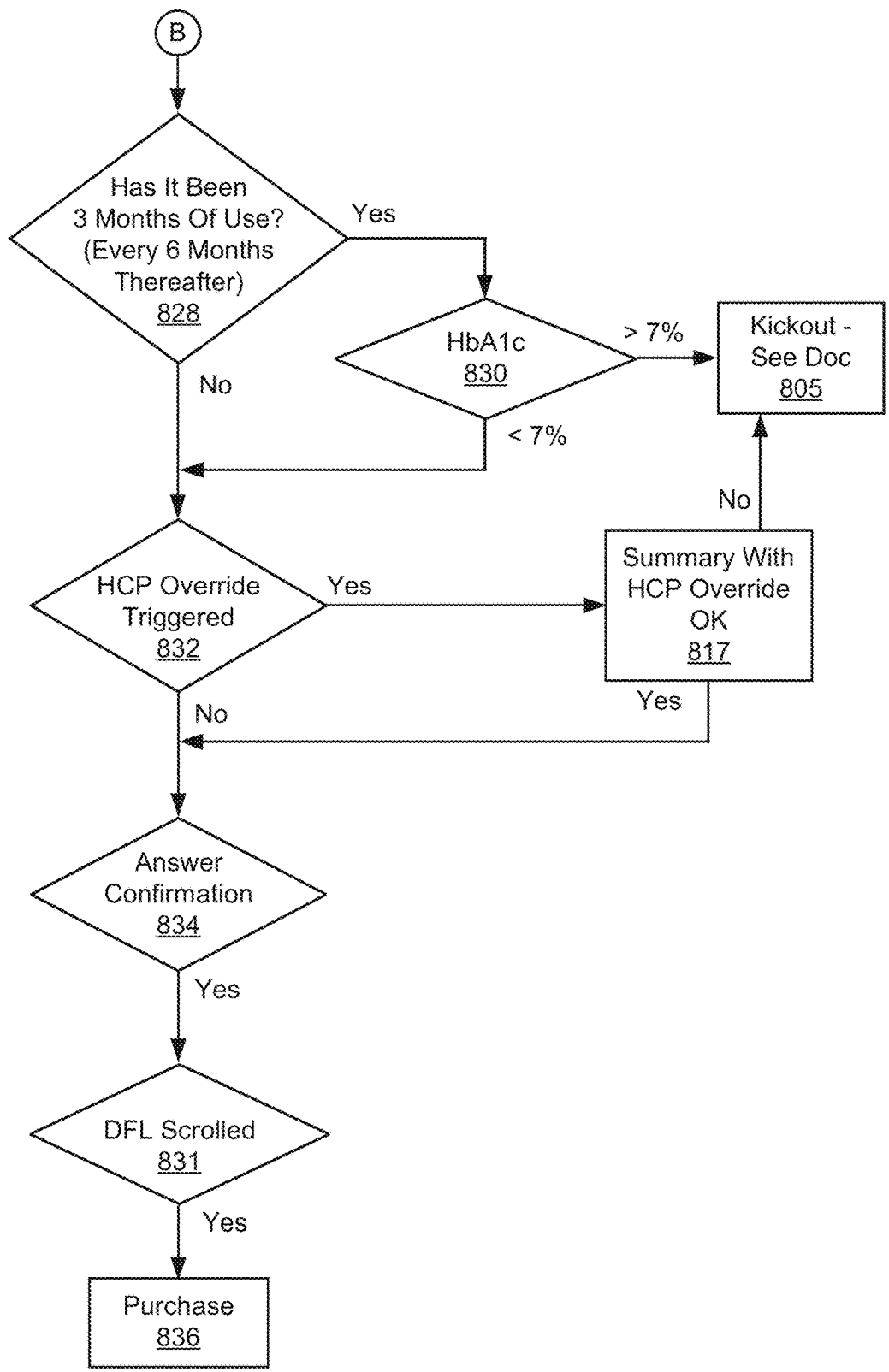

Referring to block 502 of FIG. 4H, the method also includes running all or a portion of the second survey results against a fourth plurality of filters of the second category class 220-2. When a respective filter in the fourth plurality of filters is fired, the subject is provided with a warning corresponding to the respective filter. In some embodiments, the warning is provided as a next step, e.g., prior to applying survey results to any subsequent filters, after the corresponding filter is fired. For example, with respect to FIGS. 8A-8C, in some embodiments, e.g., when the surgery filter is triggered at 824, the device would provide the subject with a warning prior to proceeding to the dehydration filter at 826, e.g., requiring the subject confirm they have discussed their surgery status with a health care provider, e.g., and the healthcare provider still recommends taking a metformin pharmaceutical composition. In some embodiments the warning is provided after applying survey results to all subsequent filters. For example, with respect to FIGS. 8A-8C, in some embodiments, e.g., when the surgery filter is triggered at 824, the device would proceed to the dehydration filter at 826 prior to transmitting a warning to the subject, and then transmit all warnings corresponding to filters of the second category class, at 836, after survey results have been applied to all subsequent filters.

In some embodiments, the fourth plurality of filters of the second category class 220-2 includes some or all of the filters listed in Table 6. For example, in some embodiments, the fourth plurality of filters includes 2, 3, 4, 5, or all 6 of the filters listed in Table 6. In some embodiments, the fourth plurality of filters of the second category class includes at least filters 1-5, as listed in Table 2.

TABLE 6

Example filters for risk factors associated with re-qualifying a subject for an over-the-counter provision of a metformin pharmaceutical composition

| Filter | Example Criteria |
| --- | --- |
| 1a | a liver disease filter |
| 2a | a medical issue filter |
| 3a | a surgery filter |
| 4a | a dehydration filter |
| 5a | a diabetes medication filter |
| 6a | a side effects filter |

It is contemplated that, in some embodiments, any one or more of the filters provided in Table 6 will not be included in the fourth plurality of filters. For example, in some embodiments, a characteristic associated with a particular survey result will be informative when qualifying a subject for one particular metformin pharmaceutical composition but not for another metformin pharmaceutical composition. Accordingly, it is contemplated that the fourth plurality of filters includes any sub-set of filters provided in Table 6. Likewise, the skilled artisan may know of other filters, not provided in Table 6, that may be combined with any subset of the filters 222 provided in Table 6 to form the fourth plurality of filters results used in the methods described herein.

Referring to block 504, in some embodiments, the fourth plurality of filters includes a liver disease filter that is fired at least when the second plurality of survey results indicates that the subject has developed a liver problem since receiving their last provision of the metformin pharmaceutical composition. In some embodiments, the second plurality of survey results indicates that the subject has developed a liver problem when the second plurality of survey results include that the subject has been diagnosed with a liver problem since receiving their last provision of the metformin composition. In some embodiments, the second plurality of survey results indicates that the subject has developed a liver problem when the second plurality of survey results include that the subject has experienced a symptom (e.g., a new and/or worsening symptom) of a liver problem since receiving their last provision of the metformin composition, e.g., hepatic enzyme elevations (e.g., which are mostly consistent with cholestasis or hepatitis), jaundice, abdominal pain and/or swelling, swelling in the legs and/or ankles, irritated skin, a dark urine color, a pale, bloody, or tar-colored stool, chronic fatigue, nausea and/or vomiting, loss of appetite, and/or a tendency to bruise easily. When the liver disease filter is fired, the device transmits a warning corresponding to the liver disease filter, and requires the user to acknowledge the warning before authorizing a provision of the metformin pharmaceutical composition.

Referring to block 504, in some embodiments, the fourth plurality of filters includes a medical issue filter that is fired at least when the second plurality of survey results indicates that the subject has had a heart attack, the subject has had a severe infection (e.g., sepsis), or the subject has had a stroke, since receiving their last provision of the metformin pharmaceutical composition. In some embodiments, the medical issues (e.g., triggering conditions 224) that are capable of firing a medical issue filter associated with the second survey are the same as the medical issues that are capable of firing a medical issue filter associated with the first survey. When the medical issue filter is fired, the device transmits a warning corresponding to the medical issue filter, and requires the user to acknowledge the warning before authorizing a provision of the metformin pharmaceutical composition.

Referring to block 504, in some embodiments, the fourth plurality of filters includes a surgery filter that is fired at least when the second plurality of survey results indicates that the subject has undergone surgery since receiving their last provision of the metformin pharmaceutical composition, the subject is planning on undergoing surgery, or the subject is planning on having an x-ray procedure that includes injection of a contrast agent. In some embodiments, the triggering conditions capable of firing a surgery filter associated with the second survey are the same as, or substantially similar to, the triggering conditions that are capable of firing a surgery filter associated with a first survey. When the surgery filter is fired, the device transmits a warning corresponding to the surgery filter, and requires the user to acknowledge the warning before authorizing a provision of the metformin pharmaceutical composition.

Referring to block 504, in some embodiments, the fourth plurality of filters includes a dehydration filter that is fired at least when the second plurality of survey results indicates that the subject has experienced dehydration since receiving their last provision of the metformin pharmaceutical composition. In some embodiments, the second plurality of survey results indicates that the subject has experienced dehydration when the second plurality of survey results include that the subject has experienced a symptom (e.g., a new and/or worsening symptom) of dehydration since receiving their last provision of the metformin composition, e.g., dizziness, faintness, light-headedness, and weakness, especially when standing. In some embodiments, dehydration symptoms (e.g., triggering conditions 224) capable of firing a dehydration filter associated with the second survey are the same as symptoms that are capable of firing a dehydration filter associated with the first survey. When the dehydration filter is fired, the device transmits a warning corresponding to the dehydration filter, and requires the user to acknowledge the warning before authorizing a provision of the metformin pharmaceutical composition.

Referring to block 504, in some embodiments, the fourth plurality of filters includes a diabetes medication filter that is fired at least when the second plurality of survey results indicates that the subject is taking another diabetes medication (e.g., has started taking another diabetes medication since receiving their last provision of the metformin pharmaceutical composition. In some embodiments, diabetes medications (e.g., triggering conditions 224) capable of firing a diabetes medication filter associated with the second survey are the same as diabetes medications capable of firing a diabetes medication filter associated with the first survey. When the diabetes medication filter is fired, the device transmits a warning corresponding to the diabetes medication filter, and requires the user to acknowledge the warning before authorizing a provision of the metformin pharmaceutical composition.

Referring to block 506, in some embodiments the second survey results further include whether the subject has developed side effects associated with the metformin pharmaceutical composition since receiving their last provision of the metformin pharmaceutical composition. Accordingly, in some embodiments, the fourth plurality of filters further includes a side effect filter that is configured to be fired at least when the second survey results indicate that the subject has developed side effects since receiving their last provision of the metformin pharmaceutical composition. Side effects that are capable of triggering the side effect filter include a metallic taste, diarrhea, nausea, and an upset stomach. When the side effect filter is fired, the device transmits a warning corresponding to the side effects filter, and requires the user to acknowledge the warning before authorizing a provision of the metformin pharmaceutical composition.

Referring to block 508, in some embodiments when a respective filter in the third plurality of filters or fourth plurality of filters is fired, a record associated with the firing of the respective filter is created (e.g., memorializing an adverse event that is required to be reported to a regulatory agency). This record is stored in an adverse event module 242 which includes records of filter firing events associated with a plurality of subjects (e.g., an aggregation of adverse events associated with the metformin pharmaceutical composition across a population of subjects taking the metformin pharmaceutical composition over-the-counter). In some embodiments, an indication of the adverse event is communicated to a third party (e.g., a medical practitioner associated with the subject, a health care provider of the subject, a manufacturer/promoter of the metformin pharmaceutical composition and/or a regulatory agency). In some embodiments, the indication is automatically stored in the adverse event module 242 when a response submitted by a subject, as part of the second survey, triggers a filter associated with an adverse event.

Figure 4I:
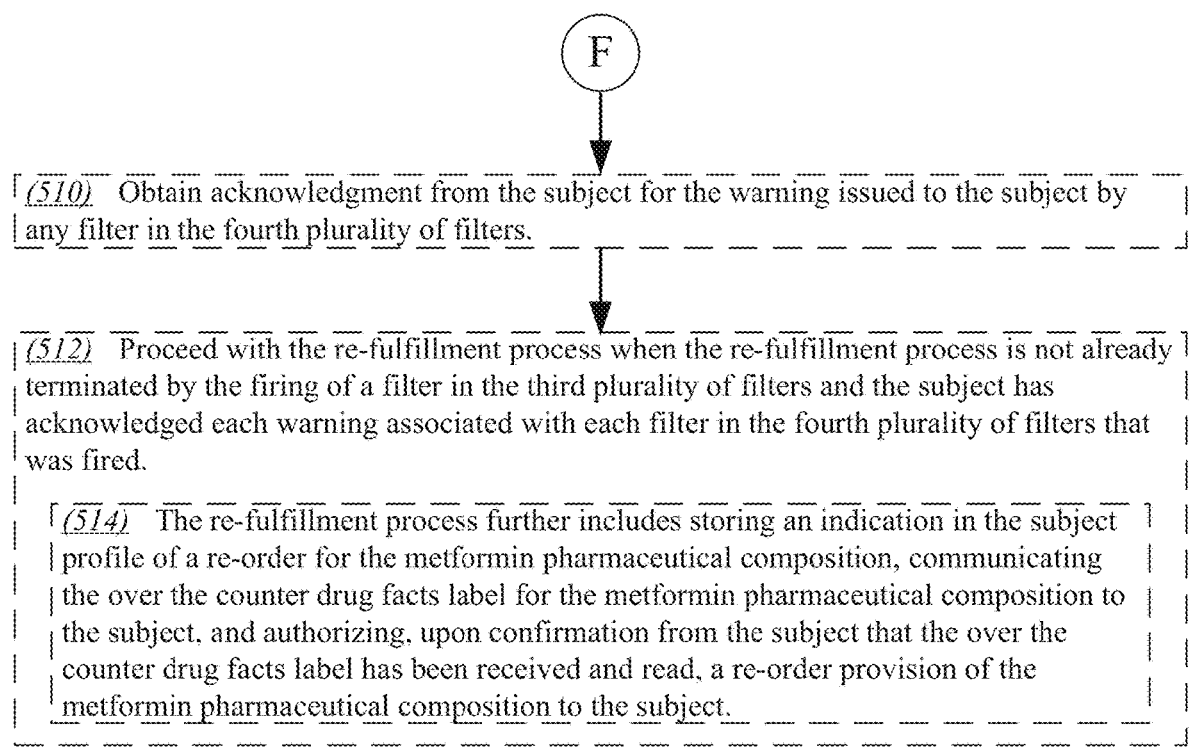

Referring to block 510 of FIG. 4I, in some embodiments the method also includes obtaining acknowledgment from the subject for each warning issued to the subject by any filter in the fourth plurality of filters. As described with respect to the warnings issued in conjunction with the second plurality of filters of the second category class, in some embodiments, the warning includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should continue to take the metformin pharmaceutical composition in view of the underlying risk factor. Accordingly, acknowledgement is obtained from the subject when the subject indicates that they have discussed the risk factor underlying the respective filter in the fourth plurality of filters that was fired with a health care provider.

Referring to block 512, in some embodiments the procedure further includes proceeding with the re-fulfillment process when the re-fulfillment process is not already terminated by the firing of a filter in the third plurality of filters (e.g., the second pregnancy filter). In order for completion of the re-fulfillment process, the subject is required to acknowledge each warning associated with each filter 222-2 in the fourth plurality of filters that was fired.

Referring to block 514, in some embodiments the re-fulfillment process also includes storing a record in the user profile 234 of the subject of a re-order 238 for the metformin pharmaceutical composition.

The re-fulfillment process also includes communicating an over-the-counter drug facts label 230 for the metformin pharmaceutical composition to the subject. As previously described, communication of the over-the-counter drug facts label 230 can occur in a variety of means. Upon confirmation from the subject that the over-the-counter drug facts label 230 has been received and read, the method includes authorizing a re-order provision of the metformin pharmaceutical composition to the subject. In some embodiments, this re-order provision includes the destination of the subject.

FIG. 7 illustrates an example method (700) (e.g., performed at an electric device 102 or 250) for qualifying a subject for an over-the-counter metformin pharmaceutical composition. In some embodiments, the method of FIG. 7 is utilized when the subject has not been previously qualified for the metformin pharmaceutical composition. In some embodiments, the method of FIG. 7 is utilized when the subject was previously qualified for the metformin pharmaceutical composition but a predetermined period of time elapsed since the previous qualification occurred (e.g., the most recent qualification/re-qualification of the subject was greater than one year ago).

Referring to FIG. 7, the device prompts (702) the user to confirm that they know their blood sugar levels (e.g., because the subject must know their blood sugar levels in order to complete the qualification process). If the subject indicates they do not know their blood sugar levels, the process terminates (701) without authorizing provision of the metformin pharmaceutical agent, and optionally transmits advice to the user to return later, e.g., once they know their blood sugar levels. In some embodiments, the device does not prompt the user to confirm they know their numbers, but includes a selection for indicating they do not know a value when asking the subject for a particular value.

If the subject indicates they know their blood sugar levels, the device proceeds with the qualification processing, prompting (702) the subject to acknowledge a privacy notice. Since the present disclosure requires the subject to know and input sensitive medical information (e.g., information only the subject and a medical practitioner have access to), privacy of this information is important. Once the subject has acknowledged they have the requisite privacy for continuing, the process continues.

The device prompts the subject to provide information about their pregnancy status and then applies (706) the answer received from the subject to a pregnancy filter. When the pregnancy filter is fired (e.g., when the answer indicates the subject is pregnant, breastfeeding, or planning to become pregnant), the device terminates (703) the qualification process without authorizing provision of the metformin pharmaceutical agent and, optionally, transmits advice to the user as to why they should not take the metformin pharmaceutical agent.

When the pregnancy filter is not fired, the device proceeds with the qualification process, prompting the subject to provide information indicating whether they have a kidney problem and then applies (708) the answer received from the subject to a kidney function filter. When the kidney function filter is fired (e.g., when the answer indicates that the subject has a kidney problem), the device terminates (703) the qualification process without authorizing provision of the metformin pharmaceutical agent and, optionally, transmits advice to the user why they should not take the metformin pharmaceutical agent.

When the kidney function filter is not fired, the device proceeds with the qualification process, prompting the subject to provide information indicating a ketoacidosis status and then applies (710) the answer received from the subject to a ketoacidosis filter. When the ketoacidosis filter is fired (e.g., when the answer indicates the subject has ketoacidosis), the device terminates (703) the qualification process without authorizing provision of the metformin pharmaceutical agent and, optionally, transmits advice to the user why they should not take the metformin pharmaceutical agent.

When the ketoacidosis filter is not fired, the device proceeds with the qualification process, prompting the subject to provide information indicating an alcohol consumption status and then applies (712) the answer received from the subject to an alcohol consumption filter. When the alcohol consumption filter is fired (e.g., when the answer indicates that the subject abuses alcohol), the device terminates (703) the qualification process without authorizing provision of the metformin pharmaceutical agent and, optionally, transmits advice to the user why they should not take the metformin pharmaceutical agent.

When the alcohol consumption filter is not fired, the device proceeds with the qualification process, prompting the subject to provide information indicating their age and then applies (714) the answer received from the subject to an age filter. When the age filter is fired (e.g., when the answer indicates that the subject is younger than eighteen years old), the device terminates (703) the qualification process without authorizing provision of the metformin pharmaceutical agent and, optionally, transmits advice to the user why they should not take the metformin pharmaceutical agent and/or to return once they have obtained an age at which it would be appropriate to take a metformin composition.

When the age filter is not fired, the device proceeds with the qualification process, prompting the subject to provide information indicating a Type 1 diabetes status and then applies (716) the answer received from the subject to a Type 1 diabetes filter. When the Type 1 diabetes filter is fired (e.g., when the answer indicates that the subject has Type 1 diabetes), the device terminates (703) the qualification process without authorizing provision of the metformin pharmaceutical agent and, optionally, transmits advice to the user why they should not take the metformin pharmaceutical agent.

When the Type 1 diabetes filter is not fired, the device proceeds with the qualification process, prompting the subject to provide information indicating a lactic acidosis status and then applies (718) the answer received from the subject to a lactic acidosis filter. When the lactic acidosis filter is fired (e.g., when the answer indicates that the subject has lactic acidosis), the device terminates (703) the qualification process without authorizing provision of the metformin pharmaceutical agent and, optionally, transmits advice to the user why they should not take the metformin pharmaceutical agent.

When the lactic acidosis filter is not fired, the device proceeds with the qualification process, prompting the subject to provide information indicating their blood sugar level and then applies (720) the answer received from the subject to a blood sugar filter. When the blood sugar filter is fired (e.g., when the answer indicates that the subject has a blood sugar level that is either too low (e.g., below a pre-diabetic and/or diabetic level, e.g., less than 6.5% glycated hemoglobin) or too high (e.g., above a threshold at which a stronger, prescription medication would be more appropriate, e.g., greater than 7.5% glycated hemoglobin), the device terminates (705) the qualification process without authorizing provision of the metformin pharmaceutical agent and, optionally, transmits advice to the user why they should not take the metformin pharmaceutical agent (e.g., because they do not need blood lowering medication or because they need a stronger, prescription medication).

When the blood sugar filter is not fired, the device proceeds with the qualification process, prompting the subject to provide information indicating whether they have a liver problem and then applies (722) the answer received from the subject to a liver disease filter. When the liver disease filter is fired (e.g., when the answer indicates the subject has a liver problem), the device initiates (711-1) an override procedure (e.g., creates a record indicating that the user must confirm they have discussed taking a metformin pharmaceutical composition with a health care provider).

The device then proceeds with the qualification process, prompting the subject to provide information indicating whether they have ever had any serious medical issues (e.g., ever had a heart attack, a severe infection, and/or a stroke) and then applies (724) the answer received from the subject to a medical issue filter. When the medical filter is fired (e.g., when the answer indicates the subject has had a heart attack, the subject has had a severe infection, or the subject has had a stroke), the device initiates (711-2) an override procedure (e.g., creates a record indicating that the user must confirm they have discussed taking a metformin pharmaceutical composition with a health care provider).

The device then proceeds with the qualification process, prompting the subject to provide information regarding recent and/or future surgeries and then applies (726) the answer received from the subject to a surgery filter. When the surgery filter is fired (e.g., when the answer indicates the subject has recently undergone surgery, the subject is planning on undergoing surgery, or the subject is planning on having an x-ray procedure that includes injection of a contrast agent), the device initiates (711-3) an override procedure (e.g., creates a record indicating that the user must confirm they have discussed taking a metformin pharmaceutical composition with a health care provider).

The device then proceeds with the qualification process, prompting the subject to provide information indicating whether they have a history of dehydration and then applies (728) the answer received from the subject to a dehydration filter. When the dehydration filter is fired (e.g., when the answer indicates the subject has a history of dehydration), the device initiates (780-4) an override procedure (e.g., creates a record indicating that the user must confirm they have discussed taking a metformin pharmaceutical composition with a health care provider).

The device then proceeds with the qualification process, prompting the subject to provide information indicating whether they are already taking a diabetes medication (e.g., a different diabetes medication) and then applies (730) the answer received from the subject to a diabetes medication filter. When the diabetes medication filter is fired (e.g., when the answer indicates the subject is already taking a diabetes medication), the device initiates (711-5) an override procedure (e.g., creates a record indicating that the user must confirm they have discussed taking a metformin pharmaceutical composition with a health care provider).

The device then proceeds with the qualification process, determining (713) whether the override procedure has been triggered (e.g., by firing of any one of the liver disease filter, the medical issue filter, the surgery filter, the dehydration filter, and the diabetes medication filter). If the override procedure has been triggered, the device prompts (717) the user to confirm that they have spoken with a medical professional about taking a metformin pharmaceutical composition (e.g., in view of the underlying risk factor that triggered any one of the liver disease filter, the medical issue filter, the surgery filter, the dehydration filter, or the diabetes medication filter), e.g., and that the medical professional recommended (or did not advise against) taking the metformin pharmaceutical composition. If the user's response indicates they have not spoken with a medical professional or the medical professional did not recommend taking the metformin pharmaceutical composition, the device terminates (705) the process and, optionally, transmits advice for the subject to consult a medical professional.

If the override procedure was not triggered, or the override procedure was triggered and the subject's response indicates that they discussed taking a metformin pharmaceutical composition with a medical professional (e.g., in view of the underlying risk factor triggering the override procedure), e.g., and the medical professional recommended taking (or did not advise against) a metformin pharmaceutical composition, the device proceeds with the qualification process, prompting (734) the subject to confirm their answers. If the user confirms their answers, the device transmits (735) a drug facts label for the metformin pharmaceutical composition and prompts the user to read the drug facts label. If the subject confirms they have read the drug facts label (and or the device determines that the user scrolled through the drug facts label), the device proceeds to authorize (736) purchase of the metformin pharmaceutical composition.

FIG. 8 illustrates an example method for qualifying a subject for a refill of an over-the-counter metformin pharmaceutical composition (e.g., following a prescription from a medical professional or initial qualification by a method described herein). Referring to FIG. 8, the device prompts (802) the subject to confirm they know their blood sugar level. When the user indicates they do not know their blood sugar level, the device terminates (801) the process without authorizing provision of the metformin pharmaceutical agent, optionally transmitting advice for the user to return once they know their blood sugar. In some embodiments, e.g., where the user has recently begun taking the metformin pharmaceutical compound and/or the device has access to a recent a blood sugar measurement from the subject, the device bypasses prompting the user to confirm that they know their blood sugar levels. When the user indicates they do know their blood sugar levels, the device prompts (804) the subject to acknowledge a privacy notice.

Once the subject has acknowledged they have the requisite privacy for continuing, the device proceeds with the qualification process, prompting the subject to provide information about their pregnancy status and then applies (806) the answer received from the subject to a pregnancy filter. When the pregnancy filter is fired (e.g., when the answer indicates the subject is pregnant, breastfeeding, or planning to become pregnant), the device creates (821-1) a record of an adverse event (e.g., aggregated in an adverse event data store having records of adverse events from a plurality of users), terminates (801) the qualification process and, optionally, transmits advice to return later (e.g., when the user in no longer pregnant, breastfeeding, or planning to become pregnant).

When the pregnancy filter is not fired, the device proceeds with the qualification process, prompting the subject to provide information indicating whether the subject has developed a kidney problem since receiving their last provision of the metformin pharmaceutical composition and then applies (808) the answer received from the subject to a kidney disease filter. When the kidney disease filter is fired (e.g., when the subject's answer indicates the subject has developed a kidney problem since receiving their last provision of the metformin pharmaceutical composition), the device creates (821-2) a record of an adverse event (e.g., aggregated in an adverse event data store having records of adverse events from a plurality of users) and terminates (803) the qualification process and, optionally, transmits advice to the user as to why they should not take the metformin pharmaceutical composition.

When the kidney disease filter is not fired, the device proceeds with the qualification process, prompting the subject to provide information about alcohol consumption and then applies (810) the answer received from the subject to an alcohol consumption filter. When the alcohol consumption filter is fired (e.g., when the answer indicates that the subject abuses alcohol), the device terminates (803) the qualification process and, optionally, transmits advice to the user as to why they should not take the metformin pharmaceutical composition.

When the alcohol consumption filter is not fired, the device proceeds with the qualification process, prompting the subject to provide information indicating whether the subject has developed ketoacidosis since receiving their last provision of the metformin pharmaceutical composition and then applies (812) the answer received from the subject to a ketoacidosis symptom filter. When the ketoacidosis symptom filter is fired (e.g., when the subject's answer indicates the subject has developed ketoacidosis since receiving their last provision of the metformin pharmaceutical composition), the device creates (821-3) a record of an adverse event (e.g., aggregated in an adverse event data store having records of adverse events from a plurality of users), terminates (803,805) the qualification process and, optionally, transmits advice to the user as to why they should not take the metformin pharmaceutical composition and/or to seek medical attention.

When the ketoacidosis symptom filter is not fired, the device proceeds with the qualification process, prompting the subject to provide information indicating whether the subject has developed lactic acidosis since receiving their last provision of the metformin pharmaceutical composition and then applies (814) the answer received from the subject to a lactic acidosis symptom filter. When the lactic acidosis symptom filter is fired (e.g., when the subject's answer indicates the subject has developed lactic acidosis since receiving their last provision of the metformin pharmaceutical composition), the device creates (821-4) a record of an adverse event (e.g., aggregated in an adverse event data store having records of adverse events from a plurality of users), terminates (803,805) the qualification process and, optionally, transmits advice to the user as to why they should not take the metformin pharmaceutical composition and/or to seek medical attention.

When the lactic acidosis symptom filter is not fired, the device proceeds with the qualification process, prompting the subject to provide information indicating whether the subject has experienced an illness causing vomiting, diarrhea, or fever since receiving their last provision of the metformin pharmaceutical composition and then applies (816) the answer received from the subject to an illness filter. When the illness filter is fired (e.g., when the subject's answer indicates the subject has experienced an illness causing vomiting, diarrhea, or fever since receiving their last provision of the metformin pharmaceutical composition), the device terminates (803,805) the qualification process and, optionally, transmits advice to the user as to why they should not take the metformin pharmaceutical composition to seek medical attention.

When the illness filter is not fired, the device proceeds with the qualification process, prompting the subject to provide information indicating whether the subject has developed a liver problem since receiving their last provision of the metformin pharmaceutical composition and then applies (818) the answer received from the subject to a liver disease filter. When the liver disease filter is fired (e.g., when the answer indicates the subject has developed a liver problem since receiving their last provision of the metformin pharmaceutical composition), the device creates (821-5) a record of an adverse event (e.g., aggregated in an adverse event data store having records of adverse events from a plurality of users) and initiates (811-1) an override procedure (e.g., creates a record indicating that the user must confirm they have discussed taking a metformin pharmaceutical composition with a health care professional).

The device then proceeds with the qualification process, prompting the subject to provide information indicating whether the subject has experienced a severe medical issue since receiving their last provision of the metformin pharmaceutical composition and then applies (820) the answer received from the subject to a medical issue filter. When the medical issue filter is fired (e.g., when the answer indicates that the subject has had a heart attack, the subject has had a severe infection, or the subject has had a stroke, since receiving their last provision of the metformin pharmaceutical composition), the device creates (821-6) a record of an adverse event (e.g., aggregated in an adverse event data store having records of adverse events from a plurality of users) and initiates (811-2) an override procedure (e.g., creates a record indicating that the user must confirm they have discussed taking a metformin pharmaceutical composition with a health care professional).

The device then proceeds with the qualification process, prompting the subject to provide information regarding their surgery status and then applies (822) the answer received from the subject to a surgery filter. When the surgery filter is fired (e.g., when the answer indicates that the subject has undergone surgery since receiving their last provision of the metformin pharmaceutical composition, the subject is planning on undergoing surgery, or the subject is planning on having an x-ray procedure that includes injection of a contrast agent), the device initiates (811-3) an override procedure (e.g., creates a record indicating that the user must confirm they have discussed taking a metformin pharmaceutical composition with a health care professional).

The device then proceeds with the qualification process, prompting the subject to provide information indicating whether the subject has experienced dehydration since receiving their last provision of the metformin pharmaceutical composition and then applies (824) the answer received from the subject to a dehydration filter. When the dehydration filter is fired (e.g., when the answer indicates that the subject has experienced dehydration since receiving their last provision of the metformin pharmaceutical composition), the device creates (821-7) a record of an adverse event (e.g., aggregated in an adverse event data store having records of adverse events from a plurality of users) and initiates (811-4) an override procedure (e.g., creates a record indicating that the user must confirm they have discussed taking a metformin pharmaceutical composition with a health care professional).

The device then proceeds with the qualification process, prompting the subject to provide information indicating whether the subject is taking another diabetes medication and then applies (826) the answer received from the subject to a diabetes medication filter. When the diabetes medication filter is fired (e.g., when the answer indicates that the subject is taking another diabetes medication), the device initiates (811-5) an override procedure (e.g., creates a record indicating that the user must confirm they have discussed taking a metformin pharmaceutical composition with a health care professional).

The device then proceeds with the qualification process, determining whether the subject has been taking the metformin pharmaceutical composition for at least a threshold amount of time (e.g., at least three months since receiving their first provision of the metformin pharmaceutical composition and every six months thereafter), e.g., without providing a blood sugar level. If the device determines that a threshold amount of time has passed (e.g., since a last stored blood sugar level measurement), the device prompts the subject to provide information about their blood sugar level (e.g., an actual value or whether it is below a threshold level) and applies (828) the answer received from the subject to a blood sugar filter. When the blood sugar filter is fired (e.g., when the answer indicates that the subject has a blood sugar level above a threshold level, e.g., 7% glycated hemoglobin) the device terminates (805) the qualification process and, optionally, transmits advice to the user to seek medical attention.

When the device determines that a threshold amount of time has not passed, and/or the blood sugar filter is not fired, the device proceeds with the qualification process, determining (832) whether the override procedure has been triggered (e.g., by firing of any one of the liver disease filter, the medical issue filter, the surgery filter, the dehydration filter, or the diabetes medication filter). If the override procedure has been triggered, the device prompts (817) the user to confirm that they have spoken with a medical professional about taking a metformin pharmaceutical composition (e.g., in view of the underlying risk factor that triggered the respective filter), e.g., and the medical professional recommended (or did not advise against) taking the metformin pharmaceutical composition. If the user's response indicates they have not spoken with a medical professional or the medical professional did not recommend taking the metformin pharmaceutical composition, the device terminates (805) the process and, optionally, transmits advice for the subject to consult a medical professional.

If the override procedure was not triggered, or the override procedure was triggered and the subject's response indicated that the user spoke with a medical professional, e.g., who recommended, or did not advise against, taking a metformin pharmaceutical composition (e.g., in view of the underlying risk factor triggering the override procedure), the device proceeds with the re-qualification process, prompting (834) the subject to confirm their answers. If the user confirms their answers, the device transmits (831) a drug facts label for the metformin pharmaceutical composition and prompts the user to read the drug facts label. If the subject confirms they have read the drug facts label, the device proceeds to authorize (836) purchase of the metformin pharmaceutical composition Specific Embodiments In one aspect, the disclosure provides methods, software, and computer systems for qualifying a human subject for over-the-counter delivery of a biguanide antihyperglycemic pharmaceutical composition for lowering blood sugar levels, e.g., thereby, treating Type 2 diabetes and/or maintaining sub-diabetic blood sugar levels. In one embodiment, a computer system (e.g., computer system 250 in FIG. 2) includes instructions for conducting a survey of the subject (e.g., including survey questions 208 and 212 administered via assessment module 252 in FIG. 2) to obtain information about the subject necessary to run against at least two series of filters (e.g., filters 216 and 222 in first filter category class 214-1 and second filter category class 220-1, respectively, in FIG. 2). The computer system also includes instructions for running the survey results against the filters. Filters 216 in the first series of filters 214 prevent authorization of a provision of the OTC biguanide antihyperglycemic where the subject's survey results identify a contraindication for the OTC biguanide antihyperglycemic. Filters 222 in the second series of filters 220 generate a warning 226 where the subject's survey results identify a risk factor for the OTC biguanide antihyperglycemic. In some embodiments, the warning 226 includes a prompt requiring the subject to confirm they have discussed the risk factor with a physician in order to proceed with qualification for the OTC biguanide antihyperglycemic.

In one aspect, the disclosure provides methods, software, and computer systems for re-qualifying a human subject for over-the-counter delivery of a biguanide antihyperglycemic pharmaceutical composition for lowering blood sugar, e.g., thereby, treating diabetes. In one embodiment, a computer system (e.g., computer system 250 in FIG. 2) includes instructions for conducting a survey of the subject (e.g., administered via reassessment module 254 in FIG. 2) to obtain information about the subject necessary to run against at least two series of filters. The computer system also includes instructions for running the survey results against the filters. Filters 216 in the third series 214-2 of filters prevent authorization for delivery of the OTC biguanide antihyperglycemic composition where the subject's survey results identify a contraindication for the OTC biguanide antihyperglycemic composition. Filters 222 in the fourth series of filters 220-2 generate a warning 226 where the subject's survey results identify a risk factor for the OTC biguanide antihyperglycemic composition. In some embodiments, the warning 226 includes a prompt requiring the subject to confirm they have discussed the risk factor with a physician in order to proceed with qualification for the OTC biguanide antihyperglycemic composition.

In one aspect, the disclosure provides a computer system for qualifying a human subject for over-the-counter delivery of a metformin pharmaceutical composition to lower blood sugar levels. The computer system comprising one or more processors and a memory, the memory comprising non-transitory instructions which, when executed by the one or more processor, perform a method for qualifying a human subject for over-the-counter delivery of the metformin pharmaceutical composition. The method includes conducting a first survey of the subject thereby obtaining a first plurality of survey results necessary to run against a first plurality of filters of a first category class and a second plurality of filters of a second category class. The method also includes running all or a portion of the first plurality of survey results against a first plurality of filters of a first category class, wherein, when a respective filter in the first plurality of filters is fired, the subject is deemed not qualified for delivery of the metformin pharmaceutical composition and the method is terminated without delivery of the metformin pharmaceutical composition to the subject. The method also includes running all or a portion of the first plurality of survey results against a second plurality of filters of a second category class, wherein, when a respective filter in the second plurality of filters is fired, the subject is provided with a warning corresponding to the respective filter. The method also includes obtaining acknowledgment from the subject for the warning issued to the subject by any filter in the second plurality of filters. The method also includes proceeding with a fulfillment process when no filter in the first plurality of filters has been fired and the subject has acknowledged each warning associated with each filter in the second plurality of filters that was fired. The fulfillment process includes: storing an indication in a subject profile of an initial order for the metformin pharmaceutical composition, communicating an over-the-counter drug facts label for the metformin pharmaceutical composition to the subject, and authorizing, upon confirmation from the subject that the over-the-counter drug facts label has been received and read, provision of the metformin pharmaceutical composition to the subject. In some embodiments, the authorization includes a destination associated with the subject.

In some embodiments, the first plurality of survey results includes a plurality of survey results selected from the survey results listed in Table 1. In one embodiment, the first plurality of survey results includes: whether the subject is any one of pregnant, breastfeeding, or planning to become pregnant, whether the subject has a kidney problem, a ketoacidosis status of the subject, an alcohol consumption status of the subject, an age of the subject, a Type 1 diabetes status of the subject, a lactic acidosis status of the subject, a blood sugar level of the subject, whether the subject has a liver problem, whether the subject has ever had a heart attack, severe infection, or stroke, a surgery status of the subject, whether the subject has a history of dehydration, and whether the subject is already taking a diabetes medication.

In some embodiments, the first plurality of filters includes a plurality of filters selected from the filters listed in Table 2. In one embodiment, the first plurality of filters includes a pregnancy filter, a kidney function filter, a ketoacidosis filter, an alcohol consumption filter, an age filter, a Type 1 diabetes filter, a lactic acidosis filter, and a blood sugar level filter.

In some embodiments, the second plurality of filters includes a plurality of filters selected from the filters listed in Table 3. In one embodiment, the second plurality of filters includes a liver disease filter, a medical issue filter, a surgery filter, a dehydration filter, and a diabetes medication filter.

In some embodiments, the first and second plurality of filters includes filters selected from the filters listed in Table 8. In some embodiments, the first plurality of filters of the first category class include a first sub-plurality of the filters listed in Table 8, for example, 2, 3, 4, 5, 6, 7, 8, 9, 10, 11, 12, or all 13 of the filters listed in Table 8, and the second plurality of filters of the first category class include a second sub-plurality of the filters listed in Table 8, which is different from the first sub-plurality of filters, for example, 2, 3, 4, 5, 6, 7, 8, 9, 10, 11, 12, or all 13 of the filters listed in Table 8. In some embodiments, each of the filters in the first sub-plurality of filters is different from each of the filters in the second sub-plurality of filters (e.g., no filter listed in Table 8 is included in both the first sub-plurality and the second sub-plurality of filters). In some embodiments, a system for qualifying a subject for delivery of an over-the-counter metformin pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 8, e.g., at least 2, 3, 4, 5, 6, 7, 8, 9, 10, 11, 12, or all 13 of the filters listed in Table 8. In some embodiments, where a filter listed in Table 8 corresponds to a filter listed in Table 2 or Table 3, a threshold level sufficient to fire the corresponding filter listed in Table 2 or Table 3, as described in detail above, is sufficient to fire the filter listed in Table 8.

TABLE 8

Example filters for qualifying a subject for an over-the-counter provision of a metformin pharmaceutical composition.

| Filter | Example Criteria |
| --- | --- |
| 1b | a pregnancy filter |
| 2b | a kidney function status filter |
| 3b | a ketoacidosis filter |
| 4b | an alcohol consumption filter |
| 5b | an age filter |
| 6b | a Type 1 diabetes filter |
| 7b | a lactic acidosis filter |
| 8b | a blood sugar level filter |
| 9b | a liver disease filter |
| 10b | a medical issue filter |
| 11b | a surgery filter |
| 12b | a dehydration filter |
| 13b | a diabetes medication filter |

In one aspect, the disclosure provides methods, software, and computer systems for qualifying a human subject for a re-order of an over-the-counter provision of a metformin pharmaceutical composition for lowering blood sugar levels, e.g., thereby, treating Type 2 diabetes and/or maintaining sub-diabetic blood sugar levels. In one embodiment, a computer system includes instructions, responsive to receiving a re-order request from the subject for the metformin pharmaceutical composition, for performing a re-fulfillment procedure comprising conducting a second survey of the subject, thereby obtaining a second plurality of survey results necessary to run against a third plurality of filters of a first category class and a fourth plurality of filters of a second category class. The method also includes running all or a portion of the second plurality of survey results against a third plurality of filters of a first category class, wherein, when a respective filter in the third plurality of filters is fired, the subject is deemed not qualified for delivery of the metformin pharmaceutical composition and the method is terminated without delivery of the metformin pharmaceutical composition to the subject. The method also includes running all or a portion of the second plurality of survey results against a fourth plurality of filters of a second category class, where, when a respective filter in the fourth plurality of filters is fired, the subject is provided with a warning corresponding to the respective filter. The method also includes obtaining acknowledgment from the subject for the warning issued to the subject by any filter in the fourth plurality of filters. The method also includes proceeding with a re-fulfillment process when no filter in the third plurality of filters has been fired and the subject has acknowledged each warning associated with each filter in the fourth plurality of filters that was fired. The re-fulfillment process includes: storing an indication in a subject profile of a re-order for the metformin pharmaceutical composition, communicating the over-the-counter drug facts label for the metformin pharmaceutical composition to the subject, and authorizing, upon confirmation from the subject that the over-the-counter drug facts label has been received and read, provision of the metformin pharmaceutical composition to the subject.

In some embodiments, the third series of filters includes one or more filters listed in Table 5. In some embodiments, the third plurality of filters includes a pregnancy filter, a kidney disease filter, an alcohol consumption filter, a ketoacidosis symptom filter, an age filter, a lactic acidosis symptom filter, an illness filter, and a blood sugar maintenance filter.

In some embodiments, the fourth series of filters includes one or more filters listed in Table 6. In some embodiments, the fourth plurality of filters includes a liver disease filter, a medical issue filter, a surgery filter, a dehydration filter, and a diabetes medication filter.

In some embodiments, the third and fourth plurality of filters includes filters selected from the filters listed in Table 9. In some embodiments, the third plurality of filters of the first category class include a third sub-plurality of the filters listed in Table 9, for example, 2, 3, 4, 5, 6, 7, 8, 9, 10, 11, or all 12 of the filters listed in Table 9, and the fourth plurality of filters of the first category class include a fourth sub-plurality of the filters listed in Table 9, which is different from the third sub-plurality of filters, for example, 2, 3, 4, 5, 6, 7, 8, 9, 10, 11, or all 12 of the filters listed in Table 9. In some embodiments, each of the filters in the third sub-plurality of filters is different from each of the filters in the fourth sub-plurality of filters (e.g., no filter listed in Table 9 is included in both the first sub-plurality and the second sub-plurality of filters). In some embodiments, a system for qualifying a subject for delivery of an over-the-counter metformin pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 9, e.g., at least 2, 3, 4, 5, 6, 7, 8, 9, 10, 11, or all 12 of the filters listed in Table 9. In some embodiments, where a filter listed in Table 9 corresponds to a filter listed in Table 2, Table 3, Table 5, or Table 6, a threshold level sufficient to fire the corresponding filter listed in Table 2, Table 3, Table 5, or Table 6, as described in detail above, is sufficient to fire the filter listed in Table 9.

TABLE 9

Example filters for re-qualifying a subject for an over-the-counter provision of a metformin pharmaceutical composition

| Filter | Example Criteria |
| --- | --- |
| 1b | a pregnancy filter |
| 2b | a kidney disease filter |
| 3b | an alcohol consumption filter |
| 4b | a ketoacidosis symptom filter |
| 5b | a lactic acidosis symptom filter |
| 6b | an illness filter |
| 7b | a blood sugar maintenance filter |
| 8b | a liver disease filter |
| 9b | a medical issue filter |
| 10b | a surgery filter |
| 11b | a dehydration filter |
| 12b | a diabetes medication filter |

In one aspect, the present disclosure provides a computer system for qualifying a human subject for over-the-counter delivery of a metformin pharmaceutical composition for lowering blood sugar levels, the computer system comprising one or more processors and a memory, the memory comprising non-transitory instructions which, when executed by the one or more processor, perform a method comprising: a) conducting a first survey of the subject thereby obtaining a first plurality of survey results, wherein the first plurality of survey results indicates: whether the subject is any one of pregnant, breastfeeding, or planning to become pregnant, whether the subject has a kidney problem, a ketoacidosis status of the subject, an alcohol consumption status of the subject, an age of the subject, a Type 1 diabetes status of the subject, a lactic acidosis status of the subject, a blood sugar level of the subject, whether the subject has a liver problem, whether the subject has ever had a heart attack, severe infection, or stroke, a surgery status of the subject, whether the subject has a history of dehydration, and whether the subject is taking a diabetes medication; b) running all or a portion of the first plurality of survey results against a first plurality of filters of a first category class, wherein, when a respective filter in the first plurality of filters is fired, the subject is deemed not qualified for delivery of the metformin pharmaceutical composition and the method is terminated without delivery of the metformin pharmaceutical composition to the subject, wherein the first plurality of filters comprises: a first pregnancy filter that is fired at least when the first plurality of survey results indicates that the subject is pregnant or the subject is breastfeeding, a kidney function filter that is fired at least when the first plurality of survey results indicates that the subject has a kidney problem, a first ketoacidosis filter that is fired at least when the first plurality of survey results indicates that the subject has ketoacidosis, a first alcohol consumption filter, an age filter, a Type 1 diabetes filter that is fired at least when the first plurality of survey results indicates that the subject has Type 1 diabetes, a lactic acidosis filter that is fired at least when the first plurality of survey results indicates that the subject has lactic acidosis, and a first blood sugar level filter that is fired at least when the first plurality of survey results indicates that the subject has a blood sugar level that is either below a first floor blood sugar level or above a ceiling blood sugar level; c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises: a first liver disease filter that is fired at least when the first plurality of survey results indicates that the subject has a liver problem, a first medical issue filter that is fired at least when the first plurality of survey results indicates that the subject has had a heart attack, the subject has had a severe infection, or the subject has had a stroke, a first surgery filter that is fired at least when the first plurality of survey results indicates that the subject has recently undergone surgery, the subject is planning on undergoing surgery, or the subject is planning on having an x-ray procedure that includes injection of a contrast agent, a first dehydration filter that is fired at least when the first plurality of survey results indicates that the subject has developed symptoms of dehydration, and a first diabetes medication filter that is fired at least when the first plurality of survey results indicates that the subject is taking a diabetes medication; d) obtaining acknowledgment from the subject for the warning issued to the subject by any filter in the second plurality of filters; and e) proceeding with a fulfillment process when no filter in the first plurality of filters has been fired and the subject has acknowledged each warning associated with each filter in the second plurality of filters that was fired, wherein the fulfillment process comprises: storing an indication in a subject profile of an initial order for the metformin pharmaceutical composition, communicating an over-the-counter drug facts label for the metformin pharmaceutical composition to the subject, and authorizing, upon confirmation from the subject that the over-the-counter drug facts label has been received and read, provision of the metformin pharmaceutical composition to the subject.

In some embodiments of the aspects disclosed above, the metformin pharmaceutical composition is an extended release formulation of metformin hydrochloride.

In some embodiments of the aspects disclosed above, upon confirmation from the subject that the over the counter drug facts label has been received and read, the subject is authorized for provision of a dosage of from 500 mg to 1000 mg per day of the metformin pharmaceutical composition.

In some embodiments of the aspects disclosed above, upon confirmation from the subject that the over the counter drug facts label has been received and read, the subject is authorized for provision of a dosage of 500 mg per day of the metformin pharmaceutical composition.

In some embodiments of the aspects disclosed above, the first pregnancy filter is also fired when the first plurality of survey results indicates that the subject plans to become pregnant within a predetermined period of time.

In some embodiments of the aspects disclosed above, the alcohol consumption filter is fired when the first plurality of survey results indicates that the subject, on average, consumes at least a predetermined number of alcoholic drinks over a predetermined period of time.

In some embodiments of the aspects disclosed above, the age filter is fired when the first plurality of survey results indicates that the subject is less than eighteen years old.

In some embodiments of the aspects disclosed above, the first floor blood sugar level used in the first blood sugar level filter is 6.5% glycated hemoglobin. Furthermore, in some embodiments of the aspects disclosed above the first ceiling blood sugar level used in the first blood sugar level filter is 7.5% glycated hemoglobin.

In some embodiments of the aspects disclosed above, the first plurality of survey results further comprises whether the subject is allergic to the metformin pharmaceutical composition, and the first plurality of filters includes an adverse reaction filter that is fired when the first plurality of survey results indicates that the subject is allergic to the metformin blocker pharmaceutical composition.

In some embodiments of the aspects disclosed above, the warning corresponding to a respective filter in the second plurality of filters comprises a prompt for the subject to indicate whether they have discussed the risk factor underlying the respective filter in the second plurality of filters that was fired with a health care provider; and acknowledgement is obtained from the subject when the subject indicates that they have discussed the risk factor underlying the respective filter in the second plurality of filters that was fired with a health care provider.

In some embodiments of the aspects disclosed above, the fulfillment process further comprises: storing a destination associated with the subject in the subject profile.

In some embodiments of the aspects disclosed above, the fulfillment process further comprises: coordinating shipping of the metformin pharmaceutical composition to a physical address associated with the subject.

In some embodiments of the aspects disclosed above, the method further comprises: f) responsive to receiving a re-order request from the subject for the metformin pharmaceutical composition, performing a re-fulfillment procedure comprising: (i) conducting a second survey of the subject thereby obtaining a second plurality of survey results, wherein the second plurality of survey results indicates: whether the subject is one of pregnant, breastfeeding, or planning to become pregnant, whether the subject has developed a kidney problem since receiving their last provision of the metformin pharmaceutical composition, an alcohol consumption status of the subject, whether the subject has developed ketoacidosis since receiving their last provision of the metformin pharmaceutical composition, whether the subject has developed lactic acidosis since receiving their last provision of the metformin pharmaceutical composition, whether the subject has experienced an illness causing vomiting, diarrhea, or fever since receiving their last provision of the metformin pharmaceutical composition, whether the subject has developed a liver problem since receiving their last provision of the metformin pharmaceutical composition, whether the subject has experienced a heart attack, severe infection, or stroke since receiving their last provision of the metformin pharmaceutical composition, a surgery status of the subject, whether the subject has experienced dehydration since receiving their last provision of the metformin pharmaceutical composition, whether the subject is taking another diabetes medication, and a blood sugar level of the subject (e.g., which is, optionally, only obtained when the subject has been taking the metformin pharmaceutical composition for at least a threshold amount of time); (ii) running all or a portion of the second plurality of survey results against a third plurality of filters of the first category class, wherein, when a respective filter in the third plurality of filters is fired, the subject is deemed not qualified for the metformin pharmaceutical composition and the re-fulfillment process is terminated without delivery of the metformin pharmaceutical composition to the subject, wherein the third plurality of filters comprise: a second pregnancy filter that is fired at least when the second plurality of survey results indicates that the subject is pregnant or the subject is breastfeeding, a kidney disease filter that is fired at least when the second plurality of survey results indicates that the subject has developed a kidney problem since receiving their last provision of the metformin pharmaceutical composition, a second alcohol consumption filter, a second ketoacidosis filter that is fired at least when the second plurality of survey results indicates that the subject has developed ketoacidosis since receiving their last provision of the metformin pharmaceutical composition, a lactic acidosis symptom filter that is fired at least when the second plurality of survey results indicates that the subject has developed lactic acidosis since receiving their last provision of the metformin pharmaceutical composition, an illness filter that is fired at least when the second plurality of survey results indicates that the user has experienced an illness causing vomiting, diarrhea, or fever since receiving their last provision of the metformin pharmaceutical composition, and a blood sugar maintenance filter that is fired at least when the second plurality of survey results indicates that the subject has a blood sugar level of at least a second ceiling blood sugar level (e.g., that is, optionally, only applied when the subject has been taking the metformin pharmaceutical composition for a threshold amount of time); and (iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises: a second liver disease filter that is fired at least when the second plurality of survey results indicates that the subject has developed a liver problem since receiving their last provision of the metformin pharmaceutical composition, a second medical issue filter that is fired at least when the second plurality of survey results indicates that the subject has had a heart attack, the subject has had a severe infection, or the subject has had a stroke since receiving their last provision of the metformin pharmaceutical composition, a second surgery filter that is fired at least when the second plurality of survey results indicates that the subject has undergone surgery since receiving their last provision of the metformin pharmaceutical composition, the subject is planning on undergoing surgery, or the subject is planning on having an x-ray procedure that includes injection of a contrast agent, a second dehydration filter that is fired at least when the second plurality of survey results indicates that the subject has experienced dehydration since receiving their last provision of the metformin pharmaceutical composition, and a second diabetes medication filter that is fired at least when the second plurality of survey results indicates that the subject is taking another diabetes medication; (iv) obtaining acknowledgment from the subject for the warning issued to the subject by any filter in the fourth plurality of filters; (v) proceeding with the re-fulfillment process when (a) the re-fulfillment process is not already terminated by the firing of a filter in the third plurality of filters and (b) the subject has acknowledged each warning associated with each filter in the fourth plurality of filters that was fired, wherein the re-fulfillment process further comprises: storing an indication in the subject profile of a re-order for the metformin pharmaceutical composition, communicating the over-the-counter drug facts label for the metformin pharmaceutical composition to the subject, and authorizing, upon confirmation from the subject that the over-the-counter drug facts label has been received and read, a re-order provision of the metformin pharmaceutical composition to the subject.

In some embodiments of the aspects disclosed above, the second pregnancy filter is also fired when the second plurality of survey results indicates that the subject plans to become pregnant within a predetermined period of time.

In some embodiments of the aspects disclosed above, the second alcohol consumption filter is fired when the first plurality of survey results indicates that the subject, on average, consumes at least a predetermined number of alcoholic drinks over a predetermined period of time.

In some embodiments of the aspects disclosed above, a symptom of ketoacidosis, which is capable of firing the ketoacidosis filter, is selected from the group consisting of an increase of ketones in the blood of the subject, an increase of ketones in the urine of the subject, nausea, tiredness, vomiting, trouble breather, and abdominal pain.

In some embodiments of the aspects disclosed above, a symptom of lactic acidosis, which is capable of firing the lactic acidosis symptom filter, is selected from the group consisting of cold feelings in the subject's hands or feet, dizziness, lightheadedness, slow or irregular heartbeat, feeling very weak or tired, unusual muscle pain, difficulty breathing, stomach pains, nausea, and vomiting.

In some embodiments of the aspects disclosed above, the second ceiling blood sugar level used in the blood sugar maintenance filter is 7% glycated hemoglobin.

In some embodiments of the aspects disclosed above, the second plurality of survey results further comprises whether the subject has developed side effects associated with the metformin pharmaceutical composition since receiving their last provision of the metformin pharmaceutical composition, and the fourth plurality of filters further comprises a side effect filter that is fired at least when the second plurality of survey results indicates that the subject has developed, since receiving their last provision of the metformin pharmaceutical composition, side effects selected from the group consisting of a metallic taste, diarrhea, nausea, and an upset stomach.

In some embodiments of the aspects disclosed above, the re-fulfillment process further comprises, when a respective filter in the third plurality of filters or fourth plurality of filters is fired, storing a record associated with the firing of the respective filter in an adverse event profile comprising records of filter firing events associated with a plurality of subjects.

In some embodiments of the aspects disclosed above, the lowering blood sugar is to treat Type 2 diabetes and/or maintain sub-diabetic blood sugar levels.

In some embodiments, the disclosure provides methods for lowering blood pressure with an over the counter metformin pharmaceutical composition. The method includes providing a first survey for obtaining a first information set from the human, via a computer system having a processor programed to perform the first survey, where the first information set includes information about the human that relates to potential risk factors and contraindications for the metformin pharmaceutical composition, as described herein. The method also includes applying an algorithm to the first information set, via a computer system having a processor programed to perform the algorithm. The algorithm runs all or a portion of the first information set against a first plurality of filters, where the human is deemed not qualified for treatment with the over the counter metformin pharmaceutical composition for lowering blood pressure when a respective filter in the first plurality of filters is fired and the method is terminated without authorizing provision of the metformin pharmaceutical composition to the human, where the first plurality of filters includes filters related to contraindications of the metformin pharmaceutical composition as described herein. The algorithm also runs all or a portion of the first information set against a second plurality of filters, where, when a respective filter in the second plurality of filters is fired, the human is provided with a warning corresponding to the respective filter, and where the second plurality of filters includes filters related to risk factors for the metformin pharmaceutical composition as described herein. The algorithm also obtains acknowledgment from the human of the risk factor associated with each warning issued to the human by any filter in the second plurality of filters. In some embodiments, the acknowledgement includes confirmation that the human has discussed the risk factor with a physician. The algorithm proceeds with a fulfillment process when (a) no filter in the first plurality of filters has been fired and (b) the human has acknowledged each warning associated with each filter in the second plurality of filters that was fired. The fulfillment process includes storing an indication in a subject profile of an initial order for the metformin pharmaceutical composition, communicating an over the counter drug facts label for the metformin pharmaceutical composition to the human, and authorizing, upon confirmation from the subject that the over the counter drug facts label has been received and read, provision of the metformin pharmaceutical composition to the human, where the authorization includes a destination associated with the subject. In some embodiments, the method also includes treating the human to lower the blood pressure of the human, upon authorization of the provision e.g., by providing access to the metformin pharmaceutical composition to the human and/or by administering the metformin pharmaceutical composition to lower blood pressure in the human.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for lowering blood sugar in a human subject with an over-the-counter metformin pharmaceutical composition, the method comprising:
   A) providing a first survey for obtaining a first plurality of survey results about the subject, via a first computer system having a processor programed to perform the first survey, wherein the first plurality of survey results comprises:
      whether the subject is pregnant or breastfeeding,
      whether the subject has a kidney problem,
      a ketoacidosis status of the subject,
      an alcohol consumption status of the subject,
      an age of the subject,
      a Type 1 diabetes status of the subject,
      a lactic acidosis status of the subject,
      a blood sugar level of the subject,
      whether the subject has a liver problem,
      whether the subject has ever had a heart attack, severe infection, or stroke,
      a surgery status of the subject,
      whether the subject has a history of dehydration, and
      whether the subject is already taking a diabetes medication; and
   B) applying an algorithm to the first plurality of survey results, via a second computer system having a process programed to perform the algorithm, wherein the algorithm:
      i) runs all or a portion of the first plurality of survey results against a first plurality of filters of a first category class, wherein, when a respective filter in the first plurality of filters is fired, the subject is deemed not qualified for of the metformin pharmaceutical composition and the method is terminated without authorizing provision of the metformin pharmaceutical composition to the subject, wherein the first plurality of filters comprises:
         a first pregnancy filter that is fired at least when the first plurality of survey results indicates that the subject is pregnant or the subject is breastfeeding,
         a kidney function filter that is fired at least when the first plurality of survey results indicates that the subject has a kidney problem,
         a ketoacidosis filter that is fired at least when the first plurality of survey results indicates that the subject has ketoacidosis,
         a first alcohol consumption filter,
         an age filter,
         a Type 1 diabetes filter that is fired at least when the first plurality of survey results indicates that the subject has Type 1 diabetes,
         a lactic acidosis filter that is fired at least when the first plurality of survey results indicates that the subject has lactic acidosis, and
         a first blood sugar level filter that is fired at least when the first plurality of survey results indicates that the subject has a blood sugar level that is either a) below a first baseline blood sugar level, or b) above a ceiling blood sugar level;
      ii) runs all or a portion of the first plurality of survey results against a second plurality of filters of a second category class, wherein, when a respective filter in the second plurality of filters is fired, the subject is provided with a warning corresponding to the respective filter, and wherein the second plurality of filters comprises:
         a first liver disease filter that is fired at least when the first plurality of survey results indicates that the subject has a liver problem,
         a first medical issue filter that is fired at least when the first plurality of survey results indicates that the subject has had a heart attack, the subject has had a severe infection, or the subject has had a stroke,
         a first surgery filter that is fired at least when the first plurality of survey results indicates that the subject has recently undergone surgery, the subject is planning on undergoing surgery, or the subject is planning on having an x-ray procedure that includes injection of a contrast agent,
         a first dehydration filter that is fired at least when the first plurality of survey results indicates that the subject has experienced a symptom of dehydration, and
         a first diabetes medication filter that is fired at least when the first plurality of survey results indicates that the subject is taking a diabetes medication;
      iii) obtains acknowledgment from the subject for each warning issued to the subject by any filter in the second plurality of filters; and
      iv) proceeds with a fulfillment process when no filter in the first plurality of filters has been fired and b) the subject has acknowledged each warning associated with each filter in the second plurality of filters that was fired, wherein the fulfillment process comprises:
         storing an indication in a subject profile of an initial order for the metformin pharmaceutical composition,
         communicating an over-the-counter drug facts label for the metformin pharmaceutical composition to the subject, and
         authorizing, upon confirmation from the subject that the over-the-counter drug facts label has been received and read, provision of the metformin pharmaceutical composition to the subject; and C) administering the metformin pharmaceutical composition to the subject after authorization of the provision.

2. The method of claim 1, wherein the metformin pharmaceutical composition comprises metformin hydrochloride.

3. The method of claim 2, wherein the subject is administered a dosage of from 500 mg to 1000 mg per day of metformin hydrochloride.

4. The method of claim 2, wherein the subject is administered a dosage of 500 mg per day of metformin hydrochloride.

5. The method of claim 1, wherein the algorithm also fires the first pregnancy filter when the first plurality of survey results indicates that the subject plans to become pregnant within a predetermined period of time.

6. The method of claim 1, wherein the algorithm fires the first alcohol consumption filter when the first plurality of survey results indicates that the subject, on average, consumes at least a predetermined number of alcoholic drinks over a predetermined period of time.

7. The method of claim 1, wherein the algorithm fires the age filter when the first plurality of survey results indicates that the subject is less than eighteen years old.

8. The method of claim 1, wherein the first baseline blood sugar level used in the first blood sugar level filter is 6.5% glycated hemoglobin.

9. The method of claim 1, wherein the ceiling blood sugar level used in the first blood sugar level filter is 7.5% glycated hemoglobin.

10. The method of claim 1, wherein:
the first plurality of survey results further comprises whether the subject is allergic to the metformin pharmaceutical composition, and
the first plurality of filters includes an adverse reaction filter, wherein the algorithm fires when the first plurality of survey results indicates that the subject is allergic to the metformin pharmaceutical composition.

11. The method of claim 1, wherein:
the warning corresponding to a respective filter in the second plurality of filters comprises a prompt for the user to indicate whether they have discussed the risk factor underlying the respective filter in the second plurality of filters that was fired with a health care provider; and
acknowledgement is obtained from the subject when the subject indicates that they have discussed the risk factor underlying the respective filter in the second plurality of filters that was fired with a health care provider.

12. The method of claim 1, wherein the fulfillment process further comprises:
storing a destination associated with the subject in the subject profile.

13. The method of claim 1, wherein the fulfillment process further comprises:
coordinating shipping of the metformin pharmaceutical composition to a physical address associated with the subject.

14. The method of claim 1 further comprising:
D) receiving a re-order request from the subject for the metformin pharmaceutical composition via a third computer system having a processor programed to receive the re-order request; and E) performing a re-fulfillment procedure via a fourth computer system having a processor programed to perform the re-fulfillment procedure, the re-fulfillment procedure comprising:
i) providing a second survey for obtaining a second plurality of survey results about the subject, wherein the second plurality of survey results comprises:
whether the subject is pregnant or breastfeeding,
whether the subject has experienced a kidney problem since receiving their last provision of the metformin pharmaceutical composition,
an alcohol consumption status of the subject,
whether the subject has experienced a symptom of ketoacidosis since receiving their last provision of the metformin pharmaceutical composition,
whether the subject has experienced a symptom of lactic acidosis since receiving their last provision of the metformin pharmaceutical composition,
whether the subject has experienced an illness causing vomiting, diarrhea, or fever since receiving their last provision of the metformin pharmaceutical composition,
whether the subject has experienced a symptom of a liver problem since receiving their last provision of the metformin pharmaceutical composition,
whether the subject has experienced a heart attack, severe infection, or stroke since receiving their last provision of the metformin pharmaceutical composition,
a surgery status of the subject,
whether the subject has experienced a symptom of dehydration since receiving their last provision of the metformin pharmaceutical composition,
whether the subject is taking a diabetes medication, and
if the subject has been taking the metformin pharmaceutical composition for at least a predetermined period of time, a blood sugar level of the subject;
ii) running all or a portion of the second plurality of survey results against a third plurality of filters of the first category class, wherein, when a respective filter in the third plurality of filters is fired, the subject is deemed not qualified for the metformin pharmaceutical composition and the re-fulfillment process is terminated without authorizing provision of the metformin pharmaceutical composition to the subject, wherein the third plurality of filters comprise:
a second pregnancy filter that is fired at least when the second plurality of survey results indicates that the subject is pregnant or the subject is breastfeeding,
a kidney disease filter that is fired at least when the second plurality of survey results indicates that the subject has experienced a kidney problem since receiving their last provision of the metformin pharmaceutical composition,
a second alcohol consumption filter,
a ketoacidosis symptom filter that is fired at least when the second plurality of survey results indicates that the subject has experienced a symptom of ketoacidosis since receiving their last provision of the metformin pharmaceutical composition,
a lactic acidosis symptom filter that is fired at least when the second plurality of survey results indicates that the subject has experienced a symptom of lactic acidosis since receiving their last provision of the metformin pharmaceutical composition,
an illness filter that is fired at least when the second plurality of survey results indicates that the user has experienced an illness causing vomiting, diarrhea, or fever since receiving their last provision of the metformin pharmaceutical composition, and
a second blood sugar filter that is fired at least when:
  a) the subject has been taking the metformin pharmaceutical composition for a threshold amount of time, and
  b) the second plurality of survey results indicates that the subject has a blood sugar level of at least a second ceiling blood sugar level;
iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises:
  a second liver disease filter that is fired at least when the second plurality of survey results indicates that the subject has experienced a liver problem since receiving their last provision of the metformin pharmaceutical composition,
  a second medical issue filter that is fired at least when the second plurality of survey results indicates that the subject has had a heart attack, the subject has had a severe infection, or the subject has had a stroke since receiving their last provision of the metformin pharmaceutical composition,
  a second surgery filter that is fired at least when the second plurality of survey results indicates that the subject has undergone surgery since receiving their last provision of the metformin pharmaceutical composition, the subject is planning on undergoing surgery, or the subject is planning on having an x-ray procedure that includes injection of a contrast agent since,
  a second dehydration filter that is fired at least when the second plurality of survey results indicates that the subject has experienced, since receiving their last provision of the metformin pharmaceutical composition, a symptom of dehydration, and
  a second diabetes medication filter that is fired at least when the second plurality of survey results indicates that the subject is taking a diabetes medication, and
iv) obtaining acknowledgment from the subject for the warning issued to the subject by any filter in the fourth plurality of filters; and
v) proceeding with the re-fulfillment process when a) the re-fulfillment process is not already terminated by the firing of a filter in the third plurality of filters and b) the subject has acknowledged each warning associated with each filter in the third plurality of filers that was fired and that is associated with a warning, wherein the re-fulfillment process further comprises:
  storing an indication in the subject profile of a re-order for the metformin pharmaceutical composition,
  communicating the over-the-counter facts label for the metformin pharmaceutical composition to the subject, and
  authorizing, upon confirmation from the subject that the over-the-counter drug facts label has been received and read, a re-order provision of the metformin pharmaceutical composition to the subject; and
F) administering the metformin pharmaceutical composition to the subject after authorization of the re-order provision.

15. The method of claim 14, wherein the algorithm also fires the second alcohol consumption filter when the first plurality of survey results indicates that the subject, on average, consumes at least a predetermined number of alcoholic drinks over a predetermined period of time.

16. The method of claim 14, wherein a symptom of ketoacidosis, which is capable of firing the ketoacidosis filter, is selected from the group consisting of an increase of ketones in the blood of the subject, an increase of ketones in the urine of the subject, nausea, tiredness, vomiting, trouble breather, and abdominal pain.

17. The method of claim 14, wherein a symptom of lactic acidosis, which is capable of firing the lactic acidosis symptom filter, is selected from the group consisting of cold feelings in the subject's hands or feet, dizziness, lightheadedness, slow or irregular heartbeat, feeling very weak or tired, unusual muscle pain, difficulty breathing, stomach pains, nausea, and vomiting.

18. The method of claim 14, wherein the second baseline blood sugar level used in the second blood sugar filter is 7% glycated hemoglobin.

19. The method of claim 1, wherein the lowering blood sugar is to treat Type 2 diabetes.

* * * * *